(12) United States Patent
Xu et al.

(10) Patent No.: US 12,018,297 B2
(45) Date of Patent: Jun. 25, 2024

(54) NUCLEASE-MEDIATED NUCLEIC ACID MODIFICATION

(71) Applicant: The Regents of The University of Michigan, Ann Arbor, MI (US)

(72) Inventors: Jie Xu, Troy, MI (US); Jifeng Zhang, Ann Arbor, MI (US); Yuqing Eugene Chen, Superior Township, MI (US); Dongshan Yang, Ann Arbor, MI (US)

(73) Assignee: The Regents of The University of Michigan, Ann Arbor, MI (US)

( * ) Notice: Subject to any disclaimer, the term of this patent is extended or adjusted under 35 U.S.C. 154(b) by 114 days.

(21) Appl. No.: 17/258,776

(22) PCT Filed: May 6, 2019

(86) PCT No.: PCT/US2019/030913
§ 371 (c)(1),
(2) Date: Jan. 8, 2021

(87) PCT Pub. No.: WO2020/018166
PCT Pub. Date: Jan. 23, 2020

(65) Prior Publication Data
US 2021/0301272 A1    Sep. 30, 2021

Related U.S. Application Data

(60) Provisional application No. 62/698,376, filed on Jul. 16, 2018.

(51) Int. Cl.
*C12N 9/22* (2006.01)
*A01K 67/0275* (2024.01)
(Continued)

(52) U.S. Cl.
CPC ............ *C12N 9/22* (2013.01); *A01K 67/0275* (2013.01); *C12N 15/102* (2013.01);
(Continued)

(58) Field of Classification Search
None
See application file for complete search history.

(56) References Cited

U.S. PATENT DOCUMENTS

| 5,034,506 A | 7/1991 | Summerton et al. |
| 6,001,983 A | 12/1999 | Benner |

(Continued)

FOREIGN PATENT DOCUMENTS

| WO | WO 93/03769 | 3/1993 |
| WO | WO 93/09239 | 5/1993 |

(Continued)

OTHER PUBLICATIONS

Davies et al., Interaction with the BRCA2 C terminus protects RAD51-DNA filaments from disassembly by BRC repeats, Nature Structural and Molecular Biology, vol. 4, No. 6, pp. 475-484, Jun. 2007.*

(Continued)

*Primary Examiner* — Richard G Hutson
(74) *Attorney, Agent, or Firm* — Casimir Jones, S.C.; Thomas A. Isenbarger

(57) ABSTRACT

Provided herein is technology relating to molecular biological manipulation of genes and genomes and particularly, but not exclusively, to CRISPR (Clustered Regularly Interspaced Short Palindromic Repeats) methods, compositions, systems, and kits for improved genetic editing.

15 Claims, 37 Drawing Sheets

Specification includes a Sequence Listing.

(51) Int. Cl.
    *C12N 15/10* (2006.01)
    *C12N 15/11* (2006.01)
    *C12N 15/85* (2006.01)

(52) U.S. Cl.
    CPC ........ *C12N 15/111* (2013.01); *C12N 15/8509* (2013.01); *A01K 2207/05* (2013.01); *A01K 2217/072* (2013.01); *C07K 2319/81* (2013.01); *C12N 2310/20* (2017.05)

(56) References Cited

U.S. PATENT DOCUMENTS

| | | | |
|---|---|---|---|
| 7,078,387 | B1 | 7/2006 | Leiden et al. |
| 9,790,490 | B2 | 10/2017 | Zhang et al. |
| 2011/0230839 | A1 | 9/2011 | Bahrami et al. |
| 2015/0071899 | A1* | 3/2015 | Liu .................. C12N 9/1241 435/325 |
| 2017/0051312 | A1 | 2/2017 | Jinek et al. |
| 2018/0155716 | A1 | 6/2018 | Zhang et al. |

FOREIGN PATENT DOCUMENTS

| | | | |
|---|---|---|---|
| WO | WO 93/19191 | 9/1993 | |
| WO | WO 94/12649 | 6/1994 | |
| WO | WO 94/28938 | 12/1994 | |
| WO | WO 95/00655 | 1/1995 | |
| WO | WO 95/11984 | 5/1995 | |
| WO | WO 96/39154 | 12/1996 | |
| WO | WO 97/03211 | 1/1997 | |
| WO | WO 2016/054326 | 4/2016 | |
| WO | WO 2017/142923 | 8/2017 | |
| WO | WO-2017142923 A1 * | 8/2017 | ............ C07H 21/02 |
| WO | WO 2020/18166 | 1/2020 | |

OTHER PUBLICATIONS

Ngo et al. in the Protein Folding Problem and Tertiary Structure Prediction, 1994, Merz et al. (ed.), Birkhauser, Boston, MA, pp. 433 and 492-495.*
International Search Report and Written Opinion for PCT/US2019/030913. dated Aug. 7, 2019. 16 pages.
Abudayyeh et al., RNA targeting with CRISPR-Cas13a. Nature. Oct. 12, 2017;550(7675):280-284.
Ali et al., Adeno-associated virus gene transfer to mouse retina. Hum Gene Ther. Jan. 1, 1998;9(1):81-6.
Ali et al., Gene transfer into the mouse retina mediated by an adeno-associated viral vector. Hum Mol Genet. May 1996;5(5):591-4.
Altschul et al., Basic local alignment search tool. J Mol Biol. Oct. 5, 1990;215(3):403-10.
Barrangou et al., CRISPR provides acquired resistance against viruses in prokaryotes. Science. Mar. 23, 2007;315(5819):1709-12.
Baserga et al., Gene regulation by IGF-I. Mol Reprod Dev. Aug. 1993;35(4):353-6; discussion 356-7.
Bennett et al., Real-time, noninvasive in vivo assessment of adeno-associated virus-mediated retinal transduction. Invest Ophthalmol Vis Sci. Dec. 1997;38(13):2857-63.
Bitter et al., Expression and secretion vectors for yeast. Methods Enzymol. 1987;153:516-44.
Borras et al., Adenoviral reporter gene transfer to the human trabecular meshwork does not alter aqueous humor outflow. Relevance for potential gene therapy of glaucoma. Gene Ther. Apr. 1999;6(4):515-24.
Braasch et al., Novel antisense and peptide nucleic acid strategies for controlling gene expression. Biochemistry. Apr. 9, 2002;41(14):4503-10.
Carlson et al., Efficient TALEN-mediated gene knockout in livestock. Proc Natl Acad Sci U S A. Oct. 23, 2012;109(43):17382-7.
Charpentier et al., CtIP fusion to Cas9 enhances transgene integration by homology-dependent repair. Nat Commun. Mar. 19, 2018;9(1):1133. 11 pages.
Chen et al., Enhanced proofreading governs CRISPR-Cas9 targeting accuracy. Nature. Oct. 19, 2017;550(7676):407-410.
Chylinski et al., The tracrRNA and Cas9 families of type II CRISPER-Cas immunity systems. RNA Biology 2013;10:5, 1-12.
Clark et al., A Tale of two nucleases: gene targeting for the masses? Zebrafish. Sep. 2011;8(3):147-9.
Cong et al. Multiplex genome engineering using CRISPR/Cas systems. Science. Feb. 15, 2013;339(6121):819-23.
Curiel et al., High-efficiency gene transfer mediated by adenovirus coupled to DNA-polylysine complexes. Hum Gene Ther. Apr. 1992;3(2):147-54.
Darty et al., VARNA: Interactive drawing and editing of the RNA secondary structure. Bioinformatics. Aug. 1, 2009;25(15):1974-5.
Davies et al., Interaction with the BRCA2 C terminus protects RAD51-DNA filaments from disassembly by BRC repeats. Nat Struct Mol Biol. Jun. 2007;14(6):475-83.
Davis et al., Small molecule-triggered Cas9 protein with improved genome-editing specificity. Nat Chem Biol. May 2015;11(5):316-8.
Denman. Using RNAFOLD to predict the activity of small catalytic RNAs. Biotechniques. Dec. 1993;15(6):1090-5.
Dewitt et al., Selection-free genome editing of the sickle mutation in human adult hematopoietic stem/progenitor cells. Sci Transl Med. Oct. 12, 2016;8(360):360ra134. 1-20.
Ding et al., Improving CRISPR-Cas9 Genome Editing Efficiency by Fusion with Chromatin-Modulating Peptides. Crispr J. Feb. 2019;2:51-63.
Doty et al., Strand Separation and Specific Recombination in Deoxyribonucleic Acids: Physical Chemical Studies. Proc Natl Acad Sci U S A. Apr. 1960;46(4):461-76.
Doudna et al., Genome editing. The new frontier of genome engineering with CRISPR-Cas9. Science. Nov. 28, 2014;346(6213):1258096. 11 pages.
Eckstein. Oligonucleotides and Analogues: A Practical Approach. Oxford University Press. 1991. TOC only. 11 pages.
Esvelt et al., Orthogonal Cas9 proteins for RNA-guided gene regulation and editing. Nat Methods. Nov. 2013;10(11):1116-21.
Flannery et al., Efficient photoreceptor-targeted gene expression in vivo by recombinant adeno-associated virus. Proc Natl Acad Sci U S A. Jun. 24, 1997;94(13):6916-21.
Flotte et al., Stable in vivo expression of the cystic fibrosis transmembrane conductance regulator with an adeno-associated virus vector. Proc Natl Acad Sci U S A. Nov. 15, 1993;90(22):10613-7.
Fonfara et al., Phylogeny of Cas9 determines functional exchangeability of dual-RNA and Cas9 among orthologous type II CRISPR-Cas systems. Nucleic Acids Res. Feb. 2014;42(4):2577-90.
Fu et al., High-frequency off-target mutagenesis induced by CRISPR-Cas nucleases in human cells. Nat Biotechnol. Sep. 2013;31(9):822-6.
Gu et al., Efficient generation of targeted large insertions by microinjection into two-cell-stage mouse embryos. Nat Biotechnol. Aug. 2018;36(7):632-637.
Guschin et al., A rapid and general assay for monitoring endogenous gene modification. Methods Mol Biol. 2010;649:247-56.
Gutschner et al., Post-translational Regulation of Cas9 during G1 Enhances Homology-Directed Repair. Cell Rep. Feb. 16, 2016;14(6):1555-1566.
Harmsen et al., DNA mismatch repair and oligonucleotide end-protection promote base-pair substitution distal from a CRISPR/Cas9-induced DNA break. Nucleic Acids Res. Apr. 6, 2018;46(6):2945-2955.
Heyer et al., Regulation of homologous recombination in eukaryotes. Annu Rev Genet. 2010;44:113-39.
Hofacker et al., Memory efficient folding algorithms for circular RNA secondary structures. Bioinformatics. May 15, 2006;22(10):1172-6.
Howden et al., A Cas9 Variant for Efficient Generation of Indel-Free Knockin or Gene-Corrected Human Pluripotent Stem Cells. Stem Cell Reports. Sep. 13, 2016;7(3):508-517.
Hu et al., Evolved Cas9 variants with broad PAM compatibility and high DNA specificity. Nature. Apr. 5, 2018;556(7699):57-63.

(56) References Cited

OTHER PUBLICATIONS

Iyer et al., 7.05. Oligonucleotide synthesis. In: Comprehensive Natural Products Chemistry, vol. 7: DNA and Aspects of Molecular Biology. Elsevier, Amsterdam. 1999. pp. 105-152.
Jinek et al., A programmable dual-RNA-guided DNA endonuclease in adaptive bacterial immunity. Science. Aug. 17, 2012;337(6096):816-21.
Jomary et al., Rescue of photoreceptor function by AAV-mediated gene transfer in a mouse model of inherited retinal degeneration. Gene Ther. Jul. 1997;4(7):683-90.
Kabadi et al., Multiplex CRISPR/Cas9-based genome engineering from a single lentiviral vector. Nucleic Acids Res. Oct. 29, 2014;42(19):e147. 11 pages.
Kan et al., Mechanisms of precise genome editing using oligonucleotide donors. Genome Res. Jul. 2017;27(7):1099-1111.
Kawai et al., Transformation of *Saccharomyces cerevisiae* and other fungi: methods and possible underlying mechanism. Bioeng Bugs. Nov.-Dec. 2010;1(6):395-403.
Kim et al., Highly efficient RNA-guided genome editing in human cells via delivery of purified Cas9 ribonucleoproteins. Genome Res. Jun. 2014;24(6):1012-9.
Kleinstiver et al., High-fidelity CRISPR-Cas9 nucleases with no detectable genome-wide off-target effects. Nature. Jan. 28, 2016;529(7587):490-5.
Kulcsár et al., Crossing enhanced and high fidelity SpCas9 nucleases to optimize specificity and cleavage. Genome Biol. Oct. 6, 2017;18(1):190. 1-17.
Lee et al., The Neisseria meningitidis CRISPR-Cas9 System Enables Specific Genome Editing in Mammalian Cells. Mol Ther. Mar. 2016;24(3):645-54.
Lehninger. DNA: The Structure of Chromosomes and Genes. Principles of Biochemistry. Worth Pub. 1982. pp. 793-800.
Levardon et al., Expansion of Airway Basal Cells and Generation of Polarized Epithelium. Bio Protoc. Jun. 5, 2018;8(11):e2877. 16 pages.
Li et al., In vivo transfer of a reporter gene to the retina mediated by an adenoviral vector. Invest Ophthalmol Vis Sci. Apr. 1994;35(5):2543- 9.
Li et al., Phenotype correction in retinal pigment epithelium in murine mucopolysaccharidosis VII by adenovirus-mediated gene transfer. Proc Natl Acad Sci U S A. Aug. 15, 1995;92(17):7700-4.
Lin et al., Fusion of SpCas9 to *E. coli* Rec A protein enhances CRISPR-Cas9 mediated gene knockout in mammalian cells. J Biotechnol. Apr. 10, 2017;247:42-49.
Lin et al., Synthesis and duplex stability of oligonucleotides containing cytosine-thymine analogues. Nucleic Acids Res. Dec. 25, 1989;17(24):10373-83.
Lin et al., Synthesis of oligodeoxyribonucleotides containing degenerate bases and their use as primers in the polymerase chain reaction. Nucleic Acids Res. Oct. 11, 1992;20(19):5149-52.
Lott et al., The importin β binding domain as a master regulator of nucleocytoplasmic transport. Biochim Biophys Acta. Sep. 2011;1813(9):1578-92.
Maeder et al., CRISPR RNA-guided activation of endogenous human genes. Nat Methods. Oct. 2013;10(10):977-9.
Marmur et al., Strand Separation and Specific Recombination in Deoxyribonucleic Acids: Biological Studies. Proc Natl Acad Sci U S A. Apr. 1960;46(4):453-61.
Mata et al., A hexameric phosphorothioate oligonucleotide telomerase inhibitor arrests growth of Burkitt's lymphoma cells in vitro and in vivo. Toxicol Appl Pharmacol. May 1997;144(1):189-97.
Mendelson et al., Expression and rescue of a nonselected marker from an integrated AAV vector. Virology. Sep. 1988; 166(1):154-65.
Milligan. Mechanisms of multifunctional signalling by G protein-linked receptors. Trends Pharmacol Sci. Jun. 1993;14(6):239-44.
Miyoshi et al., Stable and efficient gene transfer into the retina using an HIV-based lentiviral vector. Proc Natl Acad Sci U S A. Sep. 16, 1997;94(19):10319-23.
NCBI accession NG_012772.3. Aug. 21, 2022. 29 pages.

Needleman et al., A general method applicable to the search for similarities in the amino acid sequence of two proteins. J Mol Biol. Mar. 1970;48(3):443-53.
Panyam et al., Biodegradable nanoparticles for drug and gene delivery to cells and tissue. Adv Drug Deliv Rev. Sep. 2012. 13. 11 pages.
Qi et al., Repurposing CRISPR as an RNA-guided platform for sequence-specific control of gene expression. Cell. Feb. 28, 2013;152(5):1173-83.
Ran et al., In vivo genome editing using *Staphylococcus aureus* Cas9. Nature. Apr. 9, 2015;520(7546):186-91.
Rolling et al., Evaluation of adeno-associated virus-mediated gene transfer into the rat retina by clinical fluorescence photography. Hum Gene Ther. Mar. 1, 1999;10(4):641-8.
Sakamoto et al., A vitrectomy improves the transfection efficiency of adenoviral vector-mediated gene transfer to Muller cells. Gene Therapy, 1998; 5(8), 1088-1097.
Sambrook et al., Molecular Cloning: A Laboratory Manual, Second Edition, Cold Spring Harbor Laboratory Press, Cold Spring Harbor . 1989. 36 pages.
Sambrook et al., Molecular Cloning: A Laboratory Manual, Third Edition, Cold Spring Harbor Laboratory Press, Cold Spring Harbor. 2001. TOC only. 23 pages.
Samstag et al., Synthesis and properties of new antisense oligodeoxynucleotides containing benzylphosphonate linkages. Antisense Nucleic Acid Drug Dev. 1996 Fall;6(3):153-6.
Samulski et al., Helper-free stocks of recombinant adeno-associated viruses: normal integration does not require viral gene expression. J Virol. Sep. 1989;63(9):3822-8.
Schumann et al., Generation of knock-in primary human T cells using Cas9 ribonucleoproteins. Proc Natl Acad Sci U S A. Aug. 18, 2015;112(33):10437-42.
Schweitzer et al., Aromatic Nonpolar Nucleosides as Hydrophobic Isosteres of Pyrimidine and Purine Nucleosides. J Org Chem. Dec. 1, 1994;59(24):7238-7242.
Schweitzer et al., Hydrophobic, Non-Hydrogen-Bonding Bases and Base Pairs in DNA. J Am Chem Soc. Feb. 22, 1995;117(7):1863-1872.
Shen et al., Efficient genome modification by CRISPR-Cas9 nickase with minimal off-target effects. Nat Methods. Apr. 2014;11(4):399-402.
Slaymaker et al., Rationally engineered Cas9 nucleases with improved specificity. Science. Jan. 1, 2016;351(6268):84-8.
Smith et al., Comparison of Biosequences. Adv. Appl. Math., 1981, 2, 482-489.
Strauss-Soukup et al., Role of asymmetric phosphate neutralization in DNA bending by PU.1. J Biol Chem. Dec. 12, 1997;272(50):31570-5.
Takahashi et al., Rescue from photoreceptor degeneration in the rd mouse by human immunodeficiency virus vector-mediated gene transfer. J Virol. Sep. 1999;73(9):7812-6.
Tanka et al., Conformational variations in an infectious protein determine prion strain differences. Nature. Mar. 18, 2004;428(6980):323-8.
Vakulskas et al., A high-fidelity Cas9 mutant delivered as a ribonucleoprotein complex enables efficient gene editing in human hematopoietic stem and progenitor cells. Nat Med. Aug. 2018;24(8):1216-1224.
Vicente et al., A CyclinB2-Cas9 fusion promotes the homology-directed repair of double-strand breaks. bioR$_X$iv. 2019. 17 pages.
Wahlestedt et al., Potent and nontoxic antisense oligonucleotides containing locked nucleic acids. Proc Natl Acad Sci U S A. May 9, 2000;97(10):5633-8.
Wang et al., Cyclohexene Nucleic Acids (CeNA): Serum Stable Oligonucleotides that Activate RNase H and Increase Duplex Stability with Complementary RNA. J. Am. Chem. Soc., 2000, 122, 8595-8602.
Wang et al., One-step generation of mice carrying mutations in multiple genes by CRISPR/Cas-mediated genome engineering. Cell. May 9, 2013;153(4):910-8.
Williams et al., Introduction of foreign genes into tissues of living mice by DNA-coated microprojectiles. Proc Natl Acad Sci U S A. Apr. 1, 1991;88(7):2726-30.

(56) References Cited

OTHER PUBLICATIONS

Wilson et al., Hepatocyte-directed gene transfer in vivo leads to transient improvement of hypercholesterolemia in low density lipoprotein receptor-deficient rabbits. J Biol Chem. Jan. 15, 1992;267(2):963-7.

Wu et al., Receptor-mediated gene delivery and expression in vivo. J Biol Chem. Oct. 15, 1988;263(29):14621-4.

Wu et al., Receptor-mediated in vitro gene transformation by a soluble DNA carrier system. J Biol Chem. Apr. 5, 1987;262(10):4429-32.

Xu et al., Efficient homology-directed gene editing by CRISPR/Cas9 in human stem and primary cells using tube electroporation. Sci Rep. Aug. 3, 2018;8(1):11649. 11 pages.

Yang et al., Effective gene targeting in rabbits using RNA-guided Cas9 nucleases. J Mol Cell Biol. Feb. 2014;6(1):97-9.

Yang et al., One-step generation of mice carrying reporter and conditional alleles by CRISPR/Cas-mediated genome engineering. Cell. Sep. 12, 2013;154(6):1370-9.

Yang et al., Production of apolipoprotein C-III knockout rabbits using zinc finger nucleases. J Vis Exp. Nov. 18, 2013;(81):e50957. 7 pages.

Zhang et al., PowerBLAST: a new network BLAST application for interactive or automated sequence analysis and annotation. Genome Res. Jun. 1997;7(6):649-56.

Zhang et al., Processing-independent CRISPR RNAs limit natural transformation in Neisseria meningitidis. Mol Cell. May 23, 2013;50(4):488-503.

Zhu et al., The iCRISPR platform for rapid genome editing in human pluripotent stem cells. Methods Enzymol. 2014;546:215-50.

Wilde, J.J. et al. Efficient embryonic homozygous gene conversion via RAD51-enhanced interhomolog repair. Cell. Jun. 10, 2021;184(12):3267-3280.e18.

Song, J. et al. RS-1 enhances CRISPR/Cas9- and TALEN-mediated knock-in efficiency. Nat Commun. Jan. 28, 2016;7:10548.

Rees, H.A. et al. Development of hRad51-Cas9 nickase fusions that mediate HDR without double-stranded breaks. Nat Commun. May 17, 2019;10(1):2212.

Clement et al., CRISPResso2 provides accurate and rapid genome editing sequence analysis. Nat Biotechnol. Mar. 2019;37(3):224-226.

Huai et al., Structural insights into DNA cleavage activation of CRISPR-Cas9 system. Nat Commun. Nov. 9, 2017;8(1):1375. 9 pages.

International Search Report and Written Opinions for PCT/US21/46247. dated Feb. 3, 2022. 21 pages.

Nunez et al., Integrase-mediated spacer acquisition during CRISPR-Cas adaptive immunity. Nature. Mar. 12, 2015;519(7542):193-8.

Sternberg et al., Adaptation in CRISPR-Cas Systems. Mol Cell. Mar. 17, 2016;61(6):797-808.

\* cited by examiner

AAVS1 locus

ROSA26 locus

***

VEGFA sgRNA 1 on target     GGGTGGGGGGAGTTTGCTCCTGG (SEQ ID NO: 10)

off target 1    GGGAGGGTGGAGTTTGCTCCTGG (SEQ ID NO: 11)

on target    GCATTTTCAGGAGGAAGCGATGG (SEQ ID NO: 18)

off target 1  GCATTTTCAGAAGGAAGCAAGG (SEQ ID NO: 19)

FIG. 9A

| Locus | target sequence | |
|---|---|---|
| EGFR | CTGCGTGATGAGCTGCACGG | (SEQ ID NO: 22) |
| Mybpc3 | GGAGTTTGAGTGAAGTAT | (SEQ ID NO: 23) |
| HBB | CTTGCCCACAGGGCAGTAA | (SEQ ID NO: 24) |
| B2M | CCAGAAAGAGAGAGTAGCGC | (SEQ ID NO: 25) |
| NKX2.1 | AACAGAAGTACCTGTCGGCGC | (SEQ ID NO: 26) |

FIG. 9B

| Locus | oligo sequences | |
|---|---|---|
| EGFR | ACGTGATGGCCAGCGTGGACAACCCCACGTGTGCCGCCTGCTGGGCATCTGCCTCACCTCTACAGTCCAACTGATTACCCAGCTCATGCCCTTCGGCTGCCTCCTGGACTATGTCCGGGAACACAAAGACAATATTGGCTCCCAG | (SEQ ID NO: 27) |
| Mybpc3 | GCCCCCTGTGCTCATCACGCGCCCCTTGGAGGACCAGCTGGTGATGGTGGGGCAGCGGGTGGAGTTTGCGAGGTATCGGAGGAGGGGGCGCAAGTCAAATGGTGAGTTCCAGAAGCACGGGGCATGGGTGTTGGGGGCAT | (SEQ ID NO: 28) |
| HBB | TCTGACACAACTGTGTTCACTAGCAACCTCAAACAGACACCATGGTGCATCTGACTCCTGTGGAGAAGTCTGCAGTTACTGCCCTGTGGGGCAAGGTGAACGTGGATGAAGTTGGTGGTGAGGCCCTGGGCAG | (SEQ ID NO: 29) |
| B2M | GGGTAGGAGAGACTCACGCTGGATAGCCTCCAGGCCAGAAAGAGAGAGTAGCGCGACGCACAGCTAAGGCCACGGAGCGAGACATCTCGG CCCGAATGCT | (SEQ ID NO: 30) |
| NKX2.1 | GGAAGCGCCGGGTGCTCTTCTCGCAGGCGCAGGTGTACGAGCTGGAGCGACGCTTCAAGCAACAGAAGTACCTGTCGGCGCCCGAGCTCGAGCACCTGGCCAGCATGATCCACCTGACGCCCACGCAGGTCAAGATCTGGTTCCAGAACCACCGCTACAAAATGAAGCG | (SEQ ID NO: 31) |

SEQUENCE LISTING

```
<160> NUMBER OF SEQ ID NOS: 31

<210> SEQ ID NO 1
<211> LENGTH: 36
<212> TYPE: PRT
<213> ORGANISM: Homos sapiens

<400> SEQUENCE: 1

Ala Leu Asp Phe Leu Ser Arg Leu Pro Leu Pro Pro Val Ser Pro
1               5                   10                  15

Ile Cys Thr Phe Val Ser Pro Ala Ala Gln Lys Ala Phe Gln Pro Pro
            20                  25                  30

Arg Ser Cys Gly
        35

<210> SEQ ID NO 2
<211> LENGTH: 23
<212> TYPE: DNA
<213> ORGANISM: Artificial sequence
<220> FEATURE:
<223> OTHER INFORMATION: DNA encoding a guide RNA

<400> SEQUENCE: 2
ggggccacta gggacaggat tgg                                           23

<210> SEQ ID NO 3
<211> LENGTH: 20
<212> TYPE: DNA
<213> ORGANISM: Artificial sequence
<220> FEATURE:
```

```
<223> OTHER INFORMATION: DNA encoding a guide RNA

<400> SEQUENCE: 3
ggggccacta gggacaggat                                                20

<210> SEQ ID NO 4
<211> LENGTH: 25
<212> TYPE: DNA
<213> ORGANISM: Artificial sequence
<220> FEATURE:
<223> OTHER INFORMATION: DNA encoding a guide RNA

<400> SEQUENCE: 4
aattgagcct gccgtgtttc tgagg                                          25

<210> SEQ ID NO 5
<211> LENGTH: 22
<212> TYPE: DNA
<213> ORGANISM: Artificial sequence
<220> FEATURE:
<223> OTHER INFORMATION: DNA encoding a guide RNA

<400> SEQUENCE: 5
aattgagcct gccgtgtttc tg                                             22

<210> SEQ ID NO 6
<211> LENGTH: 56
<212> TYPE: RNA
<213> ORGANISM: Artificial sequence
<220> FEATURE:
<223> OTHER INFORMATION: DNA encoding a guide RNA
<220> FEATURE:
<221> NAME/KEY: misc_feature
<222> LOCATION: (1)..(12)
<223> OTHER INFORMATION: n is a, c, g, or u

<400> SEQUENCE: 6
nnnnnnnnnn nnrgrururu rarargrarg rcrurarurg rcrurgruru rururg        56

<210> SEQ ID NO 7
<211> LENGTH: 108
<212> TYPE: DNA
<213> ORGANISM: Artificial sequence
<220> FEATURE:
<223> OTHER INFORMATION: Degenerate DNA sequence
<220> FEATURE:
<221> NAME/KEY: misc_feature
<222> LOCATION: (3)..(3)
<223> OTHER INFORMATION: n is a, c, g, or t
<220> FEATURE:
<221> NAME/KEY: misc_feature
<222> LOCATION: (6)..(6)
<223> OTHER INFORMATION: n is a, c, g, or t
<220> FEATURE:
<221> NAME/KEY: misc_feature
<222> LOCATION: (15)..(15)
<223> OTHER INFORMATION: n is a, c, g, or t
<220> FEATURE:
<221> NAME/KEY: misc_feature
<222> LOCATION: (18)..(18)
<223> OTHER INFORMATION: n is a, c, g, or t
<220> FEATURE:
<221> NAME/KEY: misc_feature
<222> LOCATION: (21)..(21)
<223> OTHER INFORMATION: n is a, c, g, or t
<220> FEATURE:
<221> NAME/KEY: misc_feature
<222> LOCATION: (24)..(24)
<223> OTHER INFORMATION: n is a, c, g, or t
<220> FEATURE:
<221> NAME/KEY: misc_feature
```

```
<222> LOCATION: (27)..(27)
<223> OTHER INFORMATION: n is a, c, g, or t
<220> FEATURE:
<221> NAME/KEY: misc_feature
<222> LOCATION: (30)..(30)
<223> OTHER INFORMATION: n is a, c, g, or t
<220> FEATURE:
<221> NAME/KEY: misc_feature
<222> LOCATION: (33)..(33)
<223> OTHER INFORMATION: n is a, c, g, or t
<220> FEATURE:
<221> NAME/KEY: misc_feature
<222> LOCATION: (36)..(36)
<223> OTHER INFORMATION: n is a, c, g, or t
<220> FEATURE:
<221> NAME/KEY: misc_feature
<222> LOCATION: (39)..(39)
<223> OTHER INFORMATION: n is a, c, g, or t
<220> FEATURE:
<221> NAME/KEY: misc_feature
<222> LOCATION: (42)..(42)
<223> OTHER INFORMATION: n is a, c, g, or t
<220> FEATURE:
<221> NAME/KEY: misc_feature
<222> LOCATION: (45)..(45)
<223> OTHER INFORMATION: n is a, c, g, or t
<220> FEATURE:
<221> NAME/KEY: misc_feature
<222> LOCATION: (48)..(48)
<223> OTHER INFORMATION: n is a, c, g, or t
<220> FEATURE:
<221> NAME/KEY: misc_feature
<222> LOCATION: (57)..(57)
<223> OTHER INFORMATION: n is a, c, g, or t
<220> FEATURE:
<221> NAME/KEY: misc_feature
<222> LOCATION: (63)..(63)
<223> OTHER INFORMATION: n is a, c, g, or t
<220> FEATURE:
<221> NAME/KEY: misc_feature
<222> LOCATION: (66)..(66)
<223> OTHER INFORMATION: n is a, c, g, or t
<220> FEATURE:
<221> NAME/KEY: misc_feature
<222> LOCATION: (69)..(69)
<223> OTHER INFORMATION: n is a, c, g, or t
<220> FEATURE:
<221> NAME/KEY: misc_feature
<222> LOCATION: (72)..(72)
<223> OTHER INFORMATION: n is a, c, g, or t
<220> FEATURE:
<221> NAME/KEY: misc_feature
<222> LOCATION: (75)..(75)
<223> OTHER INFORMATION: n is a, c, g, or t
<220> FEATURE:
<221> NAME/KEY: misc_feature
<222> LOCATION: (84)..(84)
<223> OTHER INFORMATION: n is a, c, g, or t
<220> FEATURE:
<221> NAME/KEY: misc_feature
<222> LOCATION: (93)..(93)
<223> OTHER INFORMATION: n is a, c, g, or t
<220> FEATURE:
<221> NAME/KEY: misc_feature
<222> LOCATION: (96)..(96)
<223> OTHER INFORMATION: n is a, c, g, or t
<220> FEATURE:
<221> NAME/KEY: misc_feature
<222> LOCATION: (99)..(99)
<223> OTHER INFORMATION: n is a, c, g, or t
<220> FEATURE:
<221> NAME/KEY: misc_feature
<222> LOCATION: (102)..(102)
<223> OTHER INFORMATION: n is a, c, g, or t
<220> FEATURE:
<221> NAME/KEY: misc_feature
<222> LOCATION: (108)..(108)
<223> OTHER INFORMATION: n is a, c, g, or t
```

-continued

<400> SEQUENCE: 7

```
gcnytngayt tyytnwsnmg nytnccnytn ccnccnccng tnwsnccnat htgyacntty    60
gtnwsnccng cngcncaraa rgcnttycar ccnccnmgnw sntgyggn                108
```

<210> SEQ ID NO 8
<211> LENGTH: 108
<212> TYPE: DNA
<213> ORGANISM: Homo sapiens

<400> SEQUENCE: 8

```
gccttggatt tcttgagtag actgccttta cctccacctg ttagtcccat ttgtacattt    60
gtttctccgg ctgcacagaa ggcatttcag ccaccaagga gttgtggc                108
```

<210> SEQ ID NO 9
<211> LENGTH: 1368
<212> TYPE: PRT
<213> ORGANISM: Streptococcus pyogenes

<400> SEQUENCE: 9

Met Asp Lys Lys Tyr Ser Ile Gly Leu Asp Ile Gly Thr Asn Ser Val
1               5                   10                  15

Gly Trp Ala Val Ile Thr Asp Glu Tyr Lys Val Pro Ser Lys Lys Phe
            20                  25                  30

Lys Val Leu Gly Asn Thr Asp Arg His Ser Ile Lys Lys Asn Leu Ile
        35                  40                  45

Gly Ala Leu Leu Phe Asp Ser Gly Glu Thr Ala Glu Ala Thr Arg Leu
    50                  55                  60

Lys Arg Thr Ala Arg Arg Arg Tyr Thr Arg Arg Lys Asn Arg Ile Cys
65                  70                  75                  80

Tyr Leu Gln Glu Ile Phe Ser Asn Glu Met Ala Lys Val Asp Asp Ser
                85                  90                  95

Phe Phe His Arg Leu Glu Glu Ser Phe Leu Val Glu Glu Asp Lys Lys
            100                 105                 110

His Glu Arg His Pro Ile Phe Gly Asn Ile Val Asp Glu Val Ala Tyr
        115                 120                 125

His Glu Lys Tyr Pro Thr Ile Tyr His Leu Arg Lys Lys Leu Val Asp
    130                 135                 140

Ser Thr Asp Lys Ala Asp Leu Arg Leu Ile Tyr Leu Ala Leu Ala His
145                 150                 155                 160

Met Ile Lys Phe Arg Gly His Phe Leu Ile Glu Gly Asp Leu Asn Pro
                165                 170                 175

Asp Asn Ser Asp Val Asp Lys Leu Phe Ile Gln Leu Val Gln Thr Tyr
            180                 185                 190

Asn Gln Leu Phe Glu Glu Asn Pro Ile Asn Ala Ser Gly Val Asp Ala
        195                 200                 205

Lys Ala Ile Leu Ser Ala Arg Leu Ser Lys Ser Arg Arg Leu Glu Asn
    210                 215                 220

Leu Ile Ala Gln Leu Pro Gly Glu Lys Lys Asn Gly Leu Phe Gly Asn
225                 230                 235                 240

Leu Ile Ala Leu Ser Leu Gly Leu Thr Pro Asn Phe Lys Ser Asn Phe
                245                 250                 255

Asp Leu Ala Glu Asp Ala Lys Leu Gln Leu Ser Lys Asp Thr Tyr Asp
            260                 265                 270

Asp Asp Leu Asp Asn Leu Leu Ala Gln Ile Gly Asp Gln Tyr Ala Asp
        275                 280                 285

```
Leu Phe Leu Ala Ala Lys Asn Leu Ser Asp Ala Ile Leu Ser Asp
    290                 295                 300
Ile Leu Arg Val Asn Thr Glu Ile Thr Lys Ala Pro Leu Ser Ala Ser
305                 310                 315                 320
Met Ile Lys Arg Tyr Asp Glu His His Gln Asp Leu Thr Leu Leu Lys
                325                 330                 335
Ala Leu Val Arg Gln Gln Leu Pro Glu Lys Tyr Lys Glu Ile Phe Phe
            340                 345                 350
Asp Gln Ser Lys Asn Gly Tyr Ala Gly Tyr Ile Asp Gly Gly Ala Ser
        355                 360                 365
Gln Glu Glu Phe Tyr Lys Phe Ile Lys Pro Ile Leu Glu Lys Met Asp
    370                 375                 380
Gly Thr Glu Glu Leu Leu Val Lys Leu Asn Arg Glu Asp Leu Leu Arg
385                 390                 395                 400
Lys Gln Arg Thr Phe Asp Asn Gly Ser Ile Pro His Gln Ile His Leu
                405                 410                 415
Gly Glu Leu His Ala Ile Leu Arg Arg Gln Glu Asp Phe Tyr Pro Phe
            420                 425                 430
Leu Lys Asp Asn Arg Glu Lys Ile Glu Lys Ile Leu Thr Phe Arg Ile
        435                 440                 445
Pro Tyr Tyr Val Gly Pro Leu Ala Arg Gly Asn Ser Arg Phe Ala Trp
    450                 455                 460
Met Thr Arg Lys Ser Glu Glu Thr Ile Thr Pro Trp Asn Phe Glu Glu
465                 470                 475                 480
Val Val Asp Lys Gly Ala Ser Ala Gln Ser Phe Ile Glu Arg Met Thr
                485                 490                 495
Asn Phe Asp Lys Asn Leu Pro Asn Glu Lys Val Leu Pro Lys His Ser
            500                 505                 510
Leu Leu Tyr Glu Tyr Phe Thr Val Tyr Asn Glu Leu Thr Lys Val Lys
        515                 520                 525
Tyr Val Thr Glu Gly Met Arg Lys Pro Ala Phe Leu Ser Gly Glu Gln
    530                 535                 540
Lys Lys Ala Ile Val Asp Leu Leu Phe Lys Thr Asn Arg Lys Val Thr
545                 550                 555                 560
Val Lys Gln Leu Lys Glu Asp Tyr Phe Lys Lys Ile Glu Cys Phe Asp
                565                 570                 575
Ser Val Glu Ile Ser Gly Val Glu Asp Arg Phe Asn Ala Ser Leu Gly
            580                 585                 590
Thr Tyr His Asp Leu Leu Lys Ile Ile Lys Asp Lys Asp Phe Leu Asp
        595                 600                 605
Asn Glu Glu Asn Glu Asp Ile Leu Glu Asp Ile Val Leu Thr Leu Thr
    610                 615                 620
Leu Phe Glu Asp Arg Glu Met Ile Glu Glu Arg Leu Lys Thr Tyr Ala
625                 630                 635                 640
His Leu Phe Asp Asp Lys Val Met Lys Gln Leu Lys Arg Arg Arg Tyr
                645                 650                 655
Thr Gly Trp Gly Arg Leu Ser Arg Lys Leu Ile Asn Gly Ile Arg Asp
            660                 665                 670
Lys Gln Ser Gly Lys Thr Ile Leu Asp Phe Leu Lys Ser Asp Gly Phe
        675                 680                 685
Ala Asn Arg Asn Phe Met Gln Leu Ile His Asp Asp Ser Leu Thr Phe
    690                 695                 700
```

```
Lys Glu Asp Ile Gln Lys Ala Gln Val Ser Gly Gln Gly Asp Ser Leu
705                 710                 715                 720

His Glu His Ile Ala Asn Leu Ala Gly Ser Pro Ala Ile Lys Lys Gly
            725                 730                 735

Ile Leu Gln Thr Val Lys Val Asp Glu Leu Val Lys Val Met Gly
        740                 745                 750

Arg His Lys Pro Glu Asn Ile Val Ile Glu Met Ala Arg Glu Asn Gln
            755                 760                 765

Thr Thr Gln Lys Gly Gln Lys Asn Ser Arg Glu Arg Met Lys Arg Ile
    770                 775                 780

Glu Glu Gly Ile Lys Glu Leu Gly Ser Gln Ile Leu Lys Glu His Pro
785                 790                 795                 800

Val Glu Asn Thr Gln Leu Gln Asn Glu Lys Leu Tyr Leu Tyr Tyr Leu
            805                 810                 815

Gln Asn Gly Arg Asp Met Tyr Val Asp Gln Glu Leu Asp Ile Asn Arg
        820                 825                 830

Leu Ser Asp Tyr Asp Val Asp His Ile Val Pro Gln Ser Phe Leu Lys
    835                 840                 845

Asp Asp Ser Ile Asp Asn Lys Val Leu Thr Arg Ser Asp Lys Asn Arg
850                 855                 860

Gly Lys Ser Asp Asn Val Pro Ser Glu Glu Val Val Lys Lys Met Lys
865                 870                 875                 880

Asn Tyr Trp Arg Gln Leu Leu Asn Ala Lys Leu Ile Thr Gln Arg Lys
            885                 890                 895

Phe Asp Asn Leu Thr Lys Ala Glu Arg Gly Gly Leu Ser Glu Leu Asp
        900                 905                 910

Lys Ala Gly Phe Ile Lys Arg Gln Leu Val Glu Thr Arg Gln Ile Thr
    915                 920                 925

Lys His Val Ala Gln Ile Leu Asp Ser Arg Met Asn Thr Lys Tyr Asp
930                 935                 940

Glu Asn Asp Lys Leu Ile Arg Glu Val Lys Val Ile Thr Leu Lys Ser
945                 950                 955                 960

Lys Leu Val Ser Asp Phe Arg Lys Asp Phe Gln Phe Tyr Lys Val Arg
            965                 970                 975

Glu Ile Asn Asn Tyr His His Ala His Asp Ala Tyr Leu Asn Ala Val
        980                 985                 990

Val Gly Thr Ala Leu Ile Lys Lys Tyr Pro Lys Leu Glu Ser Glu Phe
    995                 1000                1005

Val Tyr Gly Asp Tyr Lys Val Tyr Asp Val Arg Lys Met Ile Ala
1010                1015                1020

Lys Ser Glu Gln Glu Ile Gly Lys Ala Thr Ala Lys Tyr Phe Phe
1025                1030                1035

Tyr Ser Asn Ile Met Asn Phe Phe Lys Thr Glu Ile Thr Leu Ala
1040                1045                1050

Asn Gly Glu Ile Arg Lys Arg Pro Leu Ile Glu Thr Asn Gly Glu
1055                1060                1065

Thr Gly Glu Ile Val Trp Asp Lys Gly Arg Asp Phe Ala Thr Val
1070                1075                1080

Arg Lys Val Leu Ser Met Pro Gln Val Asn Ile Val Lys Lys Thr
1085                1090                1095

Glu Val Gln Thr Gly Gly Phe Ser Lys Glu Ser Ile Leu Pro Lys
1100                1105                1110

Arg Asn Ser Asp Lys Leu Ile Ala Arg Lys Lys Asp Trp Asp Pro
```

```
                1115                1120                1125

Lys  Lys  Tyr  Gly  Gly  Phe  Asp  Ser  Pro  Thr  Val  Ala  Tyr  Ser  Val
               1130                1135                1140

Leu  Val  Val  Ala  Lys  Val  Glu  Lys  Gly  Lys  Ser  Lys  Lys  Leu  Lys
          1145                1150                1155

Ser  Val  Lys  Glu  Leu  Leu  Gly  Ile  Thr  Ile  Met  Glu  Arg  Ser  Ser
     1160                1165                1170

Phe  Glu  Lys  Asn  Pro  Ile  Asp  Phe  Leu  Glu  Ala  Lys  Gly  Tyr  Lys
1175                1180                1185

Glu  Val  Lys  Lys  Asp  Leu  Ile  Ile  Lys  Leu  Pro  Lys  Tyr  Ser  Leu
     1190                1195                1200

Phe  Glu  Leu  Glu  Asn  Gly  Arg  Lys  Arg  Met  Leu  Ala  Ser  Ala  Gly
1205                1210                1215

Glu  Leu  Gln  Lys  Gly  Asn  Glu  Leu  Ala  Leu  Pro  Ser  Lys  Tyr  Val
     1220                1225                1230

Asn  Phe  Leu  Tyr  Leu  Ala  Ser  His  Tyr  Glu  Lys  Leu  Lys  Gly  Ser
1235                1240                1245

Pro  Glu  Asp  Asn  Glu  Gln  Lys  Gln  Leu  Phe  Val  Glu  Gln  His  Lys
     1250                1255                1260

His  Tyr  Leu  Asp  Glu  Ile  Ile  Glu  Gln  Ile  Ser  Glu  Phe  Ser  Lys
1265                1270                1275

Arg  Val  Ile  Leu  Ala  Asp  Ala  Asn  Leu  Asp  Lys  Val  Leu  Ser  Ala
     1280                1285                1290

Tyr  Asn  Lys  His  Arg  Asp  Lys  Pro  Ile  Arg  Glu  Gln  Ala  Glu  Asn
1295                1300                1305

Ile  Ile  His  Leu  Phe  Thr  Leu  Thr  Asn  Leu  Gly  Ala  Pro  Ala  Ala
     1310                1315                1320

Phe  Lys  Tyr  Phe  Asp  Thr  Thr  Ile  Asp  Arg  Lys  Arg  Tyr  Thr  Ser
1325                1330                1335

Thr  Lys  Glu  Val  Leu  Asp  Ala  Thr  Leu  Ile  His  Gln  Ser  Ile  Thr
     1340                1345                1350

Gly  Leu  Tyr  Glu  Thr  Arg  Ile  Asp  Leu  Ser  Gln  Leu  Gly  Gly  Asp
1355                1360                1365

<210> SEQ ID NO 10
<211> LENGTH: 23
<212> TYPE: DNA
<213> ORGANISM: Artificial sequence
<220> FEATURE:
<223> OTHER INFORMATION: DNA encoding a guide RNA

<400> SEQUENCE: 10
gggtgggggg agtttgctcc tgg                                            23

<210> SEQ ID NO 11
<211> LENGTH: 23
<212> TYPE: DNA
<213> ORGANISM: Artificial sequence
<220> FEATURE:
<223> OTHER INFORMATION: DNA encoding a guide RNA

<400> SEQUENCE: 11
gggagggtgg agtttgctcc tgg                                            23

<210> SEQ ID NO 12
<211> LENGTH: 23
<212> TYPE: DNA
<213> ORGANISM: Artificial sequence
```

```
<220> FEATURE:
<223> OTHER INFORMATION: DNA encoding a guide RNA

<400> SEQUENCE: 12
gaccccctcc accccgcctc cgg                                              23

<210> SEQ ID NO 13
<211> LENGTH: 23
<212> TYPE: DNA
<213> ORGANISM: Artificial sequence
<220> FEATURE:
<223> OTHER INFORMATION: DNA encoding a guide RNA

<400> SEQUENCE: 13
gggcccctcc accccgcctc tgg                                              23

<210> SEQ ID NO 14
<211> LENGTH: 23
<212> TYPE: DNA
<213> ORGANISM: Artificial sequence
<220> FEATURE:
<223> OTHER INFORMATION: DNA encoding a guide RNA

<400> SEQUENCE: 14
ggtgagtgag tgtgtgcgtg tgg                                              23

<210> SEQ ID NO 15
<211> LENGTH: 23
<212> TYPE: DNA
<213> ORGANISM: Artificial sequence
<220> FEATURE:
<223> OTHER INFORMATION: DNA encoding a guide RNA

<400> SEQUENCE: 15
agtgagtgag tgtgtgtgtg ggg                                              23

<210> SEQ ID NO 16
<211> LENGTH: 23
<212> TYPE: DNA
<213> ORGANISM: Artificial sequence
<220> FEATURE:
<223> OTHER INFORMATION: DNA encoding a guide RNA

<400> SEQUENCE: 16
gctgcagaag ggattccatg agg                                              23

<210> SEQ ID NO 17
<211> LENGTH: 23
<212> TYPE: DNA
<213> ORGANISM: Artificial sequence
<220> FEATURE:
<223> OTHER INFORMATION: DNA encoding a guide RNA

<400> SEQUENCE: 17
gctgcagaag ggattccaag ggg                                              23

<210> SEQ ID NO 18
<211> LENGTH: 23
<212> TYPE: DNA
<213> ORGANISM: Artificial sequence
<220> FEATURE:
<223> OTHER INFORMATION: DNA encoding a guide RNA

<400> SEQUENCE: 18
gcattttcag gaggaagcga tgg                                              23
```

```
<210> SEQ ID NO 19
<211> LENGTH: 23
<212> TYPE: DNA
<213> ORGANISM: Artificial sequence
<220> FEATURE:
<223> OTHER INFORMATION: DNA encoding a guide RNA

<400> SEQUENCE: 19
gcattttcag aaggaagcaa ggg                                              23

<210> SEQ ID NO 20
<211> LENGTH: 23
<212> TYPE: DNA
<213> ORGANISM: Artificial sequence
<220> FEATURE:
<223> OTHER INFORMATION: DNA encoding a guide RNA

<400> SEQUENCE: 20
gagtccgagc agaagaagaa ggg                                              23

<210> SEQ ID NO 21
<211> LENGTH: 23
<212> TYPE: DNA
<213> ORGANISM: Artificial sequence
<220> FEATURE:
<223> OTHER INFORMATION: DNA encoding a guide RNA

<400> SEQUENCE: 21
gagttagagc agaagaagaa agg                                              23

<210> SEQ ID NO 22
<211> LENGTH: 20
<212> TYPE: DNA
<213> ORGANISM: Artificial sequence
<220> FEATURE:
<223> OTHER INFORMATION: DNA encoding a guide RNA

<400> SEQUENCE: 22
ctgcgtgatg agctgcacgg                                                  20

<210> SEQ ID NO 23
<211> LENGTH: 18
<212> TYPE: DNA
<213> ORGANISM: Artificial sequence
<220> FEATURE:
<223> OTHER INFORMATION: DNA encoding a guide RNA

<400> SEQUENCE: 23
ggagtttgag tgaagtat                                                    18

<210> SEQ ID NO 24
<211> LENGTH: 20
<212> TYPE: DNA
<213> ORGANISM: Artificial sequence
<220> FEATURE:
<223> OTHER INFORMATION: DNA encoding a guide RNA

<400> SEQUENCE: 24
cttgccccac agggcagtaa                                                  20

<210> SEQ ID NO 25
<211> LENGTH: 20
<212> TYPE: DNA
<213> ORGANISM: Artificial sequence
<220> FEATURE:
<223> OTHER INFORMATION: DNA encoding a guide RNA
```

<400> SEQUENCE: 25
ccagaaagag agagtagcgc                                                    20

<210> SEQ ID NO 26
<211> LENGTH: 21
<212> TYPE: DNA
<213> ORGANISM: Artificial sequence
<220> FEATURE:
<223> OTHER INFORMATION: DNA encoding a guide RNA

<400> SEQUENCE: 26
aacagaagta cctgtcggcg c                                                  21

<210> SEQ ID NO 27
<211> LENGTH: 146
<212> TYPE: DNA
<213> ORGANISM: Artificial sequence
<220> FEATURE:
<223> OTHER INFORMATION: Synthetic oligonucleotide

<400> SEQUENCE: 27
acgtgatggc cagcgtggac aaccccacg tgtgccgcct gctgggcatc tgcctcacct          60
ctacagtcca actgattacc cagctcatgc ccttcggctg cctcctggac tatgtccggg        120
aacacaaaga caatattggc tcccag                                            146

<210> SEQ ID NO 28
<211> LENGTH: 140
<212> TYPE: DNA
<213> ORGANISM: Artificial sequence
<220> FEATURE:
<223> OTHER INFORMATION: Synthetic oligonucleotide

<400> SEQUENCE: 28 gcccctgtg ctcatcacgc gccccttgga ggaccagctg gtgatggtgg ggcagcgggt          60
ggagtttgcg aggtatcgga ggaggggcg caagtcaaat ggtgagttcc agaagcacgg         120
ggcatgggtg ttgggggcat                                                    140

<210> SEQ ID NO 29
<211> LENGTH: 133
<212> TYPE: DNA
<213> ORGANISM: Artificial sequence
<220> FEATURE:
<223> OTHER INFORMATION: Synthetic oligonucleotide

<400> SEQUENCE: 29
tctgacacaa ctgtgttcac tagcaacctc aaacagacac catggtgcat ctgactcctg         60
tggagaagtc tgcagttact gccctgtggg gcaaggtgaa cgtggatgaa gttggtggtg        120
aggccctggg cag                                                          133

<210> SEQ ID NO 30
<211> LENGTH: 100
<212> TYPE: DNA
<213> ORGANISM: Artificial sequence
<220> FEATURE:
<223> OTHER INFORMATION: Synthetic oligonucleotide

<400> SEQUENCE: 30
gggtaggaga gactcacgct ggatagcctc caggccagaa agagagagta gcgcgacgca         60
cagctaaggc cacggagcga gacatctcgg cccgaatgct                              100

```
<210> SEQ ID NO 31
<211> LENGTH: 169
<212> TYPE: DNA
<213> ORGANISM: Artificial sequence
<220> FEATURE:
<223> OTHER INFORMATION: Synthetic oligonucleotide

<400> SEQUENCE: 31
ggaagcgccg ggtgctcttc tcgcaggcgc aggtgtacga gctggagcga cgcttcaagc      60
aacagaagta cctgtcggcg cccgagctcg agcacctggc cagcatgatc cacctgacgc     120
ccacgcaggt caagatctgg ttccagaacc accgctacaa aatgaagcg                 169
```

NUCLEASE-MEDIATED NUCLEIC ACID MODIFICATION

This application claims priority to U.S. provisional patent application Ser. No. 62/698,376, filed Jul. 16, 2018, which is incorporated herein by reference in its entirety.

STATEMENT REGARDING FEDERALLY SPONSORED RESEARCH OR DEVELOPMENT

This invention was made with government support under GM122181 awarded by the National Institutes of Health. The government has certain rights in the invention.

FIELD

Provided herein is technology relating to molecular biological manipulation of genes and genomes and particularly, but not exclusively, to CRISPR (Clustered Regularly Interspaced Short Palindromic Repeats) methods, compositions, systems, and kits for improved genetic editing.

BACKGROUND

CRISPR/Cas9 (CRISPR associated protein 9) is widely used for gene editing. However, CRISPR and related technologies used for gene editing has a low efficiency of "knocking in" (KI) large fragment sequences (e.g., a reporter gene) at target sites. In particular, the efficiency of knock in is often below 1%. Accordingly, improved technologies are needed.

SUMMARY

Provided herein is a technology related to a modified CRISPR/Cas9 for improved integration of knock-in nucleic acid inserts at target sites. In some embodiments, the technology increases by several fold the KI efficiency of large size inserts at a range of loci in human cells (e.g., primary cells, pluripotent stem cells, and adult stem cells).

Furthermore the CRISPR technology provided herein significantly reduces off-target integration relative to conventional CRISPR approaches. e.g., using a conventional Cas9 protein. As described herein, the improved CRISPR technology finds use in broad applications related to gene editing research and therapeutics.

Accordingly, provided herein is technology related to a gene editing nuclease-BE27 fusion protein comprising a gene editing nuclease domain and a BE27 domain. In some embodiments, the gene editing nuclease domain comprises a CRISPR-associated system protein, a portion thereof, a homolog thereof, or a modified version thereof. In some embodiments, the gene editing nuclease domain comprises a Cas protein, a portion thereof, a homolog thereof, or a modified version thereof. In some embodiments, the gene editing nuclease domain comprises a Cas protein selected from the group consisting of Cas1, Cas1B, Cas2, Cas3, Cas4, Cas5, Cas6, Cas7, Cas8, Cas9, Cas10, Cas13, Csy1, Csy2, Csy3, Cse1, Cse2, Csc1, Csc2, Csa5, Csn2, Csm2, Csm3, Csm4, Csm5, Csm6, Cmr1, Cmr3, Cmr4, Cmr5, Cmr6, Csb1, Csb2, Csb3, Csx17, Csx14, Csx10, Csx16, CsaX, Csx3, Csx1, Csx15, Csf1, Csf2, Csf3, Csf4, Cpf1, C2c1, C2c2, HiFiCas9, spCas9mSA, HypaCas9 (see. e.g., Chen (2017) "Enhanced proofreading governs CRISPR-Cas9 targeting accuracy" Nature 550(7676):407-410, incorporated herein by reference), and xCas9 (see. e.g., Hu (2018) "Evolved Cas9 variants with broad PAM compatibility and high DNA specificity" Nature 556(7699):57-63, incorporated herein by reference); a portion thereof; a homolog thereof; or a modified version thereof. In some embodiments, the gene editing nuclease domain comprises a TALEN, a portion thereof, a homolog thereof, or a modified version thereof. In some embodiments, the gene editing nuclease domain comprises ZFN, a portion thereof, a homolog thereof, or a modified version thereof.

In some embodiments, the gene editing nuclease domain comprises an eSpCas9 as described in Slaymaker (2016) "Rationally engineered Cas9 nucleases with improved specificity" Science 351(6268):84-8, incorporated herein by reference.

In some embodiments, the gene editing nuclease domain comprises a SpCas9-HD1 as described in Kleinstiver (2016) "High-fidelity CRISPR-Cas9 nucleases with no detectable genome-wide off-target effects" Nature 529(7587):490-5, incorporated herein by reference.

In some embodiments, the gene editing nuclease domain comprises a "highly enhanced fidelity" nuclease variant as described in Kulcsár (2017) Genome Biology 18: 190, incorporated herein by reference.

In some embodiments, the gene editing nuclease domain comprises a HiFiCas9 as described in Vakulskas (2018) "A novel high-fidelity Cas9 delivered as a ribonucleoprotein complex enables high frequency gene editing in human haematopoietic stem and progenitor cells" Nature Medicine 24(8): 1216-1224, incorporated herein by reference.

In some embodiments, the gene editing nuclease is fused to a polypeptide that modulates its activity. For instance, in some embodiments, the gene editing nuclease is fused to Gem (e.g., hGem) (see, e.g., Gutschner (2016) "Post-translational Regulation of Cas9 during G1 Enhances Homology-Directed Repair" Cell Rep 14(6):1555-1566; and Howden (2016) "A Cas9 Variant for Efficient Generation of Indel-Free Knockin or Gene-Corrected Human Pluripotent Stem Cells" Stem Cell Reports 7(3):508-517, each of which is incorporated herein by reference), fused to CtIP (see. e.g., Charpentier (2018) "CtIP fusion to Cas9 enhances transgene integration by homology-dependent repair" Nat Comm 9(1): 1133, incorporated herein by reference), Cyclin B2 (see, e.g., Vicente (2019) "A CyclinB2-Cas9 fusion promotes the homology-directed repair of double-strand breaks" bioR$_x$iv doi.org/10.1101/555144, incorporated herein by reference), chromatin-modulating peptides (see, e.g., Ding (2019) "Improving CRISPR-Cas9 Genome Editing Efficiency by Fusion with Chromatin-Modulating Peptides" The CRISPR Journal Vol. 2, No. 1, incorporated herein by reference), RecA (see. e.g., Lin (2017) "Fusion of SpCas9 to *E. coli* Rec A protein enhances CRISPR-Cas9 mediated gene knockout in mammalian cells" J Biotechnol 247:42-49, incorporated herein by reference), or comprising an intein that provides small-molecule control of Cas9 (see, e.g., Davis (2015) "Small molecule-triggered Cas9 protein with improved genome-editing specificity" Nat Chem Biol 11(5):316-8 (incorporated herein by reference). In some embodiments, the gene editing nuclease is fused to a polypeptide that modulates its activity (e.g., as described above) and further is fused to one or more BE27 domains.

In some embodiments, the gene editing nuclease-BE27 fusion comprises one BE27 domain. In some embodiments, the gene editing nuclease-BE27 fusion comprises a plurality of BE27 domains. e.g., 1, 2, 3, 4, 5, 6, 7, 8, 9, 10, 11, 12, 13, 14, 15, 16, 17, 18, 19, 20, 21, 22, 23, 24, or 25 or more BE27 domains.

In some embodiments, the technology provides a composition comprising a gene editing nuclease-BE27 fusion protein. In some embodiments, the compositions further comprise a gRNA. In some embodiments, the compositions further comprise a donor nucleic acid. In some embodiments, the compositions further comprise a target nucleic acid. In some embodiments, the donor nucleic acid comprises 100 to 1000 bp (e.g., 100, 150, 200, 250, 300, 350, 400, 450, 500, 550, 600, 650, 700, 750, 800, 850, 900, 950, or 1000 bp). In some embodiments, the donor nucleic acid comprises 1000 to 10,000 bp (e.g., 1000, 1500, 2000, 2500, 3000, 3500, 4000, 4500, 5000, 5500, 6000, 6500, 7000, 7500, 8000, 8500, 9000, 9500, or 10,000 bp). In some embodiments, the compositions further comprise a RAD51 protein or a plurality of RAD51 proteins. In some embodiments, the compositions further comprise a knockin, e.g., comprising a sequence from the donor nucleic acid. In some embodiments, compositions comprise a nucleic acid comprising a RAD51 protein.

Related embodiments provide methods for producing a knockin in a target, nucleic acid. In some embodiments, methods comprise contacting a target nucleic acid with a gene editing nuclease-BE27 fusion protein. In some embodiments, methods comprise contacting a target nucleic acid with a ribonucleoprotein comprising a gene editing nuclease-BE27 fusion protein and a gRNA comprising a sequence complementary to the target nucleic acid. In some embodiments, methods further comprise providing a donor nucleic acid comprising a knockin sequence. In some embodiments, methods comprise introducing said ribonucleoprotein into a cell. In some embodiments, methods comprise introducing said ribonucleoprotein and said donor nucleic acid into a cell.

Related embodiments provide a kit comprising a gene editing nuclease-BE27 fusion protein.

Related embodiments provide a system comprising a gene editing nuclease-BE27 fusion protein.

Related embodiments provide use of a gene editing nuclease-BE27 fusion protein to produce a transgenic cell. In some embodiments, the technology provides use of a gene editing nuclease-BE27 fusion protein to produce a transgenic animal.

In some embodiments, the technology provides a nucleic acid encoding a gene editing nuclease-BE27 fusion protein. In some embodiments, the technology provides a vector comprising a nucleic acid encoding a gene editing nuclease-BE27 fusion protein. In some embodiments, the technology provides a cell comprising a gene editing nuclease-BE27 fusion protein. In some embodiments, the technology provides a cell comprising a nucleic acid encoding a gene editing nuclease-BE27 fusion protein. In some embodiments, the technology provides a cell expressing a gene editing nuclease-BE27 fusion protein. In some embodiments, the technology provides a cell expressing a nucleic acid encoding a gene editing nuclease-BE27 fusion protein.

Additional embodiments will be apparent to persons skilled in the relevant art based on the teachings contained herein.

BRIEF DESCRIPTION OF THE DRAWINGS

These and other features, aspects, and advantages of the present technology will become better understood with regard to the following drawings:

FIG. 9A provides gRNA sequences used for experiments testing precise genome editing (PGE) at the EGFR. Mybpc3, HBB, B2M, and NKX2.1 loci.

FIG. 9B provides donor singles-stranded oligodeoxynucleotides (ODNs) used for experiments testing precise genome editing (PGE) at the EGFR, Mybpc3, HBB, B2M, and NKX2.1 loci.

Figure 1:
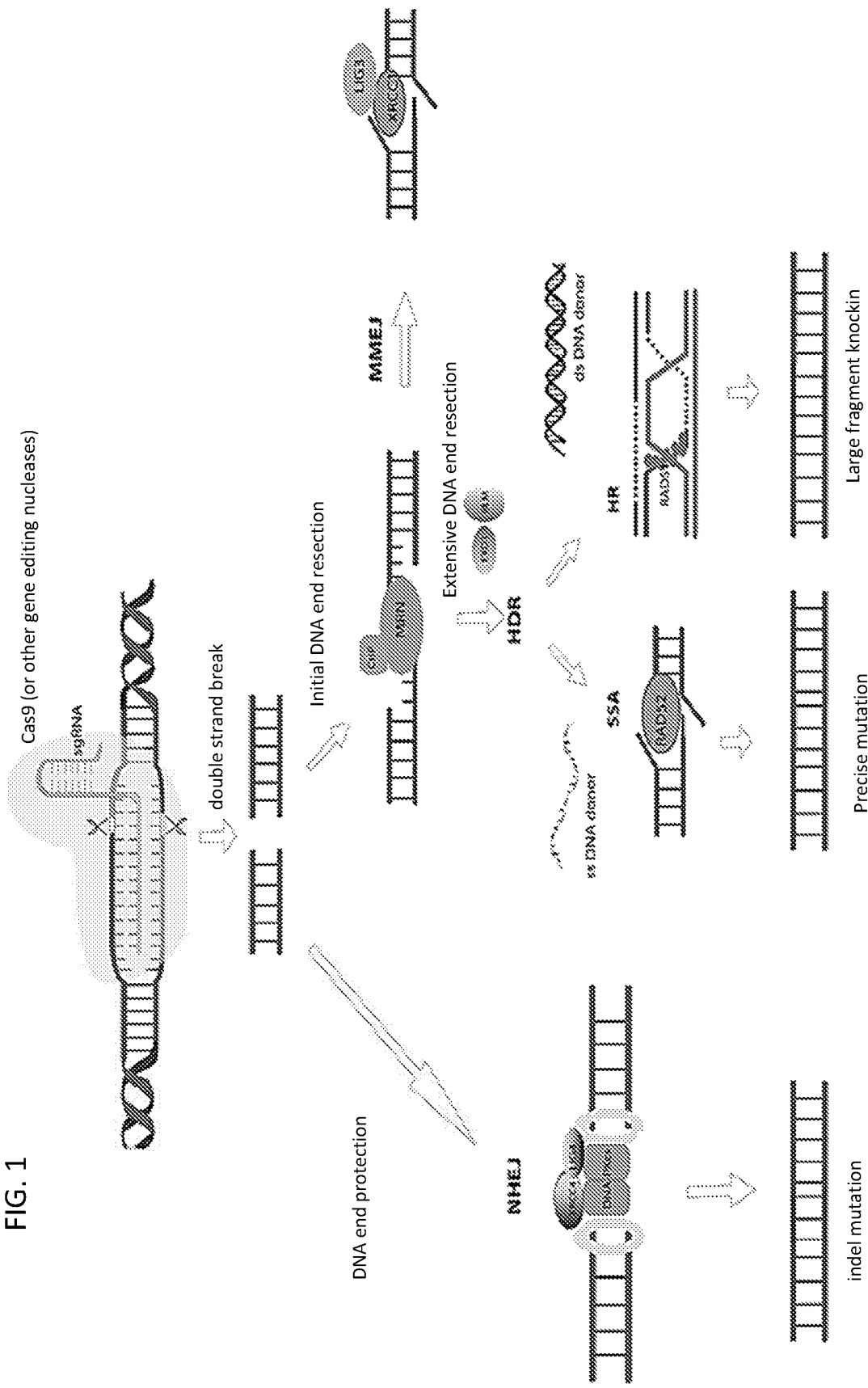
FIG. 1 is a schematic drawing showing pathways of double strand break repair in a cell. CRISPR creates double stranded breaks (DSBs) at the target locus in the genome. The majority of the DSBs are repaired by non-homologous end joining (NHEJ) mechanisms, leading to unpredictable insertions and deletions (indels). When such DSBs are repaired by the homology directed repair (HDR) pathway, provided a donor template is available, knock-in may take place. The use of a CRISPR ribonucleoprotein (RNP) and single stranded oligodeoxynucleotide enhances the precise mutation rates, e.g., to two-digit efficiencies, through the single strand annealing (SSA) pathway.

It is to be understood that the figures are not necessarily drawn to scale, nor are the objects in the figures necessarily drawn to scale in relationship to one another. The figures are depictions that are intended to bring clarity and understanding to various embodiments of apparatuses, systems, and methods disclosed herein. Wherever possible, the same reference numbers will be used throughout the drawings to refer to the same or like parts. Moreover, it should be appreciated that the drawings are not intended to limit the scope of the present teachings in any way.

DETAILED DESCRIPTION

Provided herein is a technology related to a modified CRISPR/Cas9 for improved integration of knock-in nucleic acid inserts at target sites. In some embodiments, the technology increases by several fold the KI efficiency of large size inserts at a range of loci in human cells (e.g., primary cells, pluripotent stem cells, and adult stem cells). Furthermore the CRISPR technology provided herein significantly reduces off-target integration relative to conventional CRISPR approaches, e.g., using a conventional Cas9 protein. As described herein, the improved CRISPR technology finds use in broad applications related to gene editing research and therapeutics.

In this detailed description of the various embodiments, for purposes of explanation, numerous specific details are set forth to provide a thorough understanding of the embodiments disclosed. One skilled in the art will appreciate, however, that these various embodiments may be practiced with or without these specific details. In other instances, structures and devices are shown in block diagram form. Furthermore, one skilled in the art can readily appreciate that the specific sequences in which methods are presented and performed are illustrative and it is contemplated that the sequences can be varied and still remain within the spirit and scope of the various embodiments disclosed herein.

All literature and similar materials cited in this application, including but not limited to, patents, patent applications, articles, books, treatises, and internet web pages are expressly incorporated by reference in their entirety for any purpose. Unless defined otherwise, all technical and scientific terms used herein have the same meaning as is commonly understood by one of ordinary skill in the art to which the various embodiments described herein belongs. When definitions of terms in incorporated references appear to differ from the definitions provided in the present teachings, the definition provided in the present teachings shall control. The section headings used herein are for organizational purposes only and are not to be construed as limiting the described subject matter in any way.

Definitions

To facilitate an understanding of the present technology, a number of terms and phrases are defined below. Additional definitions are set forth throughout the detailed description.

Throughout the specification and claims, the following terms take the meanings explicitly associated herein, unless the context clearly dictates otherwise. The phrase "in one embodiment" as used herein does not necessarily refer to the same embodiment, though it may. Furthermore, the phrase "in another embodiment" as used herein does not necessarily refer to a different embodiment, although it may. Thus, as described below, various embodiments of the invention may be readily combined, without departing from the scope or spirit of the invention.

In addition, as used herein, the term "or" is an inclusive "or" operator and is equivalent to the term "and/or" unless the context clearly dictates otherwise. The term "based on" is not exclusive and allows for being based on additional factors not described, unless the context clearly dictates otherwise. In addition, throughout the specification, the meaning of "a", "an", and "the" include plural references. The meaning of "in" includes "in" and "on."

As used herein, the terms "about", "approximately", "substantially", and "significantly" are understood by persons of ordinary skill in the art and will vary to some extent on the context in which they are used. If there are uses of these terms that are not clear to persons of ordinary skill in the art given the context in which they are used. "about" and "approximately" mean plus or minus less than or equal to 10% of the particular term and "substantially" and "significantly" mean plus or minus greater than 10% of the particular term.

As used herein, the suffix "-free" refers to an embodiment of the technology that omits the feature of the base root of the word to which "-free" is appended. That is, the term "X-free" as used herein means "without X", where X is a feature of the technology omitted in the "X-free" technology. For example, a "calcium-free" composition does not comprise calcium, a "sequencing-free" method does not comprise a sequencing step, etc.

As used herein, the term "gene editing nuclease-BE27 fusion" refers to a polypeptide comprising: 1) a gene editing nuclease domain (e.g., a CRISPR-associated system protein (Cas protein (e.g., a Cas9 protein or similar as described herein)), a transcription activator-like effector nuclease (TALEN), a zinc-finger nuclease (ZFN), a meganuclease, or variants or modified versions thereof); and 2) a domain comprising one or more amino acid sequences comprising exon 27 from BRCA2 (a BE27 domain; see discussion below). In some embodiments, a gene editing nuclease-BE27 comprises 1, 2, 3, 4, 5, 6, 7, 8, 9, 10, 11, 12, 13, 14, 15, 16, 17, 18, 19, 20, 21, 22, 23, 24, 25, 30, 35, 40, 45, 50, 55, 60, 65, 70, 75, 80, 85, 90, 95, 100, or more BE27 domains. In some embodiments, a ribonucleoprotein as described herein comprises a polypeptide that is a gene editing nuclease-BE27 fusion as described herein and a gRNA as described herein. In some embodiments, the gene editing nuclease-BE27 fusion comprises a gene editing nuclease that is a Cas9 or a protein having an activity similar to a Cas9 (e.g., a Cpf1 or other Cas9-like protein or Cas9 homolog as described herein) fused to one or more BE27 domains (e.g., 1, 2, 3, 4, 5, 6, 7, 8, 9, 10, 11, 12, 13, 14, 15, 16, 17, 18, 19, 20, 21, 22, 23, 24, or 25 BE27 domains).

As used herein, a "nucleic acid" or a "nucleic acid sequence" refers to a polymer or oligomer of pyrimidine and/or purine bases, preferably cytosine, thymine, and uracil, and adenine and guanine, respectively (See Albert L. Lehninger, Principles of Biochemistry, at 793-800 (Worth Pub. 1982), incorporated herein by reference). The present technology contemplates any deoxyribonucleotide, ribonucleotide, or peptide nucleic acid component, and any chemical variants thereof, such as methylated, hydroxymethylated, or glycosylated forms of these bases, and the like. The polymers or oligomers may be heterogenous or homogenous in composition, and may be isolated from naturally occurring sources or may be artificially or synthetically produced. In addition, the nucleic acids may be DNA or RNA, or a mixture thereof, and may exist permanently or transitionally in single-stranded or double-stranded form, including homoduplex, heteroduplex, and hybrid states. In some embodiments, a nucleic acid or nucleic acid sequence comprises other kinds of nucleic acid structures such as, for instance, a DNA/RNA helix, peptide nucleic acid (PNA), morpholino nucleic acid (see. e.g., Braasch and Corey, Biochemistry, 2002, 41(14), 4503-4510, incorporated herein by reference) and U.S. Pat. No. 5,034,506, incorporated herein by reference), locked nucleic acid (LNA; see Wahlestedt et. al, Proc. Natl. Acad. Sci. U.S.A., 2000, 97, 5633-5638, incorporated herein by reference), cyclohexenyl nucleic acids (see Wang. J. Am. Chem. Soc., 2000, 122, 8595-8602, incorporated herein by reference), and/or a ribozyme. Hence, the term "nucleic acid" or "nucleic acid sequence" may also encompass a chain comprising non-natural nucleotides, modified nucleotides, and/or non-nucleotide building blocks that can exhibit the same function as natural nucleotides (e.g., "nucleotide analogs"); further, the term "nucleic acid sequence" as used herein refers to an oligonucleotide, nucleotide or polynucleotide, and fragments or portions thereof, and to DNA or RNA of genomic or synthetic origin, which may be single or double-stranded, and represent the sense or antisense strand.

Furthermore, the terms "nucleic acid", "polynucleotide", "nucleotide sequence", and "oligonucleotide" are used interchangeably. They refer to a polymeric form of nucleotides of any length, either deoxyribonucleotides or ribonucleotides, or analogs thereof. Polynucleotides may have any three dimensional structure and may perform any function, known or unknown. The following are non-limiting examples of polynucleotides: coding or non-coding regions of a gene or gene fragment, loci (locus) defined from linkage analysis, exons, introns, messenger RNA (mRNA), transfer RNA, ribosomal RNA, short interfering RNA (siRNA), short-hairpin RNA (shRNA), micro-RNA (miRNA), ribozymes, cDNA, recombinant polynucleotides, branched polynucleotides, plasmids, vectors, isolated DNA of any sequence, isolated RNA of any sequence, nucleic acid probes, and primers. The term also encompasses nucleic-acid-like structures with synthetic backbones, see, e.g., Eckstein, 1991; Baserga et al., 1992; Milligan, 1993: WO 97/03211; WO 96/39154; Mata, 1997; Strauss-Soukup, 1997; and Samstag, 1996, each of which is incorporated herein by reference. A polynucleotide may comprise one or more modified nucleotides, such as methylated nucleotides and nucleotide analogs. If present, modifications to the nucleotide structure may be imparted before or after assembly of the polymer. The sequence of nucleotides may be interrupted by non-nucleotide components. A polynucleotide may be further modified after polymerization, such as by conjugation with a labeling component.

The term "nucleotide analog" as used herein refers to modified or non-naturally occurring nucleotides including but not limited to analogs that have altered stacking interactions such as 7-deaza purines (i.e., 7-deaza-dATP and 7-deaza-dGTP); base analogs with alternative hydrogen bonding configurations (e.g., such as Iso-C and Iso-G and other non-standard base pairs described in U.S. Pat. No. 6,001,983 to S. Benner, herein incorporated by reference); non-hydrogen bonding analogs (e.g., non-polar, aromatic nucleoside analogs such as 2,4-difluorotoluene, described by B. A. Schweitzer and E. T. Kool. J. Org. Chem., 1994, 59, 7238-7242. B. A. Schweitzer and E. T. Kool. J. Am. Chem. Soc., 1995, 117, 1863-1872; each of which is herein incorporated by reference); "universal" bases such as 5-nitroindole and 3-nitropyrrole; and universal purines and pyrimidines (such as "K" and "P" nucleotides, respectively; P. Kong, et al., Nucleic Acids Res., 1989, 17, 10373-10383, P. Kong et al., Nucleic Acids Res., 1992, 20, 5149-5152, each of which is incorporated herein by reference). Nucleotide analogs include nucleotides having modification on the sugar moiety, such as dideoxy nucleotides and 2'-O-methyl nucleotides. Nucleotide analogs include modified forms of deoxyribonucleotides as well as ribonucleotides.

"Peptide nucleic acid" means a DNA mimic that incorporates a peptide-like polyamide backbone.

As used herein, the term "% sequence identity" refers to the percentage of nucleotides or nucleotide analogs in a nucleic acid sequence that is identical with the corresponding nucleotides in a reference sequence after aligning the two sequences and introducing gaps, if necessary, to achieve the maximum percent identity. Hence, in case a nucleic acid according to the technology is longer than a reference sequence, additional nucleotides in the nucleic acid, that do not align with the reference sequence, are not taken into account for determining sequence identity. Methods and computer programs for alignment are well known in the art, including BLAST. Align 2, and FAST-A.

The term "homology" and "homologous" refers to a degree of identity. There may be partial homology or complete homology. A partially homologous sequence is one that is less than 100% identical to another sequence.

The term "sequence variation" as used herein refers to a difference or multiple differences in nucleic acid sequence between two nucleic acids. For example, a wild-type structural gene and a mutant form of this wild-type structural gene may vary in sequence by the presence of one or more single base substitutions or by deletions and/or insertions of one or more nucleotides. These two forms of the structural gene are said to vary in sequence from one another. A second mutant form of the structural gene may exist. This second mutant form is said to vary in sequence from both the wild-type gene and the first mutant form of the gene.

As used herein, the terms "complementary", "hybridizable", or "complementarity" are used in reference to polynucleotides (e.g., a sequence of nucleotides such as an oligonucleotide or a target nucleic acid) related by the base-pairing rules. For example, for the sequence "5'-A-G-T-3'" is complementary to the sequence "3'-T-C-A-5'." Complementarity may be "partial," in which only some of the nucleic acid bases are matched according to the base pairing rules. Or, there may be "complete" or "total" complementarity between the nucleic acids. The degree of complementarity between nucleic acid strands has significant effects on the efficiency and strength of hybridization between nucleic acid strands. This is of particular importance in amplification reactions, as well as detection methods that depend upon binding between nucleic acids. Either term may also be used in reference to individual nucleotides, especially within the context of polynucleotides. For example, a particular nucleotide within an oligonucleotide may be noted for its complementarity, or lack thereof, to a nucleotide within another nucleic acid strand, in contrast or comparison to the complementarity between the rest of the oligonucleotide and the nucleic acid strand.

In some contexts, the term "complementarity" and related terms (e.g., "complementary". "complement") refers to the nucleotides of a nucleic acid sequence that can bind to another nucleic acid sequence through hydrogen bonds, e.g., nucleotides that are capable of base pairing, e.g., by Watson-Crick base pairing or other base pairing. Nucleotides that can form base pairs, e.g., nucleotides that are complementary to one another, are the pairs: cytosine and guanine, thymine and adenine, adenine and uracil, and guanine and uracil. The percentage complementarity need not be calculated over the entire length of a nucleic acid sequence. The percentage of complementarity may be limited to a specific region of which the nucleic acid sequences that are base-paired, e.g., starting from a first base-paired nucleotide and ending at a last base-paired nucleotide. The complement of a nucleic acid sequence as used herein refers to an oligonucleotide which, when aligned with the nucleic acid sequence such that the 5' end of one sequence is paired with the 3' end of the other, is in "antiparallel association." Certain bases not commonly found in natural nucleic acids may be included in the nucleic acids of the present invention and include, for example, inosine and 7-deazaguanine.

Complementarity need not be perfect; stable duplexes may contain mismatched base pairs or unmatched bases. Those skilled in the art of nucleic acid technology can determine duplex stability empirically considering a number of variables including, for example, the length of the oligonucleotide, base composition and sequence of the oligonucleotide, ionic strength and incidence of mismatched base pairs.

It is understood in the art that the sequence of a polynucleotide need not be 100% complementary to that of its target nucleic acid to be hybridizable or specifically hybridizable. Moreover, a polynucleotide may hybridize over one or more segments such that intervening or adjacent segments are not involved in the hybridization event (e.g., a loop structure or hairpin structure). A polynucleotide can comprise at least 70%, at least 80%, at least 90%, at least 95%, at least 99%, or 100% sequence complementarity to a target region within the target nucleic acid sequence to which they are targeted. For example, a nucleic acid in which 18 of 20 nucleotides of the nucleic acid are complementary to a target region, and would therefore specifically hybridize, would represent 90 percent complementarity. In this example, the remaining non-complementary nucleotides may be clustered or interspersed with complementary nucleotides and need not be contiguous to each other or to complementary nucleotides. Percent complementarity between particular segments of nucleic acid sequences within nucleic acids can be determined routinely using BLAST programs (basic local alignment search tools) and PowerBLAST programs known in the art (Altschul et al., J. Mol. Biol., 1990, 215, 403-410; Zhang and Madden, Genome Res., 1997, 7, 649-656, each of which is incorporated herein by reference) or by using the Gap program (Wisconsin Sequence Analysis Package, Version 8 for Unix. Genetics Computer Group, University Research Park. Madison Wis.), using default settings, which uses the algorithm of Smith and Waterman (Adv. Appl. Math., 1981, 2, 482-489, incorporated herein by reference).

Thus, in some embodiments, "complementary" refers to a first nucleobase sequence that is at least 60%, 65%, 70%, 75%, 80%, 85%, 90%, 95%, 97%, 98%, or 99% identical to the complement of a second nucleobase sequence over a region of 8, 9, 10, 11, 12, 13, 14, 15, 16, 17, 18, 19, 20, 21, 22, 23, 24, 25, 30, 35, 40, 45, 50, 55, 60, 65, 70, 75, 80, 85, 90, 95, 100, or more nucleobases, or that the two sequences hybridize under stringent hybridization conditions. "Fully complementary" means each nucleobase of a first nucleic acid is capable of pairing with each nucleobase at a corresponding position in a second nucleic acid. For example, in certain embodiments, an oligonucleotide wherein each nucleobase has complementarity to a nucleic acid has a nucleobase sequence that is identical to the complement of the nucleic acid over a region of 8, 9, 10, 11, 12, 13, 14, 15, 16, 17, 18, 19, 20, 21, 22, 23, 24, 25, 30, 35, 40, 45, 50, 55, 60, 65, 70, 75, 80, 85, 90, 95, 100, or more nucleobases.

"Mismatch" means a nucleobase of a first nucleic acid that is not capable of pairing with a nucleobase at a corresponding position of a second nucleic acid.

As used herein, the term "hybridization" is used in reference to the pairing of complementary nucleic acids. Hybridization and the strength of hybridization (i.e., the strength of the association between the nucleic acids) is influenced by such factors as the degree of complementary between the nucleic acids, stringency of the conditions involved, and the Tm of the formed hybrid. "Hybridization" methods involve the annealing of one nucleic acid to another, complementary nucleic acid, e.g., a nucleic acid having a complementary nucleotide sequence. The ability of two polymers of nucleic acid containing complementary sequences to find each other and "anneal" or "hybridize" through base pairing interaction is a well-recognized phenomenon. The initial observations of the "hybridization" process by Marmur and Lane, Proc. Natl. Acad. Sci. USA 46:453 (1960) and Doty et al., Proc. Natl. Acad. Sci. USA 46:461 (1960), each of which is incorporated herein by reference, have been followed by the refinement of this process into an essential tool of modern biology. For example, hybridization and washing conditions are now well known and exemplified in Sambrook, J., Fritsch. E. F. and Maniatis, T. Molecular Cloning: A Laboratory Manual. Second Edition, Cold Spring Harbor Laboratory Press. Cold Spring Harbor (1989), particularly Chapter 11 and Table 11.1 therein; and Sambrook, J. and Russell, W., Molecular Cloning: A Laboratory Manual, Third Edition, Cold Spring Harbor Laboratory Press, Cold Spring Harbor (2001), each of which is incorporated herein by reference. The conditions of temperature and ionic strength determine the "stringency" of the hybridization.

As used herein, a "double-stranded nucleic acid" may be a portion of a nucleic acid, a region of a longer nucleic acid, or an entire nucleic acid. A "double-stranded nucleic acid" may be, e.g., without limitation, a double-stranded DNA, a double-stranded RNA, a double-stranded DNA/RNA hybrid, etc. A single-stranded nucleic acid having secondary structure (e.g., base-paired secondary structure) and/or higher order structure (e.g., a stem-loop structure) comprises a "double-stranded nucleic acid". For example, triplex structures are considered to be "double-stranded". In some embodiments, any base-paired nucleic acid is a "double-stranded nucleic acid".

As used herein, the term "genomic locus" or "locus" (plural "loci") is the specific location of a gene or DNA sequence on a chromosome.

The term "gene" refers to a DNA sequence that comprises control and coding sequences necessary for the production of an RNA having a non-coding function (e.g., a ribosomal or transfer RNA), a polypeptide, or a precursor. The RNA or polypeptide can be encoded by a full length coding sequence or by any portion of the coding sequence so long as the desired activity or function is retained. Thus, a "gene" refers to a DNA or RNA, or portion thereof, that encodes a polypeptide or an RNA chain that has functional role to play in an organism. For the purpose of this invention it may be considered that genes include regions that regulate the production of the gene product, whether or not such regulatory sequences are adjacent to coding and/or transcribed sequences. Accordingly, a gene includes, but is not necessarily limited to, promoter sequences, terminators, translational regulatory sequences such as ribosome binding sites and internal ribosome entry sites, enhancers, silencers, insulators, boundary elements, replication origins, matrix attachment sites, and locus control regions.

The term "wild-type" refers to a gene or a gene product that has the characteristics of that gene or gene product when isolated from a naturally occurring source. A wild-type gene is that which is most frequently observed in a population and is thus arbitrarily designated the "normal" or "wild-type" form of the gene. In contrast, the term "modified," "mutant," or "polymorphic" refers to a gene or gene product that displays modifications in sequence and or functional properties (i.e., altered characteristics) when compared to the wild-type gene or gene product. It is noted that naturally-occurring mutants can be isolated; these are identified by the fact that they have altered characteristics when compared to the wild-type gene or gene product.

As used herein, the term "functional derivative" of a polypeptide is a compound having a qualitative biological property in common with said polypeptide. "Functional derivatives" include, but are not limited to, fragments of polypeptide and derivatives of a polypeptide and its fragments, provided that they have a biological activity in common with a corresponding polypeptide. The term "derivative" encompasses both amino acid sequence variants of polypeptide, covalent modifications, and fusions thereof. A "fusion" polypeptide is a polypeptide comprising a polypeptide or portion (e.g., one or more domains) thereof fused or bonded to another heterologous polypeptide.

As used herein the term "variant" should be taken to mean the exhibition of qualities that have a pattern that deviates from what occurs in nature.

The terms "non-naturally occurring" or "engineered" are used interchangeably and indicate the involvement of the hand of man. The terms, when referring to nucleic acid molecules or polypeptides mean that the nucleic acid molecule or the polypeptide is at least substantially free from at least one other component with which they are naturally associated in nature and as found in nature.

As used herein, the term "nuclease-deficient" refers to a protein comprising reduced nuclease activity, minimized nuclease activity (e.g., a nickase), undetectable nuclease activity, and/or having no nuclease activity, e.g., as a result of amino acid substitutions that reduce, minimize, and/or eliminate the nuclease activity of a protein. In some embodiments, a nuclease-deficient protein is described as a "dead" protein.

The term "oligonucleotide" as used herein is defined as a molecule comprising two or more deoxyribonucleotides or ribonucleotides, preferably at least 5 nucleotides, more preferably at least about 10 to 15 nucleotides and more preferably at least about 15 to 50 nucleotides (e.g., 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, or 50 or more nucleotides). The exact size will depend on many factors, which in turn depend on the ultimate function or use of the oligonucleotide. The oligonucleotide may be generated in any manner, including chemical synthesis, DNA replication, reverse transcription, PCR, or a combination thereof.

Because mononucleotides are reacted to make oligonucleotides in a manner such that the 5' phosphate of one mononucleotide pentose ring is attached to the 3' oxygen of its neighbor in one direction via a phosphodiester linkage, an end of an oligonucleotide is referred to as the "5' end" if its 5' phosphate is not linked to the 3' oxygen of a mononucleotide pentose ring and as the "3' end" if its 3' oxygen is not linked to a 5' phosphate of a subsequent mononucleotide pentose ring. As used herein, a nucleic acid sequence, even if internal to a larger oligonucleotide, also may be said to have 5' and 3' ends. A first region along a nucleic acid strand is said to be upstream of another region if the 3' end of the first region is before the 5' end of the second region when moving along a strand of nucleic acid in a 5' to 3' direction.

When two different, non-overlapping oligonucleotides anneal to different regions of the same linear complementary nucleic acid sequence, and the 3' end of one oligonucleotide points towards the 5' end of the other, the former may be called the "upstream" oligonucleotide and the latter the "downstream" oligonucleotide. Similarly, when two overlapping oligonucleotides are hybridized to the same linear complementary nucleic acid sequence, with the first oligonucleotide positioned such that its 5' end is upstream of the 5' end of the second oligonucleotide, and the 3' end of the first oligonucleotide is upstream of the 3' end of the second oligonucleotide, the first oligonucleotide may be called the "upstream" oligonucleotide and the second oligonucleotide may be called the "downstream" oligonucleotide.

The terms "peptide" and "polypeptide" and "protein" are used interchangeably herein, and refer to a polymeric form of amino acids of any length, which can include coded and non-coded amino acids, chemically or biochemically modified or derivatized amino acids, and polypeptides having modified peptide backbones.

"Binding" as used herein (e.g., with reference to an RNA-binding domain of a polypeptide) refers to a non-covalent interaction between macromolecules (e.g., between a protein and a nucleic acid). While in a state of non-covalent interaction, the macromolecules are said to be "associated" or "interacting" or "binding" (e.g., when a molecule X is said to interact with a molecule Y, it is meant the molecule X binds to molecule Y in a non-covalent manner). Not all components of a binding interaction need be sequence-specific (e.g., contacts with phosphate residues in a DNA backbone), but some portions of a binding interaction may be sequence specific. Binding interactions are generally characterized by a dissociation constant (Kd) of less than $10^{-6}$ M, less than $10^{-7}$ M, less than $10^{-8}$ M, less than $10^{-9}$ M, less than $10^{-10}$ M, less than $10^{-1}$ M, less than $10^{-12}$ M, less than $10^{-13}$ M, less than $10^{-14}$ M, or less than $10^{-15}$ M. "Affinity" refers to the strength of binding, increased binding affinity being correlated with a lower Kd.

By "binding domain" it is meant a protein domain that is able to bind non-covalently to another molecule. A binding domain can bind to, for example, a DNA molecule (a DNA-binding protein), an RNA molecule (an RNA-binding protein) and/or a protein molecule (a proteinbinding protein). In the case of a protein domain-binding protein, it can bind to itself (to form homodimers, homotrimers, etc.) and/or it can bind to one or more molecules of a different protein or proteins.

As used herein, the term "ribonucleoprotein", abbreviated "RNP" refers to a multimolecular complex comprising a polypeptide (e.g., a gene editing nuclease-BE27 fusion (e.g., a Cas9 or Cas9-BE27 fusion protein, or a protein having an activity similar to a Cas9 or a Cas9-BE27 fusion protein (e.g., a Cpf1, Cpf1-BE27 fusion protein, or other Cas9-like protein. Cas9 homolog, and/or BE27 fusion thereof))) and a ribonucleic acid (e.g., a gRNA (e.g., sgRNA, a dgRNA)). In some embodiments, the polypeptide and ribonucleic acid are bound by a non-covalent interaction.

The term "conservative amino acid substitution" refers to the interchangeability in proteins of amino acid residues having similar side chains. For example, a group of amino acids having aliphatic side chains consists of glycine, alanine, valine, leucine, and isoleucine; a group of amino acids having aliphatic-hydroxyl side chains consists of serine and threonine; a group of amino acids having amide containing side chains consisting of asparagine and glutamine; a group of amino acids having aromatic side chains consists of phenylalanine, tyrosine, and tryptophan; a group of amino acids having basic side chains consists of lysine, arginine, and histidine; a group of amino acids having acidic side chains consists of glutamate and aspartate; and a group of amino acids having sulfur containing side chains consists of cysteine and methionine. Exemplary conservative amino acid substitution groups are: valine-leucine/isoleucine, phenylalanine-tyrosine, lysine-arginine, alanine-valine, and asparagine-glutamine.

"Recombinant," as used herein, means that a particular nucleic acid (DNA or RNA) is the product of various combinations of cloning, restriction, polymerase chain reaction (PCR), and/or ligation steps resulting in a construct having a structural coding or non-coding sequence distinguishable from endogenous nucleic acids found in natural systems. DNA sequences encoding polypeptides can be assembled from cDNA fragments or from a series of synthetic oligonucleotides, to provide a synthetic nucleic acid which is capable of being expressed from a recombinant transcriptional unit contained in a cell or in a cell-free transcription and translation system. Genomic DNA comprising the relevant sequences can also be used in the formation of a recombinant gene or transcriptional unit. Sequences of non-translated DNA may be present 5' or 3' from the open reading frame, where such sequences do not interfere with manipulation or expression of the coding regions, and may indeed act to modulate production of a desired product by various mechanisms). Alternatively, DNA sequences encoding RNA (e.g., DNA-targeting RNA) that is not translated may also be considered recombinant. Thus, e.g., the term "recombinant" nucleic acid refers to one which is not naturally occurring, e.g., is made by the artificial combination of two otherwise separated segments of sequence through human intervention. This artificial combination is often accomplished by either chemical synthesis means, or by the artificial manipulation of isolated segments of nucleic acids, e.g., by genetic engineering techniques. Such is usually done to replace a codon with a codon encoding the same amino acid, a conservative amino acid, or a non-conservative amino acid. Alternatively, it is performed to join together nucleic acid segments of desired functions to generate a desired combination of functions. This artificial combination is often accomplished by either chemical synthesis means, or by the artificial manipulation of isolated segments of nucleic acids, e.g., by genetic engineering techniques. When a recombinant polynucleotide encodes a polypeptide, the sequence of the encoded polypeptide can be naturally occurring ("wild type") or can be a variant (e.g., a mutant) of the naturally occurring sequence. Thus, the term "recombinant" polypeptide does not necessarily refer to a polypeptide whose sequence does not naturally occur. Instead, a "recombinant" polypeptide is encoded by a recombinant DNA sequence, but the sequence of the polypeptide can be naturally occurring ("wild type") or non-naturally occurring (e.g., a variant, a mutant, etc.). Thus, a "recombinant" polypeptide is the result of human intervention, but may be a naturally occurring amino acid sequence.

A "vector" or "expression vector" is a replicon, such as plasmid, phage, virus, or cosmid, to which another DNA segment. e.g., an "insert", may be attached so as to bring about the replication of the attached segment in a cell.

A cell has been "genetically modified" or "transformed" or "transfected" by exogenous DNA. e.g. a recombinant expression vector, when such DNA has been introduced inside the cell. The presence of the exogenous DNA results in permanent or transient genetic change. The transforming DNA may or may not be integrated (covalently linked) into the genome of the cell. In prokaryotes, yeast, and mammalian cells for example, the transforming DNA may be maintained on an episomal element such as a plasmid. With respect to eukaryotic cells, a stably transformed cell is one in which the transforming DNA has become integrated into a chromosome so that it is inherited by daughter cells through chromosome replication. This stability is demonstrated by the ability of the eukaryotic cell to establish cell lines or clones that comprise a population of daughter cells containing the transforming DNA. A "clone" is a population of cells derived from a single cell or common ancestor by mitosis. A "cell line" is a clone of a primary cell that is capable of stable growth in vitro for many generations.

Suitable methods of genetic modification (also referred to as "transformation") include e.g., viral or bacteriophage infection, transfection, conjugation, protoplast fusion, lipofection, electroporation, calcium phosphate precipitation, polyethyleneimine (PEI)-mediated transfection, DEAE-dextran mediated transfection, liposome-mediated transfection, particle gun technology, calcium phosphate precipitation, direct micro injection, nanoparticle-mediated nucleic acid delivery (see. e.g., Panyam and Labhasetwar (2012). Advanced Drug Delivery Reviews, 64 (supplement): 61-71, incorporated herein by reference). The choice of method of genetic modification is generally dependent on the type of cell being transformed and the circumstances under which the transformation is taking place (e.g., in vitro, ex vivo, or in vivo). A general discussion of these methods can be found in Ausubel, et al., Short Protocols in Molecular Biology, 3rd ed., Wiley & Sons, 1995, incorporated herein by reference.

A "target nucleic acid" (e.g., a "target DNA") as used herein is a polynucleotide (nucleic acid, gene, chromosome, genome, etc.) that comprises a "target site" or "target sequence." The terms "target site" or "target sequence" are used interchangeably herein to refer to a nucleic acid sequence present in a target DNA to which a DNA-targeting segment of a DNA-targeting RNA will bind, provided sufficient conditions for binding exist. Suitable DNA/RNA binding conditions include physiological conditions normally present in a cell. Other suitable DNA/RNA binding conditions (e.g., conditions in a cell-free system) are known in the art; see, e.g., Sambrook, referenced herein and incorporated by reference. The strand of the target DNA that is complementary to and hybridizes with the DNA-targeting RNA is referred to as the "complementary strand" and the strand of the target DNA that is complementary to the "complementary strand" (and is therefore not complementary to the DNA-targeting RNA) is referred to as the "noncomplementary strand" or "non-complementary strand".

The RNA molecule that binds to the polypeptide in the RNP and targets the polypeptide to a specific location within the target DNA is referred to herein as the "DNA targeting RNA" or "DNA-targeting RNA polynucleotide" (also referred to herein as a "guide RNA" or "gRNA"). A DNA-targeting RNA comprises two segments, a "DNA-targeting segment" and a "protein-binding segment." In some embodiments, the gRNA comprises two RNAs (e.g., a dgRNA, e.g., a crRNA and a tracrRNA) and in some embodiments the gRNA comprises one RNA (e.g., a sgRNA).

By "segment" it is meant a segment or section or portion or region of a molecule, e.g., a contiguous segment of nucleotides in an RNA. DNA, or protein. A segment can also mean a segment or section or portion or region of a complex such that a segment may comprise regions of more than one molecule. For example, In some embodiments the protein-binding segment (described below) of a DNA targeting RNA is one RNA molecule and the protein-binding segment therefore comprises a region of that RNA molecule. In other cases, the protein-binding segment (described below) of a DNA-targeting RNA comprises two separate molecules that are hybridized along a region of complementarity. As an illustrative, non-limiting example, a protein-binding segment of a DNA targeting RNA that comprises two separate molecules can comprise (i) base pairs 40-75 of a first RNA molecule that is 100 base pairs in length; and (ii) base pairs 10-25 of a second RNA molecule that is 50 base pairs in length. The definition of "segment," unless otherwise specifically defined in a particular context, is not limited to a specific number of total base pairs, is not limited to any particular number of base pairs from a given RNA molecule, is not limited to a particular number of separate molecules within a complex, and may include regions of RNA molecules that are of any total length and may or may not include regions with complementarity to other molecules.

The DNA-targeting segment (or "DNA-targeting sequence") comprises a nucleotide sequence that is complementary to a specific sequence within a target DNA (the complementary strand of the target DNA). The protein-binding segment (or "protein-binding sequence") interacts with a polypeptide of the RNP. The protein-binding segment of a DNA-targeting RNA comprises two complementary segments of nucleotides that hybridize to one another to form a double stranded RNA duplex (dsRNA duplex).

A DNA-targeting RNA and a polypeptide form a RNP complex (e.g., bind via non-covalent interactions). The DNA-targeting RNA provides target specificity to the RNP complex by comprising a nucleotide sequence that is complementary to a sequence of a target DNA. The polypeptide of the RNP complex provides site-specific binding and, in some embodiments, a nuclease activity (e.g., for genome editing (e.g., by knockout, knockin, or other genome and/or genetic modification)). In other words, the polypeptide of the RNP is guided to a target DNA sequence (e.g., a target sequence in a chromosomal nucleic acid; a target sequence in an extrachromosomal nucleic acid (e.g., an episomal nucleic acid, a minicircle, etc.); a target sequence in a mitochondrial nucleic acid; a target sequence in a chloroplast nucleic acid; a target sequence in a plasmid; etc.) by virtue of its association with the protein-binding segment of the DNA-targeting RNA.

In some embodiments, a DNA-targeting RNA comprises two separate RNA molecules (e.g., two RNA polynucleotides, e.g., an "activator-RNA" and a "targeter-RNA") and is referred to herein as a "double-molecule DNA-targeting RNA" or a "two-molecule DNA-targeting RNA" or a "double guide RNA" or a "dgRNA". In other embodiments, the DNA-targeting RNA is a single RNA molecule (e.g., a single RNA polynucleotide) and is referred to herein as a "single-molecule DNA-targeting RNA," a "single guide RNA," or an "sgRNA." The term "DNA-targeting RNA" or "guide RNA" or "gRNA" is inclusive, referring both to double-molecule DNA-targeting RNAs (dgRNAs) and to single-molecule DNA-targeting RNAs (sgRNAs).

An exemplary two-molecule DNA-targeting RNA comprises a crRNA-like ("CRISPR RNA" or "targeter-RNA" or "crRNA" or "crRNA repeat") molecule and a corresponding tracrRNA-like ("trans-acting CRISPR RNA" or "activator-RNA" or "tracrRNA") molecule. A crRNA-like molecule (targeter-RNA) comprises both the DNA-targeting segment (single stranded) of the DNA-targeting RNA and a region ("duplex-forming segment") that forms one half of the dsRNA duplex of the protein-binding segment of the DNA-targeting RNA. A corresponding tracrRNA-like molecule (activator-RNA) comprises a region (duplex-forming segment) that forms the other half of the dsRNA duplex of the protein-binding segment of the DNA-targeting RNA. In other words, a portion of the crRNA-like molecule is complementary to and hybridizes with a portion of a tracrRNA-like molecule to form the dsRNA duplex of the protein-binding domain of the DNA-targeting RNA. As such, each crRNA-like molecule can be said to have a corresponding tracrRNA-like molecule. The crRNA-like molecule additionally provides the single stranded DNA-targeting segment.

Thus, a crRNA-like molecule (e.g., a crRNA) and a tracrRNA-like molecule (e.g., a tracrRNA) hybridize (as a corresponding pair) to form a DNA-targeting RNA. The exact sequence of a given crRNA or tracrRNA molecule is characteristic of the species in which the RNA molecules are found. Various crRNAs and tracrRNAs are known in the art. A subject double molecule DNA-targeting RNA (dgRNA) can comprise any corresponding crRNA and tracrRNA pair. A subject double-molecule DNA-targeting RNA (sgRNA) can comprise any corresponding crRNA and tracrRNA pair.

The term "activator-RNA" is used herein to mean a tracrRNA-like molecule of a double molecule DNA-targeting RNA (e.g., a tracrRNA). The term "targeter-RNA" is used herein to mean a crRNA-like molecule of a double-molecule DNA-targeting RNA (e.g., a crRNA). The term "duplex-forming segment" is used herein to mean the segment of an activator-RNA or a targeter-RNA that contributes to the formation of the dsRNA duplex by hybridizing to a segment of a corresponding activator-RNA or targeter-RNA molecule. In other words, an activator-RNA comprises a duplex-forming segment that is complementary to the duplex-forming segment of the corresponding targeter-RNA. As such, an activator-RNA comprises a duplex-forming segment while a targeter-RNA comprises both a duplex-forming segment and the DNA-targeting segment of the DNA-targeting RNA. Therefore, a subject double-molecule DNA-targeting RNA can be comprised of any corresponding activator-RNA and targeter-RNA pair.

As used herein. "CRISPR system" refers collectively to transcripts and other elements involved in the expression of and/or directing the activity of CRISPR-associated ("Cas") genes, including sequences encoding a Cas gene, dCas gene, Cas homolog, and/or Cpf1 gene; a tracr (trans-activating CRISPR) sequence (e.g., tracrRNA or an active partial tracrRNA); a cr (CRISPR) sequence (e.g., crRNA or an active partial crRNA); and/or other sequences and transcripts from a CRISPR locus. In some embodiments of the technology, the terms "guide sequence" and "guide RNA" (gRNA) are used interchangeably. In some embodiments, one or more elements of a CRISPR system is derived from a type I, type II, or type III CRISPR system. In some embodiments, one or more elements of a CRISPR system is derived from a particular organism comprising an endogenous CRISPR system, such as *Streptococcus pyogenes*. In general, a CRISPR system is characterized by elements that promote the formation of a CRISPR RNP complex (e.g., in vitro or in vivo) and direct it to the site of a target sequence in a cell (e.g., after introduction of the RNP).

As used herein, the terms "subject" and "patient" refer to any organisms including plants, microorganisms, and animals (e.g., mammals such as dogs, cats, livestock, and humans).

The terms "treatment", "treating", and the like are used herein to generally mean obtaining a desired pharmacologic and/or physiologic effect. The effect may be prophylactic in terms of completely or partially preventing a disease or symptom thereof and/or may be therapeutic in terms of a partial or complete cure for a disease and/or adverse effect attributable to the disease. "Treatment" as used herein covers any treatment of a disease or symptom in a mammal, and includes: (a) preventing the disease or symptom from occurring in a subject which may be predisposed to acquiring the disease or symptom but has not yet been diagnosed as having it; (b) inhibiting the disease or symptom, e.g., arresting its development; or (c) relieving the disease. e.g., causing regression of the disease. The therapeutic agent may be administered before, during or after the onset of disease or injury. The treatment of ongoing disease, where the treatment stabilizes or reduces the undesirable clinical symptoms of the patient, is of particular interest. Such treatment is desirably performed prior to complete loss of function in the affected tissues. The subject therapy will desirably be administered during the symptomatic stage of the disease, and In some embodiments after the symptomatic stage of the disease The term "sample" in the present specification and claims is used in its broadest sense. On the one hand it is meant to include a specimen or culture (e.g., microbiological cultures). On the other hand, it is meant to include both biological and environmental samples. A sample may include a specimen of synthetic origin.

As used herein, a "biological sample" refers to a sample of biological tissue or fluid. For instance, a biological sample may be a sample obtained from an animal (including a human); a fluid, solid, or tissue sample; as well as liquid and solid food and feed products and ingredients such as dairy items, vegetables, meat and meat by-products, and waste. Biological samples may be obtained from all of the various families of domestic animals, as well as feral or wild animals, including, but not limited to, such animals as ungulates, bear, fish, lagomorphs, rodents, etc. Examples of biological samples include sections of tissues, blood, blood fractions, plasma, serum, urine, or samples from other peripheral sources or cell cultures, cell colonies, single cells, or a collection of single cells. Furthermore, a biological sample includes pools or mixtures of the above mentioned samples. A biological sample may be provided by removing a sample of cells from a subject, but can also be provided by using a previously isolated sample. For example, a tissue sample can be removed from a subject suspected of having a disease by conventional biopsy techniques. In some embodiments, a blood sample is taken from a subject. A biological sample from a patient means a sample from a subject suspected to be affected by a disease.

Environmental samples include environmental material such as surface matter, soil, water, and industrial samples, as well as samples obtained from food and dairy processing instruments, apparatus, equipment, utensils, disposable and non-disposable items. These examples are not to be construed as limiting the sample types applicable to the present invention.

The term "label" as used herein refers to any atom or molecule that can be used to provide a detectable (preferably quantifiable) effect, and that can be attached to a nucleic acid or protein. Labels include, but are not limited to, dyes (e.g., fluorescent dyes or moities); radiolabels such as $^{32}P$; binding moieties such as biotin; haptens such as digoxgenin; luminogenic, phosphorescent, or fluorogenic moieties; mass tags; and fluorescent dyes alone or in combination with moieties that can suppress or shift emission spectra by fluorescence resonance energy transfer (FRET). Labels may provide signals detectable by fluorescence, radioactivity, colorimetry, gravimetry, X-ray diffraction or absorption, magnetism, enzymatic activity, characteristics of mass or behavior affected by mass (e.g., MALDI time-of-flight mass spectrometry; fluorescence polarization), and the like. A label may be a charged moiety (positive or negative charge) or, alternatively, may be charge neutral. Labels can include or consist of nucleic acid or protein sequence, so long as the sequence comprising the label is detectable.

As used herein, "moiety" refers to one of two or more parts into which something may be divided, such as, for example, the various parts of an oligonucleotide, a molecule, a chemical group, a domain, a probe, etc.

As used herein, a "stem-loop structure" refers to a nucleic acid having a secondary structure that includes a region of nucleotides that are known or predicted to form a double strand (stem portion) that is linked on one side to a region of predominantly single-stranded nucleotides (loop portion). The terms "hairpin" and "fold-back" structures are also used herein to refer to stem-loop structures. Such structures are well known in the art and these terms are used consistently with their known meanings in the art. As is known in the art, a stem-loop structure does not require exact basepairing. Thus, the stem may include one or more base mismatches. Alternatively, the basepairing may be exact, e.g., not include any mismatches.

As used herein, the term "homologous recombination" refers to a type of genetic recombination in which nucleotide sequences are exchanged between two similar or identical molecules of DNA known as homologous sequences or homology arms. Homologous recombination often involves the following basic steps: after a double-strand break (DSB) occurs on both strands of DNA, sections of DNA around the 5' ends of the DSB are cut away in a process called resection. In the strand invasion step that follows, an overhanging 3' end of the broken DNA molecule "invades" a similar or identical (or homologous) DNA molecule, e.g., a "homology arm", that is not broken.

After strand invasion, the further sequence of events may follow either of two main pathways—the DSBR (double-strand break repair) pathway or the SDSA (synthesis-dependent strand annealing) pathway.

As used herein, the term "endogenous genomic DNA" refers to a certain segment of genomic DNA, e.g., that is to be replaced by an insert by knockin. The endogenous genomic DNA, e.g., to be replaced or deleted, may or may not be homologous in sequence to the donor nucleic acid comprising the insert, so long as they are both flanked by the same or similar homology arms.

As used herein, the term "knockout" is a genetic modification resulting from the disruption of the genetic information encoded in a chromosomal locus.

As used herein, the term "knockin" is a genetic modification resulting from the replacement of the genetic information encoded in a chromosomal locus with a different nucleic acid sequence.

As used herein, the term "knockout organism" is an organism in which a significant proportion of the organism's cells harbor a knockout.

As used herein, the term "knockin organism" is an organism in which a significant proportion of the organism's cells harbor a knockin.

DESCRIPTION

The use of gene editing tools (e.g., CRISPR/Cas9. TALEN, ZFN, etc., and related tools) has become a widely used gene editing technology. However, one aspect that remains to be improved is the low efficiency of knocking in (KI) large fragment nucleic acid inserts (e.g., a reporter gene) at a target site. For example, conventional CRISPR methods often have an efficiency of less than 1% for KI of large fragments. In addition, one important concern is off-target editing related to insufficient specificity of the CRISPR knock in.

BE27 Domain

In some embodiments, the present technology comprises use of a gene editing nuclease-BE27 fusion in which a gene editing nuclease is fused to exon 27 from the BRCA2 gene (see, e.g., the Examples herein). In some embodiments, a gene editing nuclease is fused to a plurality of BE27 domains (e.g., 1, 2, 3, 4, 5, 6, 7, 8, 9, 10, 11, 12, 13, 14, 15, 16, 17, 18, 19, 20, 21, 22, 23, 24, or 25 or more BE27 domains). In some embodiments, a polypeptide comprises a plurality of BE27 domains arranged serially, e.g., in a tandem array. In some embodiments, a gene editing nuclease-BE27 fusion comprises a plurality of BE27 domains separated by one or more linker sequences (e.g., separating one or more of the plurality of the BE27 domains).

In some embodiments, the BE27 amino acid sequence is provided by human BRCA2 residues 3,270-3,305, e.g:

SEQ ID NO: 1
ALDFLSRLPLPPPVSPICTFVSPAAQKAFQPPRSCG

The BRCA2 gene sequence is provided by NCBI accession NG_012772.3, which is incorporated herein by reference. In some embodiments, the technology comprises a substituted variant of SEQ ID NO: 1 that provides the same or similar function of the BE27 polypeptide (e.g., SEQ ID NO: 1 comprising one or more conservative substitutions). The technology includes any nucleic acid sequence encoding SEQ ID NO: 1. e.g., a nucleic acid comprising SEQ ID NO: 7:

```
gcnytngayttyytnwsnmgnytnccnytnccncncngtnwsnccnat htgyacnttygtnwsnccngcngcncaraargcnttycarcncnmgnw sntgyggn
```

In some embodiments, a nucleic acid encoding the BE27 polypeptide (e.g., according to SEQ ID NO: 1) comprises SEQ ID NO: 8:

```
gccttggatttcttgagtagactgcctttacctccacctgttagtcccat ttgtacatttgtttctccggctgcacagaaggcatttcagccaccaagga gttgtggc
```

RNP Complexes, Polypeptides, Ribonucleic Acids

In some embodiments, the technology comprises use of a ribonucleoprotein (RNP) comprising a gene editing nuclease-BE27 fusion. In some embodiments, the technology comprises used of a RNP complex comprising a Cas9 or Cas9-like protein and an RNA (e.g., e.g., a gRNA (e.g., a subject DNA-targeting RNA, an activator-RNA and a targeter-RNA, a crRNA and a tracrRNA; a dgRNA; a sgRNA)). In some embodiments, the protein is a Cas9 or Cas9-like protein fused to a BE27 domain ("Cas9-BE27" or "Cas9-BE27 protein fusion") as described herein. Thus, in some embodiments the technology comprises use of a ribonucleoprotein (RNP) complex comprising a Cas9 or Cas9-like protein fused to a BE27 domain ("Cas9-BE27" or "Cas9-BE27 protein fusion") as described herein and an RNA (e.g., e.g., a gRNA (e.g., a subject DNA-targeting RNA, an activator-RNA and a targeter-RNA, a crRNA and a tracrRNA; a dgRNA; a sgRNA)).

The RNA provides target specificity to the RNP complex by comprising a nucleotide sequence that is complementary to a sequence of a target DNA. The polypeptide of the complex provides binding and nuclease activity. In other words, the polypeptide is guided to a DNA sequence (e.g. a chromosomal sequence or an extrachromosomal sequence (e.g., an episomal sequence, a minicircle sequence, a mitochondrial sequence, a chloroplast sequence, etc.)) by virtue of its association with at least the protein-binding segment of the DNA-targeting RNA.

While various CRISPR/Cas systems have been used extensively for genome editing in cells of various types and species, recombinant and engineered nucleic acid-binding proteins such as Cas9 and Cas9-like proteins find use in the present technology to direct detectable labels to specific nucleic acids. Embodiments of the technology provide an RNP comprising a polypeptide, e.g., a Cas9, Cas9-BE27, or related or similar protein. The Cas9 protein was discovered as a component of the bacterial adaptive immune system (see. e.g., Barrangou et al. (2007) "CRISPR provides acquired resistance against viruses in prokaryotes" Science 315: 1709-1712, incorporated herein by reference). Cas9 is an RNA-guided endonuclease that targets and destroys foreign DNA in bacteria using RNA:DNA base-pairing between a guide RNA (gRNA) and foreign DNA to provide sequence specificity. Recently, Cas9/gRNA complexes (e.g., a Cas9/gRNA RNP) have found use in genome editing (see, e.g., Doudna et al. (2014) "The new frontier of genome engineering with CRISPR-Cas9" Science 346: 6213, incorporated herein by reference).

Accordingly, some Cas9/RNA RNP complexes comprise two RNA molecules: (1) a CRISPR RNA (crRNA), possessing a nucleotide sequence complementary to the target nucleotide sequence; and (2) a trans-activating crRNA (tracrRNA). In this mode. Cas9 functions as an RNA-guided nuclease that uses both the crRNA and tracrRNA to recognize and cleave a target sequence. Recently, a single chimeric guide RNA (sgRNA) mimicking the structure of the annealed crRNA/tracrRNA has become more widely used than crRNA/tracrRNA because the gRNA approach provides a simplified system with only two components (e.g., the Cas9 or Cas9-BE27 and the gRNA). Thus, sequence-specific binding of the RNP to a nucleic acid can be guided by a dual-RNA complex (e.g., a "dgRNA"), e.g., comprising a crRNA and a tracrRNA in two separate RNAs or by a chimeric single-guide RNA (e.g., a "sgRNA") comprising a crRNA and a tracrRNA in a single RNA. (see. e.g., Jinek et al. (2012) "A Programmable Dual-RNA-Guided DNA Endonuclease in Adaptive Bacterial Immunity" Science 337:816-821, incorporated herein by reference).

As used herein, the targeting region of a crRNA (2-RNA dgRNA system) or a sgRNA (single guide system) is referred to as the "guide RNA" (gRNA). In some embodiments, the gRNA comprises, consists of, or essentially consists of 10 to 50 bases, e.g., 15 to 40 bases, e.g., 15 to 30 bases, e.g., 15 to 25 bases (e.g., 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, or 50 bases). Methods are known in the art for determining the length of the gRNA that provides the most efficient target recognition for a Cas9. See, e.g., Lee et al. (2016) "The *Neisseria meningitidis* CRISPR-Cas9 System Enables Specific Genome Editing in Mammalian Cells" Molecular Therapy 24: 645 (2016), incorporated herein by reference.

Accordingly, in some embodiments the gRNA is a short synthetic RNA comprising a "scaffold sequence" (protein-binding segment) for Cas9 or Cas9-BE27 binding and a user-defined "DNA-targeting sequence" (DNA-targeting segment) that is approximately 20-nucleotides long and is complementary to the target site of the target nucleic acid.

In some embodiments, DNA targeting specificity is determined by two factors: 1) a DNA sequence matching the gRNA targeting sequence and a protospacer adjacent motif (PAM) directly downstream of the target sequence. Some Cas9/gRNA complexes recognize a DNA sequence comprising a protospacer adjacent motif (PAM) sequence and an adjacent sequence comprising approximately 20 bases complementary to the gRNA. Canonical PAM sequences are NGG or NAG for Cas9 from *Streptococcus pyogenes* and NNNNGATT for the Cas9 from *Neisseria meningitidis*. In some embodiments, the technology comprises use of a Cas9 having an expanded PAM recognition (e.g., an xCas9 protein). Following DNA recognition by hybridization of the gRNA to the DNA target sequence, Cas9 cleaves the DNA sequence via an intrinsic nuclease activity. For genome editing and other purposes, the CRISPR/Cas system from *S. pyogenes* been used most often. Using this system, one can target a given target nucleic acid (e.g., for editing or other manipulation) by designing a gRNA comprising a nucleotide sequence complementary to a DNA sequence (e.g., a DNA sequence comprising approximately 20 nucleotides) that is 5'-adjacent to the PAM. Methods are known in the art for determining a PAM sequence that provides efficient target recognition for a Cas9 (and thus for a Cas9-BE27). See, e.g., Zhang et al. (2013) "Processing-independent CRISPR RNAs limit natural transformation in *Neisseria meningitidis*" Molecular Cell 50: 488-503, incorporated herein by reference: Lee et al., supra, incorporated herein by reference.

In some exemplary embodiments, the crRNA comprises a sequence according to SEQ ID NO: 6

NNNNNNNNNNNNNrGrUrUrUrArArGrArGrCrUrArUrGrCrUrGrUrU rUrUrG where the "NNNNNNNNNNNN" represents the DNA-targeting sequence that is complementary to the target sequence (e.g., of a nucleic acid to be subject to editing (e.g., knockin)). In some embodiments, the 5' end of the crRNA comprises a detectable label, e.g., a dye, e.g., a fluorescent dye.

Figure 6:
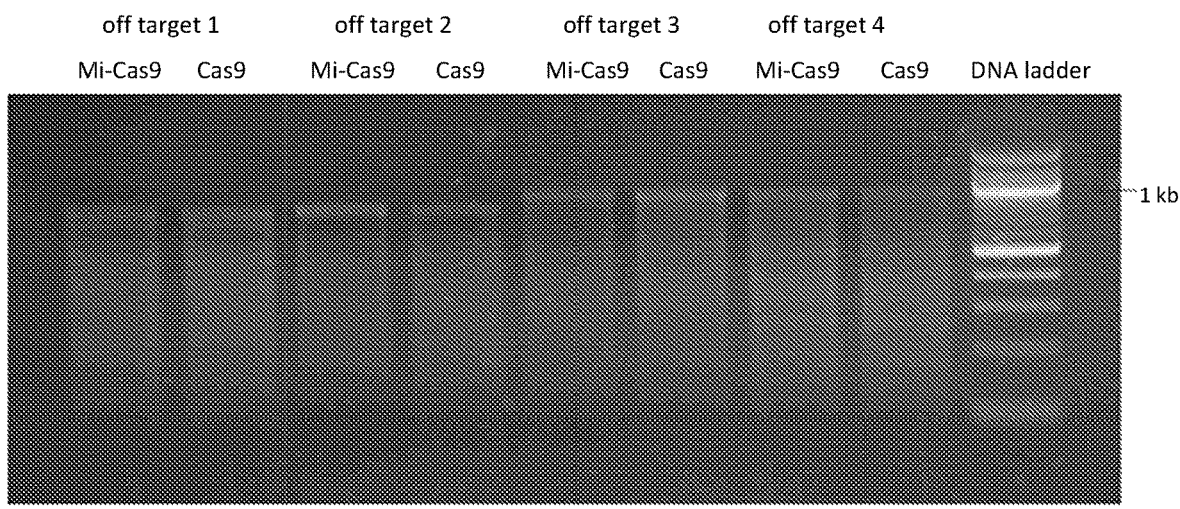
FIG. 6 provides two images of agarose gels showing the results of experiments to identify off-target effects associated with knockin of GFP at the AAVS1 locus (top gel) and Rosa26 locus (bottom gel) using an embodiment of the gene editing nuclease-BE27 fusion protein technology as described herein.
Figure 6:
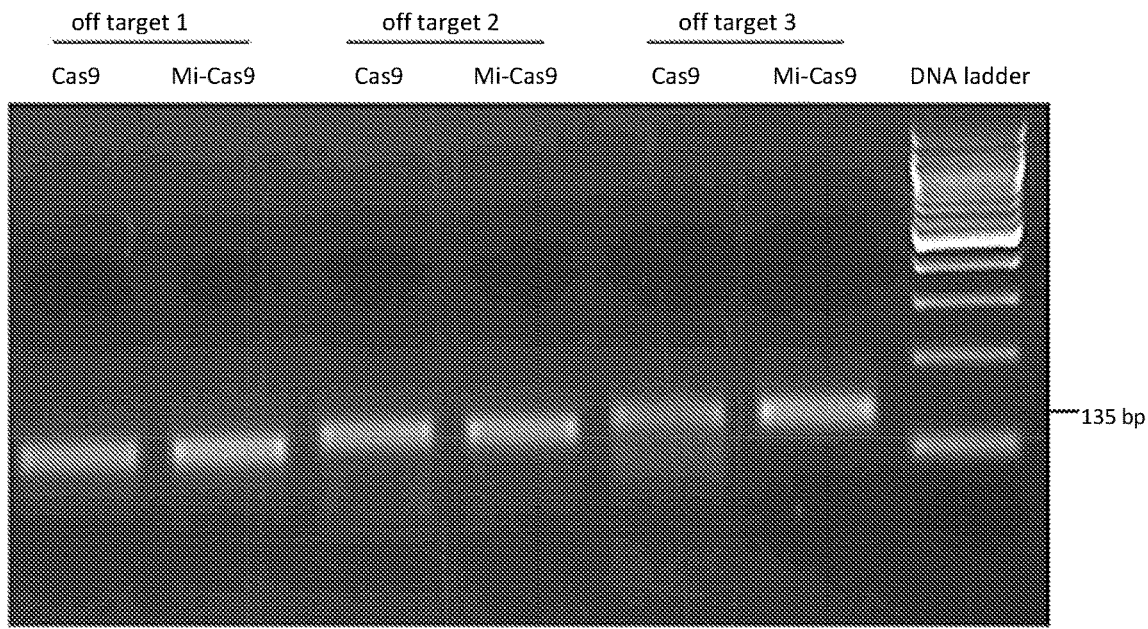

In some embodiments, the tracrRNA comprises a sequence of a naturally occurring tracrRNA, e.g., a provided by FIGS. 6, 35, and 37, and by SEQ ID NOs: 267-272 and 431-562 of U.S. Pat. App. Pub. No. 20170051312, incorporated herein by reference.

In some embodiments, the crRNA comprises a sequence that hybridizes to a tracrRNA to form a duplex structure, e.g., a sequence provided by FIG. 7 and SEQ ID NOs: 563-679 of U.S. Pat. App. Pub. No. 20170051312, incorporated herein by reference. In some embodiments, a crRNA comprises a sequence provided by FIG. 37 of U.S. Pat. App. Pub. No. 20170051312, incorporated herein by reference. In some embodiments, the duplex-forming segment of the crRNA is at least about 60% identical to one of the tracrRNA molecules set forth in SEQ ID NOs: 431-679 of U.S. Pat. App. Pub. No. 20170051312, incorporated herein by reference, or a complement thereof.

Thus, in some embodiments, exemplary (but not limiting) nucleotide sequences that are included in a dgRNA system include either of the sequences set forth in U.S. Pat. App. Pub. No. 20170051312, incorporated herein by reference, as SEQ ID NOs: 431-562, or complements thereof pairing with any sequences set forth in U.S. Pat. App. Pub. No. 20170051312, incorporated herein by reference, SEQ ID NOs: 563-679, or complements thereof that can hybridize to form a protein binding segment.

In some embodiments, a single-molecule gRNA (e.g., a sgRNA) comprises two complementary stretches of nucleotides that hybridize to form a dsRNA duplex. In some embodiments, the sgRNA (or a DNA encoding the sgRNA) is at least about 60% identical to one of the tracrRNA molecules set forth in U.S. Pat. App. Pub. No. 20170051312, incorporated herein by reference, as SEQ ID NOs: 431-562, or a complement thereof, over at least 8 contiguous nucleotides. In some embodiments, the sgRNA (or a DNA encoding the sgRNA) is at least about 60/o identical to one of the tracrRNA molecules set forth in U.S. Pat. App. Pub. No. 20170051312, incorporated herein by reference, as SEQ ID NOs: 563-679, or a complement thereof, over at least 8 contiguous nucleotides. Appropriate naturally occurring pairs of crRNAs and tracrRNAs can be routinely determined by taking into account the species name and base-pairing (for the dsRNA duplex of the protein-binding domain) when determining appropriate cognate pairs.

In some embodiments, the technology provides a gene editing nuclease-BE27 fusion that is a Cas9-BE27. In some embodiments, a Cas9-BE27/gRNA complex binds to a target nucleic acid with a sequence specificity provided by the gRNA to produce a double strand break in the nucleic acid. In some embodiments, the Cas9-BE27/gRNA RNP binds to the target nucleic acid with sequence specificity; in some embodiments, the RNP "melts" the target sequence to provide single-stranded regions of the target nucleic acid in a sequence-specific manner (see. e.g., Qi et al. (2013) "Repurposing CRISPR as an RNA-guided platform for sequence-specific control of gene expression" Cell 152(5): 1173-83, incorporated herein by reference).

Furthermore, while the Cas9/gRNA system initially targeted sequences adjacent to a PAM, in some embodiments the Cas9-BE27/gRNA system as used herein has been engineered to target any nucleotide sequence for binding (e.g., the technologies described herein are PAM-independent). Also, Cas9 orthologs encoded by compact genes (e.g., Cas9 from *Staphylococcus aureus*) are known (see, e.g., Ran et al. (2015) "In vivo genome editing using *Staphylococcus aureus* Cas9" Nature 520: 186-191, incorporated herein by reference), which improves the cloning and manipulation of the Cas9 components in vitro. The technology encompasses embodiments comprising use of these compact genes fused to BE27.

In some embodiments, different Cas9 proteins (e.g., Cas9 proteins from various species and modified versions (e.g., nuclease-deficient versions) thereof) may be advantageous to use in the various provided methods in order to capitalize on various characteristics of the different Cas9 proteins (e.g., for different. PAM sequence preferences; for no PAM sequence requirement; for increased or decreased binding activity; for an increased or decreased level of cellular toxicity; for increase or decrease efficiency of in vitro RNP formation; for increase or decrease ability for introduction into cells (e.g., living cells. e.g., living primary cells), etc.). Cas9 proteins from various species may require different PAM sequences in the target DNA. Thus, for a particular Cas9 protein of choice, the PAM sequence requirement may be different than the 5'-XGG-3' sequence described above. In some embodiments, the protein is an xCas protein having an expanded PAM compatibility (e.g., a Cas9 variant that recognizes a broad range of PAM sequences including NG, GAA and GAT), e.g., as described in Hu et al. (2018) "Evolved Cas9 variants with broad PAM compatibility and high DNA specificity" Nature 556: 57-63, incorporated herein by reference in its entirety.

In some embodiments, the technology comprises use of other RNA-guided nucleases (e.g., Cpf1 and modified versions thereof). For example, in some embodiments use of other RNA-guided nucleases (e.g., Cpf1 and modified versions thereof provides advantages—e.g., in some embodiments the characteristics of the different nucleases are appropriate for methods as described herein (e.g., other RNA-guided nucleases have preferences for different PAM sequence preferences; other RNA-guided nucleases operate using single crRNAs other than cr/tracrRNA complexes; other RNA-guided nucleases operate with shorter guide RNAs, etc.) In some embodiments, the technology comprises use of a Cpf1 enzyme, e.g., as described in U.S. Pat. No. 9,790,490, which is incorporated herein by reference in its entirety.

Many Cas9 orthologs from a wide variety of species have been identified herein and the proteins share only a few identical amino acids. All identified Cas9 orthologs have the same domain architecture with a central HNH endonuclease domain and a split RuvC/RNaseH domain. Cas9 proteins share 4 key motifs with a conserved architecture. Motifs 1, 2, and 4 are RuvC like motifs while motif 3 is an HNH-motif. In some embodiments, a suitable polypeptide (e.g., a Cas9) comprises an amino acid sequence having 4 motifs, each of motifs 1-4 having at least about 75%, at least about, 80%, at least about 85%, at least about 90%, at least about 95%, at least about 99% or 100% amino acid sequence identity to the motifs 1-4 of a known Cas9 and/or Csn1 amino acid sequence.

A number of bacteria express Cas9 protein variants. The Cas9 from *Streptococcus pyogenes* is presently the most commonly used; some of the other Cas9 proteins have high levels of sequence identity with the *S. pyogenes* Cas9 and use the same guide RNAs. Others are more diverse, use different gRNAs, and recognize different PAM sequences as well (the 2-5 nucleotide sequence specified by the protein which is adjacent to the sequence specified by the RNA). Chylinski et al. classified Cas9 proteins from a large group of bacteria (RNA Biology 10:5, 1-12; 2013, incorporated herein by reference), and a large number of Cas9 proteins are listed in supplementary FIG. 1 and supplementary table 1 thereof, which are incorporated by reference herein. Additional Cas9 proteins are described in Esvelt et al., Nat Methods, 2013 November; 10(11):1116-21 and Fonfara et al., "Phylogeny of Cas9 determines functional exchangeability of dual-RNA and Cas9 among orthologous type II CRISPR-Cas systems." Nucleic Acids Res. 42: 2577-90 (2014), each of which is incorporated herein by reference.

Cas9, and thus Cas9-BE27, molecules of a variety of species find use in the technology described herein. While the *S. pyogenes* and *S. thermophilus* Cas9 molecules are widely used, Cas9 molecules of, derived from, or based on the Cas9 proteins of other species listed herein find use in embodiments of the technology. Accordingly, the technology provides for the replacement of *S. pyogenes* and *S. thermophilus* Cas9 and Cas9-BE27 molecules with Cas9 and Cas9-BE27 molecules from the other species, e.g.:

| Gen.Bank Acc No. | Bacterium |
| --- | --- |
| 303229466 | *Veillonella atypica* ACS-134-V-Col7a |
| 34762592 | *Fusobacterium nucleatum* subsp. *vincentii* |
| 374307738 | *Filifactor alocis* ATCC 35896 |
| 320528778 | *Solobacterium moorei* F0204 |
| 291520705 | *Coprococcus catus* GD-7 |
| 42525843 | *Treponema denticola* ATCC 35405 |
| 304438954 | *Peptoniphilus duerdenii* ATCC BAA-1640 |
| 224543312 | *Catenibacterium mitsuokai* DSM 15897 |
| 24379809 | *Streptococcus mutans* UA159 |
| 15675041 | *Streptococcus pyogenes* SF370 |
| 16801805 | *Listeria innocua* Clip 11262 |
| 116628213 | *Streptococcus thermophilus* LMD-9 |
| 323463801 | *Staphylococcus pseudintermedius* ED99 |
| 352684361 | *Acidaminococcus intestini* RyC-MR95 |
| 302336020 | *Olsenella uli* DSM 7084 |
| 366983953 | *Oenococcus kitaharae* DSM 17330 |
| 310286728 | *Bifidobacterium bifidum* S17 |
| 258509199 | *Lactobacillus rhamnosus* GG |
| 300361537 | *Lactobacillus gasseri* JV-V03 |
| 169823755 | *Finegoldia magna* ATCC 29328 |
| 47458868 | *Mycoplasma mobile* 163K |
| 284931710 | *Mycoplasma gallisepticum* str. F |
| 363542550 | *Mycoplasma ovipneumoniae* SC01 |
| 384393286 | *Mycoplasma canis* PG 14 |
| 71894592 | *Mycoplasma synoviae* 53 |
| 238924075 | *Eubacterium rectale* ATCC 33656 |
| 116627542 | *Streptococcus thermophilus* LMD-9 |
| 315149830 | *Enterococcus faecalis* TX0012 |
| 315659848 | *Staphylococcus lugdunensis* M23590 |
| 160915782 | *Eubacterium dolichum* DSM 3991 |
| 336393381 | *Lactobacillus coryniformis* subsp. *torquens* |
| 310780384 | *Ilyobacter polytropus* DSM 2926 |
| 325677756 | *Ruminococcus albus* 8 |
| 187736489 | *Akkermansia muciniphila* ATCC BAA-835 |
| 117929158 | *Acidothermus cellulolyticus* 11B |

-continued

| Gen.Bank Acc No. | Bacterium |
| --- | --- |
| 189440764 | *Bifidobacterium longum* DJO10A |
| 283456135 | *Bifidobacterium dentium* Bd1 |
| 38232678 | *Corynebacterium diphtheriae* NCTC 13129 |
| 187250660 | *Elusimicrobium minutum* Pei191 |
| 319957206 | *Nitratifractor salsuginis* DSM 16511 |
| 325972003 | *Sphaerochaeta globus* str. Buddy |
| 261414553 | *Fibrobacter succinogenes* subsp. *succinogenes* |
| 60683389 | *Bacteroides fragilis* NCTC 9343 |
| 256819408 | *Capnocytophaga ochracea* DSM 7271 |
| 90425961 | *Rhodopseudomonas palustris* BisB18 |
| 373501184 | *Prevotella micans* F0438 |
| 294674019 | *Prevotella ruminicola* 23 |
| 365959402 | *Flavobacterium columnare* ATCC 49512 |
| 312879015 | *Aminomonas paucivorans* DSM 12260 |
| 83591793 | *Rhodospirillum rubrum* ATCC 11170 |
| 294086111 | *Candidatus Puniceispirillum marinum* IMCC1322 |
| 121608211 | *Verminephrobacter eiseniae* EF01-2 |
| 344171927 | *Ralstonia syzygii* R24 |
| 159042956 | *Dinoroseobacter shibae* DFL 12 |
| 288957741 | *Azospirillum* sp- B510 |
| 92109262 | *Nitrobacter hamburgensis* X14 |
| 148255343 | *Bradyrhizobium* sp- BTAi1 |
| 34557790 | *Wolinella succinogenes* DSM 1740 |
| 218563121 | *Campylobacter jejuni* subsp. *jejuni* |
| 291276265 | *Helicobacter mustelae* 12198 |
| 229113166 | *Bacillus cereus* Rock 1-15 |
| 222109285 | *Acidovorax ebreus* TPSY |
| 189485225 | uncultured Termite group 1 |
| 182624245 | *Clostridium perfringens* D str. |
| 220930482 | *Clostridium cellulolyticum* H10 |
| 154250555 | *Parvibaculum lavamentivorans* DS-1 |
| 257413184 | *Roseburia intestinalis* L1-82 |
| 218767588 | *Neisseria meningitidis* Z2491 |
| 15602992 | *Pasteurella multocida* subsp. *multocida* |
| 319941583 | *Sutterella wadsworthensis* 3 1 |
| 254447899 | gamma proteobacterium HTCC5015 |
| 54296138 | *Legionella pneumophila* str. Paris |
| 331001027 | *Parasutterella excrementihominis* YIT 11859 |
| 34557932 | *Wolinella succinogenes* DSM 1740 |
| 118497352 | *Francisella novicida* U112 |

See also U.S. Pat. App. Pub. No. 20170051312 at FIGS. 3, 4, 5, incorporated herein by reference.

In some embodiments, the technology described herein encompasses the use of a Cas9-1BE27 fusion protein derived from any Cas9 protein (e.g., as listed above) and their corresponding guide RNAs or other guide RNAs that are compatible. The Cas9 from *Streptococcus thermophilus* LMD-9 CRISPR1 system has been shown to function in human cells (see. e.g., Cong et al. (2013) Science 339: 819, incorporated herein by reference). Additionally, Jinek showed in vitro that Cas9 orthologs from *S. thermophilus* and *L. innocua*, can be guided by a dual *S. pyogenes* grNA to cleave target plasmid DNA.

In some embodiments, the present technology comprises the Cas9 protein from *S. pyogenes* either as encoded in bacteria or codon-optimized for expression in mammalian cells. For example, in some embodiments, the Cas9 used herein is at least approximately 50% identical to the sequence of *S. pyogenes* Cas9, e.g., at, least 50% identical to the following sequence (SEQ ID NO: 9).

```
Met Asp Lys Lys Tyr Ser Ile Gly Leu Asp Ile Gly Thr Asn Ser Val
1               5                   10                  15
Gly Trp Ala Val Ile Thr Asp Glu Tyr Lys Val Pro Ser Lys Lys Phe
                20                  25                  30
Lys Val Leu Gly Asn Thr Asp Arg His Ser Ile Lys Lys Asn Leu Ile
                35                  40                  45
Gly Ala Leu Leu Phe Asp Ser Gly Glu Thr Ala Glu Ala Thr Arg Leu
            50                  55                  60
Lys Arg Thr Ala Arg Arg Arg Tyr Thr Arg Arg Lys Asn Arg Ile Cys
65                  70                  75                  80
Tyr Leu Gln Glu Ile Phe Ser Asn Glu Met Ala Lys Val Asp Asp Ser
                85                  90                  95
Phe Phe His Arg Leu Glu Glu Ser Phe Leu Val Glu Glu Asp Lys Lys
                100                 105                 110
His Glu Arg His Pro Ile Phe Gly Asn Ile Val Asp Glu Val Ala Tyr
                115                 120                 125
His Glu Lys Tyr Pro Thr Ile Tyr His Leu Arg Lys Lys Leu Val Asp
                130                 135                 140
Ser Thr Asp Lys Ala Asp Leu Arg Leu Ile Tyr Leu Ala Leu Ala His
145                 150                 155                 160
Met Ile Lys Phe Arg Gly His Phe Leu Ile Glu Gly Asp Leu Asn Pro
                165                 170                 175
Asp Asn Ser Asp Val Asp Lys Leu Phe Ile Gln Leu Val Gln Thr Tyr
                180                 185                 190
Asn Gln Leu Phe Glu Glu Asn Pro Ile Asn Ala Ser Gly Val Asp Ala
                195                 200                 205
Lys Ala Ile Leu Ser Ala Arg Leu Ser Lys Ser Arg Arg Leu Glu Asn
                210                 215                 220
Leu Ile Ala Gln Leu Pro Gly Glu Lys Lys Asn Gly Leu Phe Gly Asn
225                 230                 235                 240
Leu Ile Ala Leu Ser Leu Gly Leu Thr Pro Asn Phe Lys Ser Asn Phe
                245                 250                 255
Asp Leu Ala Glu Asp Ala Lys Leu Gln Leu Ser Lys Asp Thr Tyr Asp
                260                 265                 270
Asp Asp Leu Asp Asn Leu Leu Ala Gln Ile Gly Asp Gln Tyr Ala Asp
                275                 280                 285
Leu Phe Leu Ala Ala Lys Asn Leu Ser Asp Ala Ile Leu Leu Ser Asp
                290                 295                 300
Ile Leu Arg Val Asn Thr Glu Ile Thr Lys Ala Pro Leu Ser Ala Ser
305                 310                 315                 320
Met Ile Lys Arg Tyr Asp Glu His His Gln Asp Leu Thr Leu Leu Lys
                325                 330                 335
Ala Leu Val Arg Gln Gln Leu Pro Glu Lys Tyr Lys Glu Ile Phe Phe
                340                 345                 350
Asp Gln Ser Lys Asn Gly Tyr Ala Gly Tyr Ile Asp Gly Gly Ala Ser
                355                 360                 365
Gln Glu Glu Phe Tyr Lys Phe Ile Lys Pro Ile Leu Glu Lys Met Asp
                370                 375                 380
Gly Thr Glu Glu Leu Leu Val Lys Leu Asn Arg Glu Asp Leu Leu Arg
385                 390                 395                 400
Lys Gln Arg Thr Phe Asp Asn Gly Ser Ile Pro His Gln Ile His Leu
                405                 410                 415
Gly Glu Leu His Ala Ile Leu Arg Arg Gln Glu Asp Phe Tyr Pro Phe
                420                 425                 430
```

-continued

```
Leu Lys Asp Asn Arg Glu Lys Ile Glu Lys Ile Leu Thr Phe Arg Ile
            435                 440                 445
Pro Tyr Tyr Val Gly Pro Leu Ala Arg Gly Asn Ser Arg Phe Ala Trp
        450                 455                 460
Met Thr Arg Lys Ser Glu Glu Thr Ile Thr Pro Trp Asn Phe Glu Glu
465                 470                 475                 480
Val Val Asp Lys Gly Ala Ser Ala Gln Ser Phe Ile Glu Arg Met Thr
                485                 490                 495
Asn Phe Asp Lys Asn Leu Pro Asn Glu Lys Val Leu Pro Lys His Ser
            500                 505                 510
Leu Leu Tyr Glu Tyr Phe Thr Val Tyr Asn Glu Leu Thr Lys Val Lys
        515                 520                 525
Tyr Val Thr Glu Gly Met Arg Lys Pro Ala Phe Leu Ser Gly Glu Gln
    530                 535                 540
Lys Lys Ala Ile Val Asp Leu Leu Phe Lys Thr Asn Arg Lys Val Thr
545                 550                 555                 560
Val Lys Gln Leu Lys Glu Asp Tyr Phe Lys Lys Ile Glu Cys Phe Asp
                565                 570                 575
Ser Val Glu Ile Ser Gly Val Glu Asp Arg Phe Asn Ala Ser Leu Gly
            580                 585                 590
Thr Tyr His Asp Leu Leu Lys Ile Ile Lys Asp Lys Asp Phe Leu Asp
        595                 600                 605
Asn Glu Glu Asn Glu Asp Ile Leu Glu Asp Ile Val Leu Thr Leu Thr
    610                 615                 620
Leu Phe Glu Asp Arg Glu Met Ile Glu Glu Arg Leu Lys Thr Tyr Ala
625                 630                 635                 640
His Leu Phe Asp Asp Lys Val Met Lys Gln Leu Lys Arg Arg Arg Tyr
                645                 650                 655
Thr Gly Trp Gly Arg Leu Ser Arg Lys Leu Ile Asn Gly Ile Arg Asp
            660                 665                 670
Lys Gln Ser Gly Lys Thr Ile Leu Asp Phe Leu Lys Ser Asp Gly Phe
        675                 680                 685
Ala Asn Arg Asn Phe Met Gln Leu Ile His Asp Asp Ser Leu Thr Phe
    690                 695                 700
Lys Glu Asp Ile Gln Lys Ala Gln Val Ser Gly Gln Gly Asp Ser Leu
705                 710                 715                 720
His Glu His Ile Ala Asn Leu Ala Gly Ser Pro Ala Ile Lys Lys Gly
                725                 730                 735
Ile Leu Gln Thr Val Lys Val Val Asp Glu Leu Val Lys Val Met Gly
            740                 745                 750
Arg His Lys Pro Glu Asn Ile Val Ile Glu Met Ala Arg Glu Asn Gln
        755                 760                 765
Thr Thr Gln Lys Gly Gln Lys Asn Ser Arg Glu Arg Met Lys Arg Ile
    770                 775                 780
Glu Glu Gly Ile Lys Glu Leu Gly Ser Gln Ile Leu Lys Glu His Pro
785                 790                 795                 800
Val Glu Asn Thr Gln Leu Gln Asn Glu Lys Leu Tyr Leu Tyr Tyr Leu
                805                 810                 815
Gln Asn Gly Arg Asp Met Tyr Val Asp Gln Glu Leu Asp Ile Asn Arg
            820                 825                 830
Leu Ser Asp Tyr Asp Val Asp His Ile Val Pro Gln Ser Phe Leu Lys
        835                 840                 845
Asp Asp Ser Ile Asp Asn Lys Val Leu Thr Arg Ser Asp Lys Asn Arg
    850                 855                 860
```

-continued

```
Gly Lys Ser Asp Asn Val Pro Ser Glu Glu Val Lys Met Lys
865                 870                 875                 880

Asn Tyr Trp Arg Gln Leu Leu Asn Ala Lys Leu Ile Thr Gln Arg Lys
            885                 890                 895

Phe Asp Asn Leu Thr Lys Ala Glu Arg Gly Gly Leu Ser Glu Leu Asp
                900                 905                 910

Lys Ala Gly Phe Ile Lys Arg Gln Leu Val Glu Thr Arg Gln Ile Thr
            915                 920                 925

Lys His Val Ala Gln Ile Leu Asp Ser Arg Met Asn Thr Lys Tyr Asp
        930                 935                 940

Glu Asn Asp Lys Leu Ile Arg Glu Val Lys Val Ile Thr Leu Lys Ser
945                 950                 955                 960

Lys Leu Val Ser Asp Phe Arg Lys Asp Phe Gln Phe Tyr Lys Val Arg
                965                 970                 975

Glu Ile Asn Asn Tyr His His Ala His Asp Ala Tyr Leu Asn Ala Val
            980                 985                 990

Val Gly Thr Ala Leu Ile Lys Lys Tyr Pro Lys Leu Glu Ser Glu Phe
        995                 1000                1005

Val Tyr Gly Asp Tyr Lys Val Tyr Asp Val Arg Lys Met Ile Ala
    1010                1015                1020

Lys Ser Glu Gln Glu Ile Gly Lys Ala Thr Ala Lys Tyr Phe Phe
    1025                1030                1035

Tyr Ser Asn Ile Met Asn Phe Phe Lys Thr Glu Ile Thr Leu Ala
    1040                1045                1050

Asn Gly Glu Ile Arg Lys Arg Pro Leu Ile Glu Thr Asn Gly Glu
    1055                1060                1065

Thr Gly Glu Ile Val Trp Asp Lys Gly Arg Asp Phe Ala Thr Val
    1070                1075                1080

Arg Lys Val Leu Ser Met Pro Gln Val Asn Ile Val Lys Lys Thr
    1085                1090                1095

Glu Val Gln Thr Gly Gly Phe Ser Lys Glu Ser Ile Leu Pro Lys
    1100                1105                1110

Arg Asn Ser Asp Lys Leu Ile Ala Arg Lys Lys Asp Trp Asp Pro
    1115                1120                1125

Lys Lys Tyr Gly Gly Phe Asp Ser Pro Thr Val Ala Tyr Ser Val
    1130                1135                1140

Leu Val Val Ala Lys Val Glu Lys Gly Lys Ser Lys Lys Leu Lys
    1145                1150                1155

Ser Val Lys Glu Leu Leu Gly Ile Thr Ile Met Glu Arg Ser Ser
    1160                1165                1170

Phe Glu Lys Asn Pro Ile Asp Phe Leu Glu Ala Lys Gly Tyr Lys
    1175                1180                1185

Glu Val Lys Lys Asp Leu Ile Ile Lys Leu Pro Lys Tyr Ser Leu
    1190                1195                1200

Phe Glu Leu Glu Asn Gly Arg Lys Arg Met Leu Ala Ser Ala Gly
    1205                1210                1215

Glu Leu Gln Lys Gly Asn Glu Leu Ala Leu Pro Ser Lys Tyr Val
    1220                1225                1230

Asn Phe Leu Tyr Leu Ala Ser His Tyr Glu Lys Leu Lys Gly Ser
    1235                1240                1245

Pro Glu Asp Asn Glu Gln Lys Gln Leu Phe Val Glu Gln His Lys
    1250                1255                1260

His Tyr Leu Asp Glu Ile Ile Glu Gln Ile Ser Glu Phe Ser Lys
    1265                1270                1275
```

```
                     -continued
Arg Val Ile Leu Ala Asp Ala Asn Leu Asp Lys Val Leu Ser Ala
    1280                1285                1290

Tyr Asn Lys His Arg Asp Lys Pro Ile Arg Glu Gln Ala Glu Asn
    1295                1300                1305

Ile Ile His Leu Phe Thr Leu Thr Asn Leu Gly Ala Pro Ala Ala
    1310                1315                1320

Phe Lys Tyr Phe Asp Thr Thr Ile Asp Arg Lys Arg Tyr Thr Ser
    1325                1330                1335

Thr Lys Glu Val Leu Asp Ala Thr Leu Ile His Gln Ser Ile Thr
    1340                1345                1350

Gly Leu Tyr Glu Thr Arg Ile Asp Leu Ser Gln Leu Gly Gly Asp
    1355                1360                1365
```

In some embodiments, the technology comprises use of a nucleotide sequence that is approximately 50%, 55%, 60%, 65%, 70%, 75%, 80%, 85%, 90%, 95%, 99% or 100% identical to a nucleotide sequence that encodes a protein described by SEQ ID NO: 9.

In some embodiments, the Cas9 portion of the Cas9-BE27 fusion protein used herein is at least about 50% identical to the sequence of the *S. pyogenes* Cas9, e.g., at least 50%, 55%, 60%, 65%, 70%, 75%, 80%, 85%, 90%, 95%, 99% or 100% identical to SEQ ID NO: 9.

In some embodiments, the polypeptide (e.g., the RNA-guided nuclease) of the RNP is and/or comprises a Cas protein, CRISPR enzyme, or Cas-like protein. "Cas protein" and "CRISPR enzyme" and "Cas-like protein", as used herein, includes polypeptides, enzymatic activities, and polypeptides having activities similar to proteins known in the art as, or encoded by genes known in the art as, e.g., Cas1, Cas1B, Cas2, Cas3, Cas4, Cas5, Cas6, Cas7, Cas8, Cas9, Cas10, Cas13, Csy1, Csy2, Csy3, Cse1, Cse2, Csc1, Csc2, Csa5, Csn2, Csm2, Csm3, Csm4, Csm5, Csm6, Cmr1, Cmr3, Cmr4, Cmr5, Cmr6, Csb1, Csb2, Csb3, Csx17, Csx14, Csx10, Csx16, CsaX, Csx3, Csx1, Csx15, Csf1, Csf2, Csf3, Csf4, Cpf1, C2c1, C2c2, HiFiCas9, spCas9mSA, HypaCas9 (see, e.g., Chen (2017) "Enhanced proofreading governs CRISPR-Cas9 targeting accuracy" Nature 550(7676):407-410, incorporated herein by reference), and xCas9 (see. e.g., Hu (2018) "Evolved Cas9 variants with broad PAM compatibility and high DNA specificity" Nature 556(7699):57-63, incorporated herein by reference), homologs thereof, or modified versions thereof, e.g., including fusions of BE27 with any of these Cas proteins, CRISPR enzymes, and/or Cas-like proteins known in the art.

In some embodiments, the polypeptide (e.g., the RNA-guided nuclease) of the RNP comprises a TALEN, a portion thereof, a homolog thereof, or a modified version thereof. In some embodiments, the gene editing nuclease domain comprises ZFN, a portion thereof, a homolog thereof, or a modified version thereof.

In some embodiments, the polypeptide of the RNP is and/or comprises HiFiCas9 or spCas9mSA (see. e.g., Vakulskas (2018) A novel high-fidelity Cas9 delivered as a ribonucleoprotein complex enables high frequency gene editing in human haematopoietic stem and progenitor cells. Nature Medicine 24(8):1216-1224: and Gu (2018) Efficient generation of targeted large insertions by microinjection into two-cell-stage mouse embryos. Nature biotechnology 36(7): 632-637, each of which is incorporated herein by reference).

In some embodiments, the polypeptide (e.g., the RNA-guided nuclease) of the RNP comprises an eSpCas9 as described in Slaymaker (2016) "Rationally engineered Cas9 nucleases with improved specificity" Science 351(6268):84-8, incorporated herein by reference.

In some embodiments, the polypeptide (e.g., the RNA-guided nuclease) of the RNP comprises a SpCas9-HD1 as described in Kleinstiver (2016) "High-fidelity CRISPR-Cas9 nucleases with no detectable genome-wide off-target effects" Nature 529(7587):490-5, incorporated herein by reference.

In some embodiments, the polypeptide (e.g., the RNA-guided nuclease) of the RNP comprises a "highly enhanced fidelity" nuclease variant as described in Kulcsar (2017) Genome Biology 18: 190, incorporated herein by reference.

In some embodiments, the polypeptide (e.g., the RNA-guided nuclease) of the RNP comprises a HiFiCas9 as described in Vakulskas (2018) "A novel high-fidelity Cas9 delivered as a ribonucleoprotein complex enables high frequency gene editing in human haematopoietic stem and progenitor cells" Nature Medicine 24(8): 1216-1224, incorporated herein by reference.

In some embodiments, the polypeptide (e.g., the RNA-guided nuclease) of the RNP comprises and/or is fused to a polypeptide that modulates its activity. For instance, in some embodiments, the gene editing nuclease is fused to Gem (e.g., hGem) (see, e.g., Gutschner (2016) "Post-translational Regulation of Cas9 during G1 Enhances Homology-Directed Repair" Cell Rep 14(6):1555-1566; and Howden (2016) "A Cas9 Variant for Efficient Generation of Indel-Free Knockin or Gene-Corrected Human Pluripotent Stem Cells" Stem Cell Reports 7(3):508-517, each of which is incorporated herein by reference), fused to CtIP (see, e.g., Charpentier (2018) "CtIP fusion to Cas9 enhances transgene integration by homology-dependent repair" Nat Comm 9(1): 1133, incorporated herein by reference). Cyclin B2 (see, e.g., Vicente (2019) "A CyclinB2-Cas9 fusion promotes the homology-directed repair of double-strand breaks" bioR$_x$iv doi.org/10.1101/555144, incorporated herein by reference), chromatin-modulating peptides (see, e.g., Ding (2019) "Improving CRISPR-Cas9 Genome Editing Efficiency by Fusion with Chromatin-Modulating Peptides" The CRISPR Journal Vol. 2, No. 1, incorporated herein by reference), RecA (see, e.g., Lin (2017) "Fusion of SpCas9 to *E. coli* Rec A protein enhances CRISPR-Cas9 mediated gene knockout in mammalian cells" J Biotechnol 247:42-49, incorporated herein by reference), or comprising an intein that provides small-molecule control of Cas9 (see, e.g., Davis (2015) "Small molecule-triggered Cas9 protein with improved genome-editing specificity" Nat Chem Biol 11(5):316-8 (incorporated herein by reference). In some embodiments, the gene editing nuclease is fused to a polypeptide that modulates its activity (e.g., as described above) and further is fused to one or more BE27 domains.

In embodiments, the technology comprises use of a polypeptide (e.g., a Type V/Type VI protein) such as Cpf1 or C2c1 or C2c2 and homologs and orthologs of a Type V/Type VI protein such as Cpf1 or C2c1 or C2c2 to provide a fusion with BE27. Embodiments encompass Cpf1, modified Cpf1 (e.g., Cpf1-BE27 fusion), and Cpf1, and CRISPR systems related to Cpf1, modified Cpf1 (Cpf1-BE27 fusion), and chimeric Cpf1. In some embodiments, the polypeptide (e.g., a Type V/Type VI protein) such as Cpf1 or C2c1 or C2c2 is from a genus that is, e.g., *Streptococcus, Campylobacter, Nitratifractor, Staphylococcus, Parvibaculum, Roseburia, Neisseria, Gluconacetobacter, Azospirillum, Sphaerochaeta, Lactobacillus, Eubacterium, Corynebacter, Carnobacterium, Rhodobacter; Listeria, Paludibacter, Clostridium, Lachnospiraceae, Clostridiaridium, Leptotrichia, Francisella, Legionella, Alicyclobacillus, Methanomethyophilus, Porphyromonas, Prevotella, Bacteroidetes, Helcococcus, Letospira, Desulfovibrio, Desulfonatronum, Opitutaceae, Tuberibacillus, Bacillus, Brevibacilus, Methylobacterium,* or *Acidaminococcus*. In some embodiments, the polypeptide (e.g., a Type V/Type VI protein) such as Cpf1 or C2c1 or C2c2 is from an organism that is, e.g., *S. mutans, S. agalactiae, S. equisimilis. S. sanguinis, S. pneumonia; C. jejuni, C. coli* N *salsuginis, N. tergarcus; S. auricularis, S. carnosus;* N *meningitides,* N *gonorrhoeae; L. monocytogenes. L. ivanovii; C. botulinum, C. difficile, C tetani,* or *C. sordellii*. See, e.g., U.S. Pat. No. 9,790,490, incorporated herein by reference in its entirety. In some embodiments, a gene editing nuclease-BE27 fusion comprises a Cpf1 protein and finds use as described in U.S. Pat. App. Pub. No. 20180155716, which is incorporated herein by reference.

In some embodiments, differences from SEQ ID NO: 9 are in non-conserved regions, as identified by sequence alignment of sequences set forth in Chylinski et al., RNA Biology 10:5, 1-12; 2013 (e.g., in supplementary FIG. 1 and supplementary table 1 thereof); Esvelt et al., Nat Methods, 2013 November; 10(11):1116-21 and Fonfara et al., Nucl. Acids Res. (2014) 42 (4): 2577-2590, each of which is incorporated herein by reference.

Thus, in some embodiments, the polypeptide of the Cas9 portion of the RNP is a naturally-occurring polypeptide. In some embodiments, the polypeptide of the Cas9 portion of the RNP is not a naturally-occurring polypeptide (e.g., a chimeric polypeptide, a naturally-occurring polypeptide that is modified. e.g., by one or more amino acid substitutions produced by an engineered nucleic acid comprising one or more nucleotide substitutions, deletions, insertions).

In some embodiments, choosing, designing, synthesizing, and analyzing nucleotide sequences and amino acid sequences (e.g., of the polypeptide and RNA components of an RNP complex as described herein) comprise use of sequence alignment methods to identify similarities and differences in two or more nucleotide sequences or amino acid sequences. To determine the percent identity of two sequences, the sequences are aligned for optimal comparison purposes (gaps are introduced in one or both of a first and a second amino acid or nucleic acid sequence as required for optimal alignment, and non-homologous sequences can be disregarded for comparison purposes). The length of a reference sequence aligned for comparison purposes is at least 50% (in some embodiments, about 50%, 55%, 60%, 65%, 70%, 75%, 85%, 90%, 95%, or 100% of the length of the reference sequence). The nucleotides or residues at corresponding positions are then compared. When a position in the first sequence is occupied by the same nucleotide or residue as the corresponding position in the second sequence, then the molecules are identical at that position. The percent identity between the two sequences is a function of the number of identical positions shared by the sequences, taking into account the number of gaps, and the length of each gap, which need to be introduced for optimal alignment of the two sequences.

The comparison of sequences and determination of percent identity between two sequences can be accomplished using a mathematical algorithm. In some embodiments, the percent identity between two amino acid sequences is determined using the Needleman and Wunsch ((1970) J. Mol. Biol. 48:444-453, incorporated herein by reference) algorithm, which has been incorporated into the GAP program in the GCG software package, e.g., using a Blosum 62 scoring matrix with a gap penalty of 12, a gap extend penalty of 4, and a frameshift gap penalty of 5. Other methods are known in the art, e.g., as discussed elsewhere herein.

In some embodiments, the RNP comprises a protein that is a Cas9 or Cas9 derivative, e.g., a Cas9-BE27 fusion. Thus, in some embodiments, the protein is a Type II Cas9 protein. In some embodiments, the Cas9 has been engineered to partially remove the nuclease domain (e.g., a "dead Cas9" or a "Cas9 nickase"; see. e.g., Nature Methods 11: 399-402 (2014), incorporated herein by reference). In some embodiments, the RNP protein is a protein from a CRISPR system other than the *S. pyogenes* system. e.g., a Type V Cpf1, C2c1, C2c2, C2c3 proteins and derivatives thereof.

In some embodiments, the polypeptide of the RNP is a chimeric or fusion polypeptide, e.g., a polypeptide that comprises two or more functional domains (e.g., a Cas9 and a BE27 domain). For example, in some embodiments a chimeric polypeptide interacts with (e.g., binds to) an RNA to form an RNP (described above). The RNA guides the polypeptide to a target sequence within target DNA (e.g. a chromosomal sequence or an extrachromosomal sequence. e.g. an episomal sequence, a minicircle sequence, a mitochondrial sequence, a chloroplast sequence, etc.). Thus, in some embodiments a chimeric polypeptide binds target DNA.

A chimeric or fusion polypeptide comprises at least two portions, e.g., an RNA binding portion and an "activity" portion (e.g., a label). A chimeric or fusion polypeptide comprises amino acid sequences that are derived from at least two different polypeptides. A chimeric or fusion polypeptide can comprise modified and/or naturally occurring polypeptide sequences (e.g., a first amino acid sequence from a modified or unmodified Cas9/Csn1 protein; and a second amino acid sequence other than the Cas9/Csn1 protein. e.g., a BE27 domain).

In some embodiments, the RNA-binding portion of a chimeric polypeptide is a naturally-occurring polypeptide. In some embodiments, the RNA-binding portion of a chimeric polypeptide is not a naturally-occurring molecule (e.g., modified with respect to a naturally-occurring polypeptide by, e.g., substitution, deletion, insertion). In some embodiments, naturally-occurring RNA-binding portions of interest are derived from polypeptides known in the art, e.g., discussed herein (e.g., Cas9 and similar polypeptides).

In some embodiments, the RNA-binding portion of a chimeric polypeptide comprises an amino acid sequence having at least about 75%, at least about 80%, at least about 85%, at least about 90%, at least about 95%, at least about 98%, at least about 99%, or 100% amino acid sequence identity to the RNA-binding portion of a polypeptide described herein.

In some embodiments, the chimeric polypeptide comprises an amino acid sequence having at least about 75%, at least about 80%, at least about 85%, at least about 90%, at least about 95%, at least about 99%, or 100% amino acid sequence identity to a portion of a Cas9 amino acid sequence provided herein.

In addition to the RNA-binding portion, the chimeric polypeptide comprises an "activity portion", e.g., a BE27 domain.

A gRNA comprises a first segment (also referred to herein as a "DNA-targeting segment" or a "DNA-targeting sequence") and a second segment (also referred to herein as a "protein-binding segment" or a "protein-binding sequence").

The DNA-targeting segment of a gRNA comprises a nucleotide sequence that is complementary to a sequence in a target DNA. In other words, the DNA-targeting segment of a gRNA interacts with a target DNA in a sequence-specific manner via hybridization (e.g., complementary base pairing). As such, the nucleotide sequence of the DNA targeting segment may vary and determines the location within the target DNA that the DNA targeting RNA and the target DNA will interact. The DNA-targeting segment of a gRNA can be modified (e.g., by genetic engineering) to hybridize to any desired sequence within a target DNA.

The DNA-targeting segment (e.g., comprising the DNA-targeting sequence and, in some embodiments, additional nucleic acid) can have a length of from about 8 nucleotides to about 100 nucleotides. For example, the DNA-targeting segment can have a length of from about 12 nucleotides (nt) to about 80 nt, from about 12 nt to about 50 nt, from about 12 nt to about 40 nt, from about 12 nt to about 30 nt, from about 12 nt to about 25 nt, from about 12 nt to about 20 nt, or from about 12 nt to about 19 nt. For example, the DNA-targeting segment can have a length of from about 19 nt to about 20 nt, from about 19 nt to about 25 nt, from about 19 nt to about 30 nt, from about 19 nt to about 35 nt, from about 19 nt to about 40 nt, from about 19 nt to about 45 nt, from about 19 nt to about 50 nt, from about 19 nt to about 60 nt, from about 19 nt to about 70 nt, from about 19 nt to about 80 nt, from about 19 nt to about 90 nt, from about 19 nt to about 100 nt, from about 20 nt to about 25 nt, from about 20 nt to about 30 nt, from about 20 nt to about 35 nt, from about 20 nt to about 40 nt, from about 20 nt to about 45 nt, from about 20 nt to about 50 nt, from about 20 nt to about 60 nt, from about 20 nt to about 70 nt, from about 20 nt to about 80 nt, from about 20 nt to about 90 nt, or from about 20 nt to about 100 nt.

In some embodiments, the nucleotide sequence (the DNA-targeting sequence) of the DNA-targeting segment that is complementary to a nucleotide sequence (target sequence) of the target DNA can have a length at least about 12 nt. For example, the DNA-targeting sequence of the DNA-targeting segment that is complementary to a target sequence of the target DNA can have a length at least about 12 nt, at least about 15 nt, at least about 18 nt, at least about 19 nt, at least about 20 nt, at least about 25 nt, at least about 30 nt, at least about 35 nt or at least about 40 nt. For example, the DNA-targeting sequence of the DNA-targeting segment that is complementary to a target sequence of the target DNA can have a length of from about 12 nucleotides (nt) to about 80 nt, from about 12 nt to about 50 nt, from about 12 nt to about 45 nt, from about 12 nt to about 40 nt, from about 12 nt to about 35 nt, from about 12 nt to about 30 nt, from about 12 nt to about 25 nt, from about 12 nt to about 20 nt, about 12 nt to about 19 nt, from about 19 nt to about 20 nt, from about 19 nt to about 25 nt, from about 19 nt to about 30 nt, from about 19 nt to about 35 nt, from about 19 nt to about 40 nt, from about 19 nt to about 45 nt, from about 19 nt to about 50 nt, from about 19 nt to about 60 nt, from about 20 nt to about 25 nt, from about 20 nt to about 30 nt, from about 20 nt to about 35 nt, from about 20 nt to about 40 nt, from about 20 nt to about 45 nt, from about 20 nt to about 50 nt, or from about 20 nt to about 60 nt. The nucleotide sequence (the DNA-targeting sequence) of the DNA-targeting segment that is complementary to a nucleotide sequence (target sequence) of the target DNA can have a length at least about 12 nt.

In additional embodiments, the nucleotide sequence (the DNA-targeting sequence) of the DNA-targeting segment that is complementary to a nucleotide sequence (target sequence) of the target DNA can have a length of from about 8 nucleotides to about 30 nucleotides. For example, the DNA-targeting segment can have a length of from about 8 nucleotides (nt) to about 30 nt, from about 8 nt to about 30 nt, from about 8 nt to about 25 nt, from about 8 nt to about 20 nt, from about 8 nt to about 18 nt, from about 8 nt to about 15 nt, or from about 8 nt to about 12 nt, e.g., 8 nt, 9 nt, 10 nt, 11 nt, or 12 nt.

In some embodiments, the DNA-targeting sequence of the DNA-targeting segment that is complementary to a target sequence of the target DNA is 8-20 nucleotides in length. In some embodiments, the DNA-targeting sequence of the DNA-targeting segment that is complementary to a target sequence of the target DNA is 9-12 nucleotides in length.

The percent complementarity between the DNA-targeting sequence of the DNA-targeting segment and the target sequence of the target DNA can be at least 60% (e.g., at least 65%, at least 70%, at least, 75%, at least 80%, at least 85%, at least 90%, at least 95%, at least 97%, at least, 98%, at least 99%, or 100%). In some embodiments, the percent complementarity between the DNA-targeting sequence of the DNA-targeting segment and the target sequence of the target DNA is 100% over the seven contiguous 5'-most nucleotides of the target sequence of the complementary strand of the target DNA. In some embodiments, the percent complementarity between the DNA-targeting sequence of the DNA-targeting segment and the target sequence of the target DNA is at least 60% over about 20 contiguous nucleotides. In some embodiments, the percent complementarity between the DNA-targeting sequence of the DNA-targeting segment and the target sequence of the target DNA is 100% over the fourteen contiguous 5'-most nucleotides of the target sequence of the complementary strand of the target DNA and as low as 0% over the remainder. In such a case, the DNA-targeting sequence can be considered to be 14 nucleotides in length. In some embodiments, the percent complementarity between the DNA targeting sequence of the DNA-targeting segment and the target sequence of the target DNA is 100% over the seven contiguous 5'-most nucleotides of the target sequence of the complementary strand of the target DNA and as low as 0% over the remainder. In such a case, the DNA-targeting sequence can be considered to be 7 nucleotides in length.

The protein-binding segment of a gRNA interacts with a polypeptide, e.g., a Cas9, Cas9-BE27, or Cas9-like polypeptide. The gRNA guides the bound polypeptide to a specific nucleotide sequence within target DNA via the above mentioned DNA-targeting segment. The protein-binding segment of a gRNA comprises two segments comprising nucleotide sequences that are complementary to one another. The complementary nucleotides of the protein-binding segment hybridize to form a double stranded RNA duplex.

A dgRNA comprises two separate RNA molecules. Each of the two RNA molecules of a dgRNA comprises a segment is complementary to one another such that the complementary nucleotides of the two RNA molecules hybridize to form the double stranded RNA duplex of the protein-binding segment.

In some embodiments, the duplex-forming segment of the activator-RNA is at least about 60% identical to one of the activator-RNA (tracrRNA) molecules set forth in U.S. Pat. App. Pub. No. 20170051312, incorporated herein by reference, as SEQ ID NOs: 431-562, or a complement thereof, over a segment of at least 8 contiguous nucleotides. For example, the duplex-forming segment of the activator-RNA (or the DNA encoding the duplex-forming segment of the activator-RNA) is at least about 60% identical, at least about 65% identical, at least about 70% identical, at least about, 75% identical, at least about 80% identical, at least about 85% identical, at least about 90% identical, at least about 95% identical, at least about 98% identical, at least about, 99% identical, or 100% identical, to one of the tracrRNA sequences set forth in U.S. Pat. App. Pub. No. 20170051312, incorporated herein by reference, as SEQ ID NOs: 431-562, or a complement thereof, over a segment of at least 8 contiguous nucleotides.

In some embodiments, the duplex-forming segment of the targeter-RNA is at least about 60% identical to one of the targeter-RNA (crRNA) sequences set forth in U.S. Pat. App. Pub. No. 20170051312, incorporated herein by reference, as SEQ ID NOs: 563-679, or a complement thereof, over a segment of at least 8 contiguous nucleotides. For example, the duplex-forming segment of the targeter-RNA (or the DNA encoding the duplex-forming segment of the targeter-RNA) is at least about 65% identical, at least about 70% identical, at least about 75% identical, at least about 80% identical, at least about 85% identical, at least about 90% identical, at least about 95% identical, at least about 98% identical, at least about 99% identical or 100% identical to one of the crRNA sequences set forth in U.S. Pat. App. Pub. No. 20170051312, incorporated herein by reference, as SEQ ID NOs: 563-679, or a complement thereof, over a segment of at least 8 contiguous nucleotides.

Non-limiting examples of nucleotide sequences that can be included in a two-molecule DNA targeting RNA (dgRNA) include either of the sequences set forth in U.S. Pat. App. Pub. No. 20170051312, incorporated herein by reference, as SEQ ID NOs: 431-562, or complements thereof pairing with any sequences set forth in U.S. Pat. App. Pub. No. 20170051312, incorporated herein by reference, as SEQ ID NOs: 563-679, or complements thereof that can hybridize to form a protein binding segment.

A single-molecule DNA-targeting RNA (sgRNA) comprises two segments of nucleotides (a targeter-RNA and an activator-RNA) that are complementary to one another, are covalently linked by intervening nucleotides ("linkers" or "linker nucleotides"), and hybridize to form the double stranded RNA duplex (dsRNA duplex) of the protein-binding segment, thus resulting in a stem-loop structure. The targeter-RNA and the activator-RNA can be covalently linked via the 3' end of the targeter-RNA and the 5' end of the activator-RNA. Alternatively, targeter-RNA and the activator-RNA can be covalently linked via the 5' end of the targeter-RNA and the 3' end of the activator-RNA.

The linker of a single-molecule DNA-targeting RNA can have a length of from about 3 nucleotides to about 100 nucleotides. For example, the linker can have a length of from about 3 nucleotides (nt) to about 90 nt, from about 3 nucleotides (nt) to about 80 nt, from about 3 nucleotides (nt) to about 70 nt, from about 3 nucleotides (nt) to about 60 nt, from about 3 nucleotides (nt) to about 50 nt, from about 3 nucleotides (nt) to about 40 nt, from about 3 nucleotides (nt) to about 30 nt, from about 3 nucleotides (nt) to about 20 nt or from about 3 nucleotides (nt) to about 10 nt. For example, the linker can have a length of from about 3 nt to about 5 nt, from about 5 nt to about 10 nt, from about 10 nt to about 15 nt, from about 15 nt to about 20 nt, from about 20 nt to about 25 nt, from about 25 nt to about 30 nt, from about 30 nt to about 35 nt, from about 35 nt to about 40 nt, from about 40 nt to about 50 nt, from about 50 nt to about 60 nt, from about 60 nt to about 70 nt, from about 70 nt to about 80 nt, from about 80 nt to about 90 nt, or from about 90 nt to about 100 nt. In some embodiments, the linker of a single molecule DNA-targeting RNA is 4 nt.

An exemplary single-molecule DNA-targeting RNA comprises two complementary segments of nucleotides that hybridize to form a dsRNA duplex. In some embodiments, one of the two complementary segments of nucleotides of the single-molecule DNA-targeting RNA (or the DNA encoding the segment) is at least about 60% identical to one of the activator-RNA (tracrRNA) molecules set forth in U.S. Pat. App. Pub. No. 20170051312, incorporated herein by reference, as SEQ ID NOs: 431-562, or a complement thereof, over a segment of at least 8 contiguous nucleotides. For example, one of the two complementary segments of nucleotides of the single-molecule DNA-targeting RNA (or the DNA encoding the segment) is at least about 65% identical, at least about 70% identical, at least about 75% identical, at least about 80% identical, at least about 85% identical, at least about 90% identical, at least about 95% identical, at least about 98% identical, at least about 99% identical or 100% identical to one of the tracrRNA sequences set forth in U.S. Pat. App. Pub. No. 20170051312, incorporated herein by reference, as SEQ ID NOs: 431-562, or a complement thereof, over a segment of at least 8 contiguous nucleotides.

In some embodiments, one of the two complementary segments of nucleotides of the single molecule DNA-targeting RNA (or the DNA encoding the segment) is at least about 60% identical to one of the targeter-RNA (crRNA) sequences set forth in U.S. Pat. App. Pub. No. 20170051312, incorporated herein by reference, as SEQ ID NOs: 563-679, or a complement thereof, over a segment of at least 8 contiguous nucleotides. For example, one of the two complementary segments of nucleotides of the single-molecule DNA-targeting RNA (or the DNA encoding the segment) is at least about 65% identical, at least about 70% identical, at least about 75% identical, at least about 80% identical, at least about 85% identical, at least about 90% identical, at least about 95% identical, at least about 98% identical, at least about 99% identical or 100% identical to one of the crRNA sequences set forth in U.S. Pat. App. Pub. No. 20170051312, incorporated herein by reference, as SEQ ID NOs: 563-679, or a complement thereof, over a stretch of at least 8 contiguous nucleotides.

With regard to both a sgRNA and a dgRNA, artificial sequences that share a wide range of identity (approximately at least 50% identity) with naturally occurring tracrRNAs and crRNAs function with Cas9 and Cas9-BE27 to deliver RNP to target nucleic acids with sequence specificity, particularly provided that the structure of the protein-binding domain of the DNA targeting RNA is conserved. Thus, information and modeling relating to RNA folding and RNA secondary structure of a naturally occurring protein-binding domain of a DNA-targeting RNA provides guidance to design artificial protein-binding domains (either in dgRNA or sgRNA). As a non-limiting example, a functional artificial DNA-targeting RNA may be designed based on the structure of the protein-binding segment of a naturally occurring DNA-targeting segment of an RNA (e.g., including the same or similar number of base pairs along the RNA duplex and including the same or similar "bulge" region as present in the naturally occurring RNA). Structures can readily be produced by one of ordinary skill in the art for any naturally occurring crRNA:tracrRNA pair from any species; thus, in some embodiments an artificial DNA-targeting-RNA is designed to mimic the natural structure for a given species when using the Cas9 (or a related Cas9) from that species. Thus, in some embodiments a suitable DNA-targeting RNA is an artificially designed RNA (non-naturally occurring) comprising a protein-binding domain that was designed to mimic the structure of a protein-binding domain of a naturally occurring DNA-targeting RNA. In exemplary embodiments, the protein-binding segment has a length of from about 10 nucleotides to about 100 nucleotides; e.g., the protein-binding segment has a length of from about 15 nucleotides (nt) to about 80 nt, from about 15 nt to about 50 nt, from about 15 nt to about 40 nt, from about 15 nt to about 30 nt or from about 15 nt to about 25 nt.

Nucleic acids can be analyzed and designed using a variety of computer tools, e.g., Vector Ni (Invitrogen) for nucleic acids and AlignX for comparative sequence analysis of proteins. Further, in silico modeling of RNA structure and folding can be performed using the Vienna RNA package algorithms and RNA secondary structures and folding models can be predicted with RNAfold and RNAcofold, respectively, and visualized with VARNA. See, e.g., Denman (1993), Biotechniques 15, 1090; Hofacker and Stadler (2006), Bioinformatics 22, 1172; and Darty and Ponty (2009), Bioinformatics 25, 1974, each of which is incorporated herein by reference.

Thus, as described herein, in some embodiments, the technology provides methods, systems, kits, compositions, uses, etc. comprising and/or comprising use of a RNP comprising a polypeptide and one or more RNAs. In some embodiments, the RNA comprises a segment (e.g., comprising 6-10 nucleotides, e.g., comprising 6, 7, 8, 9, or 10 nucleotides) that is complementary (e.g., at least 80, 81, 82, 83, 84, 85, 86, 87, 88, 89, 90, 91, 92, 93, 94, 95, 96, 97, 98, 98.5, 99, 99.1, 99.2, 99.3, 99.4, 99.5, 99.6, 99.7, 99.8, 99.9, or 100% complementary) to a nucleotide sequence in the target DNA.

In some embodiments, the RNA comprises a segment comprising a nucleotide sequence (e.g., a scaffold sequence. e.g., a sequence that interacts with (e.g., binds to) the polypeptide) that is at least 60% identical over at least 8 contiguous nucleotides to any one of the nucleotide sequences set forth in SEQ ID NOs: 431-682 (e.g., SEQ ID NOs: 431-562) of U.S. Pat. App. Pub. No. 20170051312, incorporated herein by reference. In some embodiments, the RNA comprises a nucleotide sequence (e.g., a scaffold sequence. e.g., a sequence that interacts with (e.g., binds to) the polypeptide) that is at least 60% identical over at least 8 contiguous nucleotides to any one of the nucleotide sequences set forth in SEQ ID NOs: 563-682 of U.S. Pat. App. Pub. No. 20170051312, incorporated herein by reference.

In some embodiments, the polypeptide comprises a segment comprising an amino acid sequence that is at least approximately 75% amino acid identical to amino acids 7-166 or 731-1003 of any of the amino acid sequences set forth as SEQ ID NOs: 1-256 and 795-1346 of U.S. Pat. App. Pub. No. 20170051312, incorporated herein by reference.

In some embodiments, the polypeptide comprises a segment comprising an amino acid sequence of the HiFiCas9 or spCas9mSA proteins, e.g., to provide a HiFiCas9-BE27 or spCas9mSA-BE27 fusion protein.

In some embodiments, the technology comprises use of an RNA-targeting protein (e.g., Cas13 and a Cas13-BE27 fusion), which works according to a similar mechanism as Cas9. In addition to targeting genomic DNA. Cas9 and other CRISPR related proteins (e.g. Cas13) also target RNAs directed by gRNAs (see. e.g., Abudayyeh et al. (2017) "RNA targeting with CRISPR-Cas13" Nature 550: 280, incorporated herein by reference). Thus, in some embodiments, gRNAs complex with Cas9 or other RNA-guided nucleases (e.g., a class 2 type VI RNA-guided RNA-targeting CRISPR-Cas effector (e.g., Cas13), a Cpf1, etc.) fused to a BE27 domain to edit RNA transcripts and non-coding RNAs in cells. Accordingly, in some embodiments, the technology relates to targeting RNAs using guide RNAs in complex with a Cas9-BE27 or an RNA-targeting Cas13-BE27 fusion.

Donor Nucleic Acid

In some embodiments, the technology comprises use of a donor nucleic acid. e.g., a DNA molecule. In some embodiments, the donor molecule participates in HDR to "repair" the DSB with a sequence from the donor. In this way, CRISPR finds use to make targeted insertions of a particular nucleic acid sequence at a target site.

In some embodiments, the donor nucleic acid is double stranded. In some embodiments, the donor nucleic acid is single stranded. In some embodiments, a donor DNA molecule is a linear molecule (e.g., not a circular molecule such as a plasmid DNA).

A donor DNA molecule can have any desired sequence. In some embodiments, the donor nucleic acid comprises a portion comprising a nucleic acid to be knocked-in at a target locus (e.g., in some embodiments, the donor nucleic acid comprises a portion comprising an insertion sequence). In some embodiments, the 3' most nucleotide on at least one end of the donor DNA molecule is a C. In some embodiments, the 3' most nucleotide on one and only one end of the donor DNA molecule is a C. In some embodiments, the 3' most nucleotide on at least one end of the donor DNA molecule is a G. In some embodiments, the 3' most nucleotide on one and only one end of the donor DNA molecule is a G. In some embodiments, the 3' most nucleotide on at least one end of the donor DNA molecule is an A. In some embodiments, the 3' most nucleotide on one and only one end of the donor DNA molecule is an A. In some embodiments, the 3' most nucleotide on at least one end of the donor DNA molecule is a T. In some embodiments, the 3' most nucleotide on one and only one end of the donor DNA molecule is a T.

In some embodiments, the linear donor (e.g., DNA) molecule has a length in a range of from 10 to 1000 nucleotides (nt) (e.g., 15 to 500, 20 to 500, 30 to 500, 33 to 500, 35 to 500, 40 to 500, 45 to 500, 50 to 500, 15 to 250, 20 to 250, 30 to 250, 33 to 250, 35 to 250, 40 to 250, 45 to 250, 50 to 250, 15 to 150, 20 to 150, 30 to 150, 33 to 150, 35 to 150, 40 to 150, 45 to 150, 50 to 150, 15 to 100, 20 to 100, 30 to 100, 33 to 100, 35 to 100, 40 to 100, 45 to 100, 50 to 100, 15 to 50, 20 to 50, 30 to 50, 33 to 50, 35 to 50, 40 to 50, or 45 to 50 nt). In some embodiments, the linear donor nucleic acid has a length of 1 Kbp or more (e.g., 1 to 10 Kbp (e.g., 1, 1.5, 2, 2.5, 3, 3.5, 4, 4.5, 5, 5.5, 6, 6.5, 7, 7.5, 8, 8.5, 9, 9.5, or 10 Kbp).

In some embodiments, a subject method includes introducing into a cell a subject linear donor DNA molecule. In some embodiments, a donor DNA molecule includes a label (e.g., as defined above, e.g., a biotin label, a fluorescent dye, etc.).

In some embodiments, the linear donor DNA molecule includes a 3'-overhang. For example, In some embodiments, the linear donor DNA molecule includes a 3'-overhang having a length in a range of from 1 to 6 nucleotides (nt) (e.g., 1 to 5 nt, 1 to 4 nt, 1 to 3 nt, 1 to 2 nt, 2 to 6 nt, 2 to 5 nt, 2 to 4 nt, 2 to 3 nt, 3 to 6 nt, 3 to 5 nt, 3 to 4 nt, 4 to 6 nt, 4 to 5 nt, 5 to 6 nt, 1 nt, 2 nt, 3 nt, 4 nt, 5 nt, or 6 nt). In some embodiments, the linear donor DNA molecule does not have a 3'-overhang. Thus, In some embodiments, the linear donor DNA molecule includes a 3'-overhang having a length in a range of from 0 to 6 nucleotides (nt) (e.g., 0 to 5 nt, 0 to 4 nt, 0 to 3 nt, 0 to 2 nt, 0 to 1 nt, 1 to 6 nt, 1 to 5 nt, 1 to 4 nt, 1 to 3 nt, 1 to 2 nt, 2 to 6 nt, 2 to 5 nt, 2 to 4 nt, 2 to 3 nt, 3 to 6 nt, 3 to 5 nt, 3 to 4 nt, 4 to 6 nt, 4 to 5 nt, 5 to 6 nt, 1 nt, 2 nt, 3 nt, 4 nt, 5 nt, or 6 nt).

Synthesis and Assembly of RNP and Delivery of RNP

In some embodiments, the fusion protein is synthesized, purified, and assembled in vitro. In some embodiments, the gRNA is transcribed in vitro. In some embodiments, the gRNA is chemically synthesized de novo. In some embodiments, the RNP complex is assembled in vitro using in vitro-transcribed, or de novo-synthesized single guide RNA (sgRNA) and a protein that is synthesized, purified, and folded in vitro.

In some embodiments, an expression system (e.g., comprising an expression vector and a suitable expression host) finds use in producing a polypeptide and/or the RNA of the RNP. Numerous suitable expression vectors are known to those of skill in the art, and many are commercially available. The following vectors are provided by way of example; for eukaryotic host cells; pXT1, pSG5 (Stratagene), pSVK3, pBPV, pMSG, and pSVLSV40 (Pharmacia). However, any other vector may be used so long as it is compatible with the host cell. Depending on the host/vector system utilized, any of a number of suitable transcription and translation control elements, including constitutive and inducible promoters, transcription enhancer elements, transcription terminators, etc. may be used in the expression vector (see e.g., Bitter et al. (1987) Methods in Enzymology, 153: 516-544, incorporated herein by reference).

In some embodiments, the protein is provided as a single polypeptide (e.g., a full gene editing nuclease-BE27 fusion). In some embodiments, the protein is provided in multiple polypeptides, e.g., a split gene editing nuclease-BE27 fusion protein provided in two parts, three parts, etc.

In some embodiments, the RNP is provided as a nanoparticle for administration to a live organism.

In some embodiments, the RNP is delivered into cells using a technique or composition related to nucleofection, cell penetrating peptide, viral vesicles, cell surface tunneling protein, ultrasound, electroporation, cell squeezing, nanoparticles, gold or other metal particles, lipid particles, liposomes, viral transduction, viral particles, cell-cell fusion, ballistics, microinjection, and exosome intake.

In some embodiments, the gene editing nuclease-BE27 fusion protein comprises a nuclear localization signal (NLS), e.g., an SV40 NLS, to direct the RNP to enter a nucleus. In some embodiments, the protein (e.g., gene editing nuclease-BE27 fusion) comprises an importin beta binding (IBB) domain sequence. e.g., to promote import of the polypeptide into a cell nucleus, e.g., by an importin (see, e.g., Lott and Cingolani (2011), Biochim Biophys Acta 1813(9): 1578-92, incorporated herein by reference).

In some embodiments, an RNA is introduced into a cell that expresses a gene editing nuclease-BE27 fusion. In some embodiments, crRNA/tracrRNA complexes (e.g., comprising a crRNA and/or a trarcrRNA) are introduced into cells stably expressing a gene editing nuclease-BE27 fusion. In some embodiments, labeled sgRNA is introduced into cells stably expressing a gene editing nuclease-BE27 fusion.

Gene Editing Nucleases

In some embodiments, the technology comprises use of a gene editing nuclease-BE27 fusion comprising a TALEN, meganuclease, ZFN, etc. fused to one or more BE27 domains. In some embodiments, a TALEN, meganuclease, or ZFN is fused to a plurality of BE27 domains (e.g., 1, 2, 3, 4, 5, 6, 7, 8, 9, 10, 11, 12, 13, 14, 15, 16, 17, 18, 19, 20, 21, 22, 23, 24, or 25 or more BE27 domains). In some embodiments, a polypeptide comprises a gene editing nuclease (e.g., a TALEN, meganuclease. ZFN, etc.) and a plurality of BE27 domains arranged serially, e.g., in a tandem array. In some embodiments, a polypeptide comprises a gene editing nuclease (e.g., a TALEN, meganuclease. ZFN, etc.) fused to a plurality of BE27 domains separated by one or more linker sequences (e.g., separating one or more of the plurality of the BE27 domains).

In some embodiments, the technology comprises compositions, methods, kits, and systems comprising and/or comprising use of a TALEN-BE27 to facilitate and/or stabilize the assembly of RAD51 at DSB to further improve the HR rate. In particular, the technology comprises a TALEN in which the FokI is replaced with one or more BE27 domains as described herein.

ZFN, TALEN, and CRISPR/Cas9 are efficient in generating DSBs in the genome that can lead to a functional knockout of the targeted gene or used to integrate a DNA sequence at a specific locus (KI) in the genome in a number of species (see, e.g., Carlson et al. (2012) "Efficient TALEN-mediated gene knockout in livestock" Proceedings of the National Academy of Sciences of the United States of America 109(43): 17382-87; Clark et al. (2011) "A TALE of two nucleases; gene targeting for the masses?" Zebrafish 8(3): 147-49, each of which is incorporated herein by reference). Similarly to DSB produced by CRISPR proteins, NHEJ and HDR function to repair DSBs produced by TALEN and ZFN. Further, in NHEJ, the break ends are directly ligated without the need for a homologous template, thus lead to generally unpredictable insertions or deletions (indels) at the targeting sites. HDR may take place, in addition to NHEJ, when homologous donor templates are present, leading to correct repair or knock-in events. Data collected during the development of embodiments of the technology indicated that ZFN and Cas9 produced KO in rabbits (see. e.g., Yang et al. (2014) "Effective gene targeting in rabbits using RNA-guided Cas9 nucleases" J Mol Cell Biol 6(1): 97-99; Yang et al. (2013) "Production of apolipoprotein C-III knockout rabbits using zinc finger nucleases" Journal of visualized experiments: JoVE (81): e50957, each of which is incorporated herein). The KO rates using the Cas9 system ranged from 10-100% in vitro and 32.1-83.3% in vivo (id). However, the frequency of HDR appears to be much lower than that of NHEJ. Without any intervention, the HDR/NHEJ ratio calculated by the number of indel events over that of knock-in events was below 10% in the rabbit system, consistent with reports in other species. For example, Gonzalez et al reported 2-3% HDR rates vs. 13-49% indel rates in human ES and iPS cells in 2014 (see, e.g., Zhu et al. (2014) "The iCRISPR platform for rapid genome editing in human pluripotent stem cells" Methods in enzymology 546: 215-250, incorporated herein by reference). Likewise, in one mouse study, the NHEJ mediated gene editing was 28-50%, whereas the HDR-mediated knock-in was below 10% (Wang et al. (2013) "One-step generation of mice carrying mutations in multiple genes by CRISPR/Cas-mediated genome engineering" Cell 153(4): 910-918, incorporated herein by reference). Collectively, the HDR events take place at 1/3 or even lower rates than the NHEJ events.

Such low knock-in rate has become a bottleneck problem for the broad application of customizable nuclease systems (e.g., TALEN, Cas9, and ZFN) in biomedical research, because for reliable disease modeling and gene correction it is often necessary that a specific change be introduced to the sequence. Even for gene addition therapy, it is desirable that such addition is location and copy number controlled, which has been demonstrated by knock-in to the ROSA26 or similar safe harbor locus. Accordingly, provided herein are TALEN-BE27 gene fusions, methods of using TALEN-BE27 gene fusions, kits comprising. TALEN-BE27 gene fusions, and systems comprising TALEN-BE27 gene fusions. Accordingly, also provided herein are ZFN-BE27 gene fusions, methods of using ZFN-BE27 gene fusions, kits comprising ZFN-BE27 gene fusions, and systems comprising ZFN-BE27 gene fusions.

Methods

In some embodiments, the technology provided herein relates to methods for genetically editing a target DNA (e.g., producing a knockin). e.g., in a cell (e.g., a living cell, e.g., a living primary cell). In some embodiments, a method comprises contacting a target with a gene editing nuclease-BE27 fusion. In some embodiments, a method involves contacting a target DNA with a RNP complex (a "targeting complex"), which complex comprises a DNA-targeting RNA and a gene editing nuclease-BE27 fusion (e.g., a Cas9-BE27 fusion), and a donor nucleic acid comprising a nucleic acid to insert at the target locus. In some embodiments, the donor nucleic acid is a targeting vector and/or a single-stranded nucleic acid comprising the nucleic acid to insert at the target locus flanked by nucleic acid complementary to the target site ("homology arms").

In some embodiments for introducing small insertions (e.g., an insert less than approximately 50 bp, e.g., (50, 45, 40, 35, 30, 25, 20, 15, 10, 5, or 2 basepairs) or a single point mutation (e.g., 1 bp), the technology comprises use of a single stranded DNA (ssDNA) oligonucleotide as the donor nucleic acid (e.g., for transfection into the target cell). In some embodiments, the ssDNA oligonucleotide comprises approximately 100-150 bp of identity and/or high homology with the target site flanking the small insert or point mutation, thus providing approximately 50-75 bp to each "homology arm" flanking each side of the mutation. In some embodiments, for introducing large insertions (e.g., insertions or deletions comprising more than approximately 50, approximately 100 bp, approximately 1000 bp or more), a plasmid is typically used as the donor nucleic acid. In some embodiments for introducing large insertions, two homology arms comprising approximately 300 to 800 bp flank the desired insertion or mutation. In some embodiments, the size of such a plasmid donor is approximately 5 Kbp (see, e.g., Yang et al., Cell 154(6): 1370-1379, 2013, incorporated herein by reference). In some embodiments, homology arms that are 800 bp in length are used for efficient knockin of a 1 Kbp fragment.

In some embodiments, the donor construct is introduced into the cell in the form of a linear nucleic acid or cleaved within the cell to produce a linear nucleic acid. In some embodiments, it is delivered by any method appropriate for introducing nucleic acids into a cell. For example, the donor construct can be introduced into the cell by a variety of means known in the art, including transfection, calcium phosphate-DNA co-precipitation. DEAE-dextran-mediated transfection, polybrene-mediated transfection, electroporation, microinjection, transduction, cell fusion, liposome fusion, lipofection, protoplast fusion, retroviral infection, use of a gene gun, use of a DNA vector transporter, and biolistics (e.g., particle bombardment) (See e.g., Wu et al., 1992. J. Biol. Chem., 267:963-967; Wu and Wu, 1988, J. Biol. Chem., 263:14621-14624; and Williams et al., 1991, Proc. Natl. Acad. Sci. USA 88:2726-2730). Receptor-mediated DNA delivery approaches can also be used (Curiel et al., 1992, Hum. Gene Ther., 3:147-154; and Wu and Wu, 1987, J. Biol. Chem., 262:4429-4432).

As discussed herein, a DNA-targeting RNA and a polypeptide (a gene editing nuclease-BE27 fusion (e.g., a Cas9-BE27 fusion)) form a ribonucleoprotein (RNP) complex. The DNA-targeting RNA provides target specificity to the RNP complex by comprising a nucleotide sequence that is complementary to a sequence of a target DNA. The polypeptide (a gene editing nuclease-BE27 fusion (e.g., a Cas9-BE27 fusion)) of the RNP complex provides the site-specific activity. In some embodiments, a RNP complex produces a DSB in a target DNA. The target DNA may be, for example, naked DNA in vitro, chromosomal DNA in cells in vitro, chromosomal DNA in cells in vivo, etc.

In some embodiments, the RNP complex produces a DSB in a target DNA at a target DNA sequence defined by the region of complementarity between the DNA-targeting RNA and the target DNA. In some embodiments, when the polypeptide is a gene editing nuclease-BE27 fusion (e.g., a Cas9-BE27 fusion), site-specific nuclease activity produces DSB in the target DNA at locations determined by both (i) base-pairing complementarity between the DNA targeting RNA and the target DNA; and ii) a short, motif (referred to as the protospacer adjacent motif (PAM)) in the target DNA. In some embodiments (e.g., when Cas9 from *S. pyogenes*, or a closely related Cas9, is used), the PAM sequence of the non-complementary strand is 5'-XGG-3', where X is any DNA nucleotide and X is immediately 3' of the target sequence of the non-complementary strand of the target DNA. As such, the PAM sequence of the complementary strand is 5'-CCY-3', where Y is any DNA nucleotide and Y is immediately 5' of the target sequence of the complementary strand of the target DNA. In some such embodiments, X and Y can be complementary and the X-Y base pair can be any base pair (e.g., X=C and Y=G; X=G and Y=C; X=A and Y=T, X=T and Y=A). In some embodiments, the RNP has no requirement for a PAM sequence.

In some embodiments, methods comprise a step of producing a polypeptide (e.g., a gene editing nuclease-BE27 fusion (e.g., a gene editing nuclease-BE27 fusion (e.g., a Cas9-BE27 fusion) and/or a modified variant thereof))) in vitro. In some embodiments, methods comprise a step of producing a nucleic acid in vitro, e.g., an RNA, e.g., one or more of a tracrRNA, a crRNA, and/or a sgRNA. In some embodiments, methods comprise a step of folding and/or assembling RNA (e.g., folding and/or annealing a tracrRNA and a crRNA; folding a sgRNA, folding and/or annealing a dgRNA). In some embodiments, methods comprise a step of assembling a RNP complex in vitro, e.g., a RNP comprising a polypeptide (e.g., a gene editing nuclease-BE27 fusion (e.g., a Cas9-BE27 fusion)) and one or more RNA molecules. In some embodiments, methods comprise a step of introducing a RNP into a cell (e.g., a living cell. e.g., a living primary cell).

In some embodiments, multiple DNA-targeting RNAs and/or multiple RNPs are used simultaneously to simultaneously modify (e.g., by knockin) different nucleic acid sequences on the same target DNA or on different target DNAs, e.g., to provide a multiplex method. In some embodiments, two or more DNA-targeting RNAs target the same gene or transcript or locus. In some embodiments, two or more DNA-targeting RNAs target different unrelated loci. In some embodiments, two or more DNA-targeting RNAs target different, but related loci.

In some embodiments, the polypeptide (e.g., a gene editing nuclease-BE27 fusion (e.g., a gene editing nuclease-BE27 fusion (e.g., a Cas9-BE27 fusion) and/or a modified variant thereof))) is provided directly as a protein. In some embodiments, a nucleic acid is introduced into a cell and the polypeptide (e.g., a gene editing nuclease-BE27 fusion (e.g., a gene editing nuclease-BE27 fusion (e.g., a Cas9-BE27 fusion) and/or a modified variant thereof)) is expressed from the nucleic acid in the cell. As one non-limiting example, fungi (e.g., yeast) can be transformed with exogenous protein, nucleic acid, and/or RNP complexes using spheroplast transformation (see Kawai et al., Bioeng Bugs. 2010 Nov-Dec; 1(6):395-403: "Transformation of *Saccharomyces cerevisiae* and other fungi: methods and possible underlying mechanism"; and Tanka et al., Nature. 2004 Mar. 18; 428 (6980):323-8: "Conformational variations in an infectious protein determine prion strain differences"; each of which is herein incorporated by reference). Thus, a polypeptide (e.g., a gene editing nuclease-BE27 fusion (e.g., a gene editing nuclease-BE27 fusion (e.g., a Cas9-BE27 fusion) and/or a modified variant thereof))), nucleic acid (e.g., RNA), and/or a RNP can be incorporated into a spheroplast and the spheroplast can be used to introduce the RNP into a yeast cell. A RNP can be introduced into a cell (provided to the cell) by any convenient method; such methods are known to those of ordinary skill in the art. As another non-limiting example, a RNP can be injected directly into a cell, e.g., a human cell, a cell of a zebrafish embryo, the pronucleus of a fertilized mouse oocyte, etc.

In some embodiments, a subject method includes a step of introducing into a target cell (e.g., a eukaryotic cell) one or more nucleic acids (e.g., a subject donor DNA molecule, a nucleic acid that includes nucleotide sequences encoding a gene editing nuclease-BE27 fusion, etc.). Methods of introducing a nucleic acid into a cell are known in the art and any convenient method can be used (e.g., electroporation, lipofection, nucleofection, injection, viral vectors, etc.). In some embodiments, a subject DNA molecule is introduced into a cell in a composition that also includes a gene editing nuclease-BE27 fusion.

When one or more nucleic acids are used that include nucleotides encoding a gene editing nuclease-BE27 fusion, the sequence encoding the gene editing nuclease-BE27 fusion can be codon-optimized. A sequence encoding any suitable gene editing nuclease-BE27 fusion can be codon optimized. As a non-limiting example, if the intended host cell were a mouse cell, then a mouse codon-optimized nucleotide sequence encoding a gene editing nuclease-BE27 fusion (or variant thereof) would be suitable. While codon optimization is not required, it is acceptable and may be preferable in certain cases.

In some embodiments, one or more of the above nucleic acids are a recombinant expression vector. In some embodiments, the recombinant expression vector is a viral construct, e.g., a recombinant adeno-associated virus construct (see, e.g., U.S. Pat. No. 7,078,387), a recombinant adenoviral construct, a recombinant lentiviral construct, a recombinant retroviral construct, etc.

Suitable expression vectors include, but are not limited to, viral vectors (e.g. viral vectors based on vaccinia virus; poliovirus; adenovirus (see. e.g., Li et al., Invest Opthalmol Vis Sci 35:2543 2549, 1994; Borras et al., Gene Ther 6:515 524, 1999; Li and Davidson, PNAS 92:7700 7704, 1995; Sakamoto et al., H Gene Ther 5:1088 1097, 1999; WO 94/12649, WO 93/03769; WO 93/19191; WO 94/28938; WO 95/11984 and WO 95/00655); adeno-associated virus (see, e.g., Ali et al., Hum Gene Ther 9:81 86, 1998, Flannery et al., PNAS 94:6916 6921, 1997; Bennett et al., Invest Opthalmol Vis Sci 38:2857 2863, 1997; Jomary et al., Gene Ther 4:683 690, 1997, Rolling et al., Hum Gene Ther 10:641 648, 1999; Ali et al., Hum Mol Genet 5:591 594, 1996; Srivastava in WO 93/09239. Samulski et al., J. Vir. (1989) 63:3822-3828; Mendelson et al., Virol. (1988) 166:154-165; and Flotte et al., PNAS (1993) 90:10613-10617); SV40; herpes simplex virus; human immunodeficiency virus (see, e.g., Miyoshi et al., PNAS 94:10319 23, 1997: Takahashi et al., J Virol 73:7812 7816, 1999); a retroviral vector (e.g., Murine Leukemia Virus, spleen necrosis virus, and vectors derived from retroviruses such as Rous Sarcoma Virus, Harvey Sarcoma Virus, avian leukosis virus, a lentivirus, human immunodeficiency virus, myeloproliferative sarcoma virus, and mammary tumor virus); and the like.

Numerous suitable expression vectors are known to those of skill in the art, and many are commercially available. The following vectors are provided by way of example; for eukaryotic host cells: pXT1, pSG5 (Stratagene), pSVK3, pBPV, pMSG, and pSVLSV40 (Pharmacia). However, any other vector may be used so long as it is compatible with the host cell.

Depending on the host/vector system utilized, any of a number of suitable transcription and translation control elements, including constitutive and inducible promoters, transcription enhancer elements, transcription terminators, etc. may be used in the expression vector (see e.g., Bitter et al. (1987) Methods in Enzymology. 153:516-544).

In some embodiments, a nucleotide sequence encoding gene editing nuclease-BE27 fusion is operably linked to a control element, e.g., a transcriptional control element, such as a promoter. The transcriptional control element may be functional in either a eukaryotic cell, e.g., a mammalian cell; or a prokaryotic cell (e.g., bacterial or archaeal cell) (e.g. in cases where a gene editing nuclease-BE27 fusion protein will be isolated/purified prior to the contacting step). In some embodiments, a nucleotide sequence encoding a gene editing nuclease-BE27 fusion protein is operably linked to multiple control elements that allow expression of the nucleotide sequence encoding a gene editing nuclease-BE27 fusion protein in both prokaryotic and eukaryotic cells.

Non-limiting examples of suitable eukaryotic promoters (promoters functional in a eukaryotic cell) include those from cytomegalovirus (CMV) immediate early, herpes simplex virus (HSV) thymidine kinase, early and late SV40, long terminal repeats (LTRs) from retrovirus, and mouse metallothionein-I. Selection of the appropriate vector and promoter is well within the level of ordinary skill in the art. In some embodiments, a promoter is chosen to achieve a desirable level expression (e.g., which, in some embodiments, can be as high as possible, whereas in some embodiments may be above or below a desirable threshold, e.g., to achieve the desired goal while reducing off-target effects). The expression vector may also contain a ribosome binding site for translation initiation and a transcription terminator. The expression vector may also include appropriate sequences for amplifying expression. The expression vector may also include nucleotide sequences encoding protein tags (e.g., 6.times. His tag, hemagglutinin tag, green fluorescent protein, etc.) that are fused to gene editing nuclease-BE27 fusion protein, thus resulting in one nor more chimeric polypeptides.

In some embodiments, a nucleotide sequence encoding a gene editing nuclease-BE27 fusion protein is operably linked to an inducible promoter. In some embodiments, a nucleotide sequence encoding a gene editing nuclease-BE27 fusion protein is operably linked to a constitutive promoter.

Methods of introducing a nucleic acid into a host cell are known in the art, and any known method can be used to introduce a nucleic acid (e.g., an expression construct) into a cell. Suitable methods include e.g., viral or bacteriophage infection, transfection, conjugation, protoplast fusion, lipofection, electroporation, calcium phosphate precipitation, polyethyleneimine (PEI)-mediated transfection, DEAE-dextran mediated transfection, liposome-mediated transfection, particle gun technology, calcium phosphate precipitation, direct micro injection, nanoparticle-mediated nucleic acid delivery (see, e.g., Panyam et., al Adv Drug Deliv Rev. 2012 Sep. 13.), and the like.

Cells

In some embodiments of the technology provided herein, the technology finds use to modify (e.g., by knockin) nucleic acids in mitotic or post-mitotic cells in vivo and/or ex vivo and/or in vitro. Because the DNA-targeting RNA provides specificity by hybridizing to target DNA, a mitotic and/or post-mitotic cell of interest in the disclosed methods may include a cell from any organism (e.g., a bacterial cell, an archaeal cell, a cell of a single-cell eukaryotic organism, a plant cell, an algal cell, e.g., *Botryococcus braunii, Chlamydomonas reinhardtii, Nannochloropsis gaditana, Chlorella pyrenoidosa, Sargassum patens C. Agardh*, and the like, a fungal cell (e.g., a yeast cell), an animal cell, a cell from an invertebrate animal (e.g. fruit fly, cnidarian, echinoderm, nematode, etc.), a cell from a vertebrate animal (e.g., fish, amphibian, reptile, bird, mammal), a cell from a mammal, a cell from a rodent, a cell from a human, etc.).

Any type of cell may be of interest (e.g. a stem cell, e.g. an embryonic stem (ES) cell, an induced pluripotent stem UPS) cell, a germ cell; a somatic cell, e.g. a fibroblast, a hematopoietic cell, a neuron, a muscle cell, a bone cell, a hepatocyte, a pancreatic cell; an in vitro or in vivo embryonic cell of an embryo at any stage. e.g., a 1-cell, 2-cell, 4-cell, 8-cell, etc. stage zebrafish embryo; etc.). Cells may be from established cell lines or they may be primary cells, where "primary cells", "primary cell lines", and "primary cultures" are used interchangeably herein to refer to cells and cells cultures that have been derived from a subject and allowed to grow in vitro for a limited number of passages (e.g, "splittings") of the culture. For example, primary cultures are cultures that may have been passaged 0 times, 1 time, 2 times, 4 times, 5 times, 10 times, or 15 times, but not enough times go through the crisis stage. Typically, the primary cell lines of the present invention are maintained for fewer than 10 passages in vitro. Target cells are in many embodiments unicellular organisms or are grown in culture.

In some embodiments, primary cells are obtained from an individual by any convenient method. For example, leukocytes may be conveniently obtained by apheresis, leukocytapheresis, density gradient separation, etc., while cells from tissues such as skin, muscle, bone marrow, spleen, liver, pancreas, lung, intestine, stomach, etc. are most conveniently obtained by biopsy. An appropriate solution may be used for dispersion or suspension of the obtained cells. Such solution will generally be a balanced salt solution, e.g. normal saline, phosphate-buffered saline (PBS), Hank's balanced salt solution, etc., conveniently supplemented with fetal calf serum or other naturally occurring factors, in conjunction with an acceptable buffer at low concentration, generally from 5-25 mM. Convenient buffers include HEPES, phosphate buffers, lactate buffers, etc. The cells may be used immediately, or they may be stored, frozen, for long periods of time, being thawed and capable of being reused. In such cases, the cells will usually be frozen in 10% DMSO, 50% serum, 40% buffered medium, or some other such solution as is commonly used in the art to preserve cells at such freezing temperatures, and thawed in a manner as commonly known in the art for thawing frozen cultured cells.

Samples

In some embodiments, nucleic acids (e.g., DNA or RNA, e.g., chromosomes, genes, genetic loci, genetic markers, etc.) are obtained, derived, and/or isolated from a biological sample containing a variety of other components, such as proteins, lipids, and non-target nucleic acids. In some embodiments, samples are obtained from and/or comprise and/or are derived or prepared from a variety of materials (e.g., cellular material (live or dead), extracellular material, viral material, environmental samples (e.g., metagenomic samples), synthetic material (e.g., amplicons such as provided by PCR or other amplification technologies)), obtained from an animal, plant, bacterium, archaeon, fungus, or any other organism. Biological samples for use in the present technology include viral particles or preparations thereof. In some embodiments, sample are obtained directly from an organism or from a biological sample obtained from an organism, e.g., blood, urine, cerebrospinal fluid, seminal fluid, saliva, sputum, stool, hair, sweat, tears, skin, amniotic fluid, and tissue (e.g., umbilical tissue). Exemplary samples include, but are not limited to, whole blood, lymphatic fluid, serum, plasma, buccal cells, sweat, tears, saliva, sputum, hair, skin, biopsy, cerebrospinal fluid (CSF), amniotic fluid, seminal fluid, vaginal excretions, serous fluid, synovial fluid, pericardial fluid, peritoneal fluid, pleural fluid, transudates, exudates, cystic fluid, bile, urine, gastric fluids, intestinal fluids, fecal samples, and swabs, aspirates (e.g., bone marrow, fine needle, etc.), washes (e.g., oral, nasopharyngeal, bronchial, bronchialalveolar, optic, rectal, intestinal, vaginal, epidermal, etc.), and/or other specimens.

Any tissue or body fluid specimen may be used as a sample or a source of a sample for use in the technology, including forensic specimens, archived specimens, preserved specimens, and/or specimens stored for long periods of time, e.g., fresh-frozen, methanol/acetic acid fixed, or formalin-fixed paraffin embedded (FFPE) specimens and samples. In particular embodiments, the sample comprises cultured cells, such as a primary cell culture or a cell line. In some specific embodiments, the sample comprises live primary cells.

In some embodiments, sample (e.g., the cells or tissues) are infected with a virus or other intracellular pathogen. A sample can also be isolated from a non-cellular origin, e.g. amplified/isolated nucleic acid that has been stored in a freezer.

In some embodiments of the technology, the technology is applied in vivo, ex vivo, and/or in vitro. In some embodiments, the technology is used on a sample in situ, e.g., without removing it from a subject or a patient. In some embodiments, the sample is a crude sample, a minimally treated cell lysate, or a biofluid lysate.

Kits

In some embodiments, the technology provides a kit for modifying a nucleic acid (e.g., producing a knockin in a nucleic acid). In some embodiments, a kit comprises a gene editing nuclease-BE27 fusion (e.g., a gene editing nuclease-BE27 fusion (e.g., a Cas9-BE27 fusion) and/or a modified variant thereof)). In some embodiments, a kit comprises a gene editing nuclease-BE27 fusion comprising a TALEN. ZFN, and/or meganuclease and one or more BE27 domains.

In some embodiments, a kit comprises: a) a DNA-targeting RNA or a nucleic acid comprising a nucleotide sequence encoding a DNA-targeting RNA, wherein the DNA-targeting RNA comprises: i) a first segment comprising a nucleotide sequence that is complementary to a target sequence in the target DNA; and ii) a second segment that interacts with a polypeptide to form an RNP as described herein; and, optionally, b) a buffer. In some embodiments, a kit further includes one or more additional reagents, where such additional reagents can be selected from: a buffer; a wash buffer; a control reagent; a control expression vector or RNA polynucleotide; a reagent for in vitro production of the gene editing nuclease-BE27 fusion polypeptide from DNA; and the like. In some embodiments, the fusion protein further comprises a domain providing enhanced or improved localization (e.g., transport) to the nucleus (e.g., an NLS, an IBB, etc.) In some embodiments, components of the kit are in separate container; in some embodiments, one or more components of a kit are combined in a single container. Further, in some embodiments, a kit can further include instructions for using the components of the kit to practice a method described herein. In some embodiments, kits comprise one or more compositions as described herein, e.g., packaged in one or more containers for use by a user. Further, in some embodiments, a kit can further include instructions for using the components of the kit to practice a method described herein.

The present disclosure provides kits for carrying out a subject method. In some embodiments, a kit comprises a gene editing nuclease-BE27 fusion protein and/or a nucleic acid having nucleotides encoding a gene editing nuclease-BE27 fusion protein. In some embodiments, a kit further comprises a linear DNA molecule (e.g., a donor molecule). In some embodiments, a kit can further include one or more additional reagents, where such additional reagents can be selected from: a dilution buffer; a reconstitution solution; a wash buffer; a control reagent; a control expression vector or RNA polynucleotide; a reagent for in vitro production of a gene editing nuclease-BE27 fusion protein from DNA, and the like. The components of a subject kit can be in the same or different containers (in any desired combination).

In addition to above-mentioned components, a kit can further include instructions for using the components of the kit to practice a method as described herein. The instructions for practicing the subject methods are generally recorded on a suitable recording medium. For example, the instructions may be printed on a substrate, such as paper or plastic, etc. As such, the instructions may be present in the kits as a package insert, in the labeling of the container of the kit or components thereof (e.g., associated with the packaging or subpackaging) etc. In other embodiments, the instructions are present as an electronic storage data file present on a suitable computer readable storage medium, e.g. CD-ROM, diskette, flash drive, etc. In yet other embodiments, the actual instructions are not present in the kit, but means for obtaining the instructions from a remote source, e.g. via the internet, are provided. An example of this embodiment is a kit that includes a web address where the instructions can be viewed and/or from which the instructions can be downloaded. As with the instructions, this means for obtaining the instructions is recorded on a suitable substrate.

Systems

Some embodiments of the technology provide systems for modifying a nucleic acid (e.g., producing a knockin). Systems according to the technology comprise. e.g., polypeptides (e.g., a gene editing nuclease-BE27 fusion (e.g., a gene editing nuclease-BE27 fusion (e.g., a Cas9-BE27 fusion) and/or a modified variant thereof))). In some embodiments, systems comprise RNAs (e.g., dgRNA, sgRNA). Related embodiments provide expression systems (e.g., comprising nucleic acids encoding the polypeptides and/or RNAs; and one or more expression hosts) for producing polypeptides and/or RNAs described herein using an in vitro system. In some embodiments, the systems further comprise an in-vitro system for assembly of RNP complexes. Some embodiments comprise fluid handling (e.g., in some embodiments, microfluidics) components for transporting samples, reagents, and other compositions for modifying a nucleic acid with a RNP.

Some embodiments comprise components for fluid storage and fluid waste storage. In some embodiments, one or more components is/are provided to the system in the form of a kit.

In some embodiments, systems comprise a cell (e.g., a cultured cell, a primary cell, e.g., a cell in a sample obtained from a subject). For example, in some embodiments systems comprise a cell comprising a gene editing nuclease-BE27 fusion as described herein. In particular embodiments, systems comprise a cell, a polypeptide, and one or more RNA molecules. Some embodiments comprise a computer and software encoding instructions for the computer to perform. For instance, some embodiments comprise a computer system upon which embodiments of the present technology may be implemented. In various embodiments, a computer system includes a bus or other communication mechanism for communicating information and a processor coupled with the bus for processing information. In various embodiments, the computer system includes a memory, which can be a random access memory (RAM) or other dynamic storage device, coupled to the bus, and instructions to be executed by the processor. Memory also can be used for storing temporary variables or other intermediate information during execution of instructions to be executed by the processor. In various embodiments, the computer system can further include a read only memory (ROM) or other static storage device coupled to the bus for storing static information and instructions for the processor. A storage device, such as a magnetic disk or optical disk, can be provided and coupled to the bus for storing information and instructions.

In various embodiments, the computer system is coupled via the bus to a display, such as a cathode ray tube (CRT) or a liquid crystal display (LCD), for displaying information to a computer user. An input device, including alphanumeric and other keys, can be coupled to the bus for communicating information and command selections to the processor. Another type of user input device is a cursor control, such as a mouse, a trackball, or cursor direction keys for communicating direction information and command selections to the processor and for controlling cursor movement on the display. This input device typically has two degrees of freedom in two axes, a first axis (e.g., x) and a second axis (e.g., y), that allows the device to specify positions in a plane.

A computer system can perform embodiments of the present technology. Consistent with certain implementations of the present technology, results can be provided by the computer system in response to the processor executing one or more sequences of one or more instructions contained in the memory. Such instructions can be read into the memory from another computer-readable medium, such as a storage device. Execution of the sequences of instructions contained in the memory can cause the processor to perform the methods described herein. Alternatively, hard-wired circuitry can be used in place of or in combination with software instructions to implement the present teachings. Thus, implementations of the present technology are not limited to any specific combination of hardware circuitry and software.

For example, some embodiments of the technology are associated with (e.g., implemented in) computer software and/or computer hardware. In one aspect, the technology relates to a computer comprising a form of memory, an element for performing arithmetic and logical operations, and a processing element (e.g., a microprocessor) for executing a series of instructions (e.g., a method as provided herein) to read, manipulate, and store data.

Some embodiments comprise a storage medium and memory components. Memory components (e.g., volatile and/or nonvolatile memory) find use in storing instructions (e.g., an embodiment of a process as provided herein) and/or data. Some embodiments relate to systems also comprising one or more of a CPU, a graphics card, and a user interface (e.g., comprising an output device such as display and an input device such as a keyboard).

Programmable machines associated with the technology comprise conventional extant technologies and technologies in development or yet to be developed (e.g., a quantum computer, a chemical computer, a DNA computer, an optical computer, a spintronics based computer, etc.).

In some embodiments, the technology comprises a wired (e.g., metallic cable, fiber optic) or wireless transmission medium for transmitting data. For example, some embodiments relate to data transmission over a network (e.g., a local area network (LAN), a wide area network (WAN), an ad-hoc network, the internet, etc.). In some embodiments, programmable machines are present on such a network as peers and in some embodiments the programmable machines have a client/server relationship. For example, some embodiments provide systems in which a processor is remote from one or more other components of the system, e.g., to provide a system arranged in a cloud computing arrangement.

In some embodiments, data are stored on a computer-readable storage medium such as a hard disk, flash memory, optical media, a floppy disk, etc.

In some embodiments, the technology provided herein is associated with a plurality of programmable devices that operate in concert to perform a method as described herein. For example, in some embodiments, a plurality of computers (e.g., connected by a network) may work in parallel to collect and process data, e.g., in an implementation of cluster computing or grid computing or some other distributed computer architecture that relies on complete computers (with onboard CPUs, storage, power supplies, network interfaces, etc.) connected to a network (private, public, or the internet) by a conventional network interface, such as Ethernet, fiber optic, or by a wireless network technology.

For example, some embodiments provide a computer that includes a computer-readable medium. The embodiment includes a random access memory (RAM) coupled to a processor. The processor executes computer-executable program instructions stored in memory. Such processors may include a microprocessor, an ASIC, a state machine, or other processor, and can be any of a number of computer processors, such as processors from Intel Corporation of Santa Clara, California and Motorola Corporation of Schaumburg, Illinois. Such processors include, or may be in communication with, media, for example computer-readable media, which stores instructions that, when executed by the processor, cause the processor to perform the steps described herein.

Embodiments of computer-readable media include, but are not limited to, an electronic, optical, magnetic, or other storage or transmission device capable of providing a processor with computer-readable instructions. Other examples of suitable media include, but are not limited to, a floppy disk, CD-ROM, DVD, magnetic disk, memory chip, ROM, RAM, an ASIC, a configured processor, all optical media, all magnetic tape or other magnetic media, or any other medium from which a computer processor can read instructions. Also, various other forms of computer-readable media may transmit or carry instructions to a computer, including a router, private or public network, or other transmission device or channel, both wired and wireless. The instructions may comprise code from any suitable computer-programming language, including, for example, C, C++, C #. Visual Basic. Java, Python, Perl, Swift, and JavaScript.

Computers are connected in some embodiments to a network. Computers may also include a number of external or internal devices such as a mouse, a CD-ROM, DVD, a keyboard, a display, or other input or output devices. Examples of computers are personal computers, digital assistants, personal digital assistants, cellular phones, mobile phones, smart phones, pagers, digital tablets, laptop computers, internet appliances, and other processor-based devices. In general, the computers related to aspects of the technology provided herein may be any type of processor-based platform that operates on any operating system, such as Microsoft Windows. Linux, UNIX. Mac OS X, etc., capable of supporting one or more programs comprising the technology provided herein. Some embodiments comprise a personal computer executing other application programs (e.g., applications). The applications can be contained in memory and can include, for example, a word processing application, a spreadsheet application, an email application, an instant messenger application, a presentation application, an Internet browser application, a calendar/organizer application, and any other application capable of being executed by a client device.

All such components, computers, and systems described herein as associated with the technology may be logical or virtual.

In accordance with such a computer system, some embodiments of the technology provided herein further comprise functionalities for collecting, storing, and/or analyzing data. For example, some embodiments contemplate a system that comprises a processor, a memory, and/or a database for, e.g., storing and executing instructions, analyzing data, performing calculations using the data, transforming the data, and storing the data. In some embodiments, an algorithm applies a statistical model to the data.

Many diagnostics involve determining the presence of, absence of, identity of, or a nucleotide sequence of, one or more nucleic acids. Thus, in some embodiments, an equation comprising variables representing the presence, absence, identity, concentration, amount, or sequence properties of multiple nucleic acids produces a value that finds use in making a diagnosis or assessing the presence or qualities of a nucleic acid. As such, in some embodiments this value is presented by a device, e.g., by an indicator related to the result (e.g., an LED, an icon on a display, a sound, or the like). In some embodiments, a device stores the value, transmits the value, or uses the value for additional calculations.

Thus, in some embodiments, the present technology provides the further benefit that a clinician, who is not likely to be trained in genetics or molecular biology, need not understand the raw data. The data are presented directly to the clinician in its most useful form. The clinician is then able to utilize the information to optimize the care of a subject. The present invention contemplates any method capable of receiving, processing, and transmitting the information to and from laboratories conducting the assays, information providers, medical personal, and/or subjects. For example, in some embodiments of the present technology, a sample is obtained from a subject and submitted to a profiling service (e.g., a clinical lab at a medical facility, genomic profiling business, etc.), located in any part of the world (e.g., in a country different than the country where the subject resides or where the information is ultimately used) to generate raw data. Where the sample comprises a tissue or other biological sample, the subject may visit a medical center to have the sample obtained and sent to the profiling center or subjects may collect the sample themselves and directly send it to a profiling center. Where the sample comprises previously determined biological information, the information may be directly sent to the profiling service by the subject (e.g., an information card containing the information may be scanned by a computer and the data transmitted to a computer of the profiling center using electronic communication systems). Once received by the profiling service, the sample is processed and a profile is produced that is specific for the diagnostic or prognostic information desired for the subject. The profile data are then prepared in a format suitable for interpretation by a treating clinician. For example, rather than providing raw expression data, the prepared format may represent a diagnosis or risk assessment for the subject, along with recommendations for particular treatment options. The data may be displayed to the clinician by any suitable method. For example, in some embodiments, the profiling service generates a report that can be printed for the clinician (e.g., at the point of care) or displayed to the clinician on a computer monitor. In some embodiments, the information is first analyzed at the point of care or at a regional facility. The raw data are then sent to a central processing facility for further analysis and/or to convert, the raw data to information useful for a clinician or patient. The central processing facility provides the advantage of privacy (all data are stored in a central facility with uniform security protocols), speed, and uniformity of data analysis. The central processing facility can then control the fate of the data following treatment of the subject. For example, using an electronic communication system, the central facility can provide data to the clinician, the subject, or researchers. In some embodiments, the subject is able to access the data using the electronic communication system. The subject may chose further intervention or counseling based on the results. In some embodiments, the data are used for research use. For example, the data may be used to further optimize the inclusion or elimination of markers as useful indicators of a particular condition associated with the disease.

Uses

The imaging technologies described herein find use in. e.g., imaging, diagnostics, and treatment of patients. Applications include research applications; diagnostic applications; industrial applications; and treatment applications. Research applications include, e.g., characterizing, detecting, and/or identifying nucleic acids in a cell (e.g., a living cell). Further uses of embodiments of the technology described herein include one or more of the following: genome imaging; copy number analysis; analysis of living cells; detection of highly repetitive genome sequence or structure; detection of complex genome sequences or structures; detection of gene duplication or rearrangement; chromosomal labeling; large scale diagnostics of diseases and genetic disorders related to genome deletion, duplication, and rearrangement; use of multiple unique sgRNAs for high-throughput imaging and/or diagnostics; multicolor differential detection of target sequences; identification or diagnosis of diseases of unknown cause or origin; and 4-dimensional (e.g., time-lapse) or 5-dimensional (e.g., multicolor time-lapse) imaging of cells (e.g., live cells), tissues, or organisms.

In some embodiments, compositions, kits, and methods find use for the integration of a donor DNA molecule into any desirable nucleic acid. e.g., a supercoiled target DNA molecule, a chromosome, an extrachromosomal element, etc. The following uses are merely illustrative examples and are by no means meant to limit the use of the subject methods. In some embodiments, the compositions, kits, and methods find use for in vitro use outside of a cell (e.g., to modify a plasmid DNA, to modify an isolated chromosomal DNA, etc.). In some embodiments, the compositions, kits, and methods find use inside of a eukaryotic cell (e.g., in vitro and/or in in vivo and/or ex vivo). In some embodiments, the compositions, kits, and methods are used to insert and/or modify a control element (e.g., a transcriptional control element such as an enhancer, a promoter, a transcription terminator, etc.). In some embodiments, the compositions, kits, and methods find use to modify a target gene (e.g., in some cases disrupting the expression of the target gene, in some cases, modifying the transcribed RNA, etc.). In some embodiments, the compositions, kits, and methods find use to modify a coding and/or a non-coding sequence (e.g., modify a gene coding sequence, modify a sequence that codes for a non-coding RNA such as a microRNA).

Uses of a Gene Editing Nuclease-BE27 Fusion to Modify a Cell or Organism

The technology in some embodiments comprises a method of modifying an cell or organism. The cell may be a prokaryotic cell or a eukaryotic cell. The cell may be a mammalian cell. The mammalian cell many be a non-human primate, bovine, porcine, rodent or mouse cell. The cell may be a non-mammalian eukaryotic cell such as poultry, fish or shrimp. The cell may also be a plant cell. The plant cell may be of a crop plant such as cassava, corn, sorghum, wheat, or rice. The plant cell may also be of an algae, tree or vegetable. The modification introduced to the cell by the present technology may be such that the cell and progeny of the cell are altered for improved production of biologic products such as an antibody, starch, alcohol or other desired cellular output. The modification introduced to the cell by the present technology may be such that the cell and progeny of the cell include an alteration that changes the biologic product produced.

The technology may comprise use of one or more different vectors. In some embodiments of the technology, the gene editing nuclease-BE27 fusion protein is codon optimized for expression the desired cell type, preferentially a eukaryotic cell, preferably a mammalian cell or a human cell.

In some embodiments, packaging cells are used to form virus particles that are capable of infecting a host cell. Such cells include 293 cells, which package adenovirus, and psi2 cells or PA317 cells, which package retrovirus. Viral vectors used in gene therapy are usually generated by producing a cell line that packages a nucleic acid vector into a viral particle. The vectors typically contain the minimal viral sequences required for packaging and subsequent integration into a host, other viral sequences being replaced by an expression cassette for the polynucleotide(s) to be expressed. The missing viral functions are typically supplied in trans by the packaging cell line. For example, AAV vectors used in gene therapy typically only possess ITR sequences from the AAV genome which are required for packaging and integration into the host genome. Viral DNA is packaged in a cell line, which contains a helper plasmid encoding the other AAV genes, namely rep and cap, but lacking ITR sequences. The cell line may also be infected with adenovirus as a helper. The helper virus promotes replication of the AAV vector and expression of AAV genes from the helper plasmid. The helper plasmid is not packaged in significant amounts due to a lack of ITR sequences. Contamination with adenovirus can be reduced by, e.g., heat treatment to which adenovirus is more sensitive than AAV.

In some embodiments, one or more vectors described herein are used to produce a non-human transgenic animal or transgenic plant. In some embodiments, the transgenic animal is a mammal, such as a mouse, rat, or rabbit. Methods for producing transgenic animals and plants are known in the art, and generally begin with a method of cell transfection, such as described herein. In another embodiment, a fluid delivery device with an array of needles (see. e.g., US Patent Publication No. 20110230839 assigned to the Fred Hutchinson Cancer Research Center) may be contemplated for delivery of a gene editing nuclease-BE27 fusion to solid tissue. A device of US Patent Publication No. 20110230839 for delivery of a fluid to a solid tissue may comprise a plurality of needles arranged in an array; a plurality of reservoirs, each in fluid communication with a respective one of the plurality of needles; and a plurality of actuators operatively coupled to respective ones of the plurality of reservoirs and configured to control a fluid pressure within the reservoir.

In some embodiments, the technology provides for methods of modifying a target polynucleotide in a eukaryotic cell. In some embodiments, the method comprises allowing a nucleic acid-targeting complex to bind to the target polynucleotide to effect cleavage of said target polynucleotide thereby modifying the target polynucleotide, wherein the nucleic acid-targeting complex comprises a nucleic acid-targeting effector protein complexed with a guide RNA hybridized to a target sequence within said target polynucleotide.

In some embodiments, the technology provides a method of modifying expression of a polynucleotide in a eukaryotic cell. In some embodiments, the method comprises allowing a nucleic acid-targeting complex to bind to the polynucleotide such that said binding results in increased or decreased expression of said polynucleotide; wherein the nucleic acid-targeting complex comprises a nucleic acid-targeting effector protein complexed with a guide RNA hybridized to a target sequence within said polynucleotide.

In some embodiments, the technology provides a method of inserting a polynucleotide into the genome of a eukaryotic cell. In some embodiments, the method comprises allowing a nucleic acid-targeting complex to bind to the polynucleotide such that said binding results in the insertion of said polynucleotide at a target locus; wherein the nucleic acid-targeting complex comprises a nucleic acid-targeting effector protein complexed with a guide RNA hybridized to a target sequence within said polynucleotide.

Although the disclosure herein refers to certain illustrated embodiments, it is to be understood that these embodiments are presented by way of example and not by way of limitation.

EXAMPLES

Provided herein is a modified CRISPR/Cas9 technology for improved gene editing. During the development of embodiments of the technology provided herein, experiments indicated that the improved CRISPR technology increased by several fold the KI efficiency of reporter genes at multiple loci in human primary cells, pluripotent stem cells, and adult stem cells. Furthermore, the improved CRISPR technology provided herein minimized and/or eliminated off-target insertion and deletion ("indel") events at several genetic loci (e.g., VEGFA, EMX1, and FNACF) known to be especially prone to off-target CRISPR modification. The CRISPR technology provided herein finds use in a range of gene editing research and therapeutics applications.

Conventional CRISPR/Cas9 technologies create double stranded breaks (DSBs) at a target locus in a genome. Two major mechanisms, non-homologous end joining (NHEJ) and homology directed repair (HDR), function to repair DSBs. The majority of DSBs are repaired by NHEJ mechanisms (see, e.g., Zhu et al. (2014) "The iCRISPR platform for rapid genome editing in human pluripotent stem cells" Methods in enzymology 546: 215-250; Wang et al. (2013) "One-step generation of mice carrying mutations in multiple genes by CRISPR/Cas-mediated genome engineering" Cell 153(4): 910-918) NHEJ directly ligates break ends without using a homologous template, which produces insertions and deletions (indels) in a genome with low predictability or insufficient predictability to provide a robust and useful gene editing tool. In contrast, HDR occurs when homologous donor templates are present, thus producing correct repair or knock-in events. Accordingly, when DSBs are repaired by the HDR pathway in the presence of a donor template comprising a nucleic acid insert, knock-in of the insert takes place with increased specificity for the target locus (FIG. 1). In particular, the use of a pre-assembled ribonucleoprotein (RNP), comprising a CRISPR/Cas9 protein and a guide RNA (gRNA), and a short single-stranded oligodeoxynucleotide (ssODN) donor template induces the single-strand annealing (SSA) pathway for nucleic acid repair, which has been shown to improve the precision of producing mutations to efficiencies in the double digits. Despite these advances, use of CRISPR technologies to knock in a large-fragment donor template by homologous recombination (IR) pathways has achieved efficiencies of no greater than approximately 1%.

Materials and Methods

Cell culture: cells were maintained as follows. ATCC CRL2522 cells were cultured with RPMI 1640 Medium supplemented with 15% fetal bovine serum (Nucleus Biologics, 20161019-1) and 10 Units/ml human recombinant insulin. Airway stem cells were maintained as described previously (Levardon (2018) Expansion of Airway Basal Cells and Generation of Polarized Epithelium. Bio Protoc 8(11), incorporated herein by reference). Briefly, cells were cultured with epithelial basal cell culture medium (Lonza. CC-3118 or Promocell. C-21170) supplemented with 0.5-1 µM A-83-01, 0.2-0.5 µM DMH1-1, 0.5-1 µM CHIR99021, and 5-10 µM Y27632. Human embryonic kidney 293T cells were cultured in Dulbecco's Modified Eagle Medium (DMEM) (Gibco, 11995-065) supplemented with 10% fetal bovine serum. Human iPSC cells were cultured on Matrigel Matrix (Corning, 354277) with MTESR1 medium (STEMCELL Technologies, 85850). To maintain the maximum health of the cells, the culture mediums were changed every day for airway stem cells and human iPSC cells. Trypsin was used for CRL2522 cells and airway stem cells for passage, and the passaging reagent (STEMCELL Technologies, 05872) was used for human iPSC cells.

Construction of plasmids: GFP knock-in experiments were used to target the genomic loci (e.g., Rosa26 and AAVS1) with a CRISPR/Cas9 system, sgRNA constructs were produced by inserting targeted sequence into phU6-sgRNA (addgene #53188) (see, e.g., Kabadi (2014) Multiplex CRISPR/Cas9-based genome engineering from a single lentiviral vector. Nucleic Acids Res 42(19): e147, incorporated herein by reference). GFP coding sequences were amplified to construct a double stranded GFP targeting repair donor. Then, both homologous arms corresponding to Rosa26 and AAVS1 sites were amplified from human genomic DNA and inserted on both sides of the GFP coding sequence. The homologous arms used are ~500 bp. DNA oligonucleotides were synthesized by IDT. Sequences are provided in FIG. 9.

Cell electroporation: cultured cells were electroporated with a Celetrix (Celetrix, CTX-1500A LE) electroporator according to the manufacturer instructions manual or as previously reported (see. e.g., Xu (2018) Efficient homology-directed gene editing by CRISPR/Cas9 in human stem and primary cells using tube electroporation. Sci Rep 8(1): 11649, incorporated herein by reference). The same plasmid:cell ratio was used to electroporate different types of cells for knock-in experiments. A number of 2-3×10$^6$ cells were collected in 120 μl of electroporation buffer (Celetrix, 13-0104), 4 μg of EcoRI linearized GFP repair donor plasmid was added, 4.5 μg Cas9 expressing plasmid was added, and 1.5 μg sgRNA expressing plasmid was added. After mixing, the mixture of plasmids and cells was transferred to a 120-μl electroporation tube with a long fin tip and electroporated in Celetrix electroporator with 620 V voltage. For human iPS cell electroporation, iPS cells were treated with Y27632 (10 μM for 1 hour) and then treated with accutase (STEMCELL Technologies, 0792) to provide a single cell suspension. After electroporation, iPSC cells were cultured in Y27632-containing MTESR1 medium and replaced with normal MTESR1 medium 24 hours later. For CRL2522 cells and airway stem cells, trypsin was used to produce a single cell suspension. Gene editing efficiency was measured with flow cytometry by calculating GFP positive cells two-three days after electroporation.

Fluorescence-associated cell sorting: cultured cells were dissociated to produce a single cell suspension in 300 μl PBS with 2% fetal bovine serum and filtered with a 70-μm nylon strainer. The percentage of GFP positive cells was used as the indicator of knock-in events.

Cas9-induced on-target and off-target mutation detection: to evaluate Cas9 induced on-target and off-target gene editing efficiency, genomic DNA was collected from cells transfected with a conventional Cas9 expressing vector or a Cas9-BE27 fusion protein expressing vector and a corresponding sgRNA expressing vector two days after transfection. PCR was used to amplify DNA fragments containing sgRNA off-target sites as indicated by bioinformatics analysis. The T7E1 assay and deep sequencing were used to determine gene editing efficiency. For the T7E1 assay. PCR fragments were annealed and then cut by T7 endonuclease I. For deep sequencing, amplified DNA fragments were sent to the MGH DNA sequencing core for sequencing. Potential off-target sites were found by using Cas-OFFinder.

Serum starvation: serum starvation was used to synchronize 293 cells into G0 phase. Serum was withdrawn from culture medium completely and after 24 hours of serum starvation, a conventional Cas9 expressing vector or a Cas9-BE27 fusion protein expressing vector and sgRNA expressing plasmid mixture were transfected to synchronized 293 cells with lipofectamine 2000 (Invitrogen, 11668019). Two days after transfection, cells were analyzed for Cas9 cutting efficiency by T7E1 assay.

Example 1—CRISPR System Design

Figure 2:
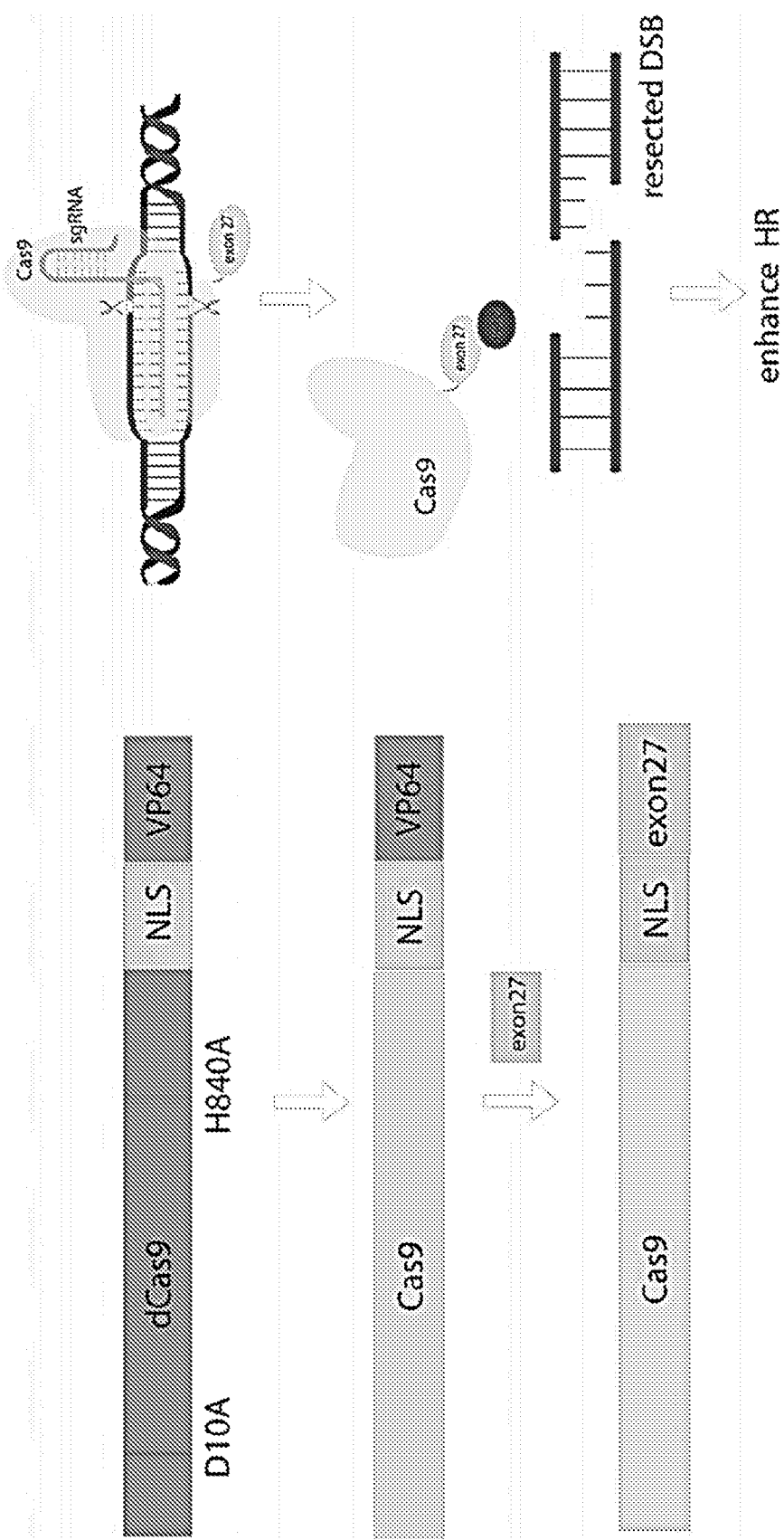
FIG. 2 is a schematic drawing showing the development of an embodiment of the Cas9-BE27 fusion protein technology provided herein.

The HR process involves BRCA2 delivering RAD51 to a resected DNA overhang at a DSB to form a RAD51/DNA filament. In particular, data have indicated that a RAD51 binding sequence encoded by BRCA2 exon 27 (hereinafter referred to by the term "BE27") deposits RAD51 at the DSB. Accordingly, experiments were conducted during the development of embodiments of the technology described herein to construct a fusion of BE27 and Cas9. Data were collected during these experiments indicated that the Cas9-BE27 fusion provided an efficient deposition of RAD51 at the DSB, thus increasing the amount and/or concentration of RAD51 the DSB and, consequently, improving the HDR-mediated knock in of large fragment inserts at the target locus During the development of embodiments of the improved CRISPR technology, experiments were conducted to produce an improved CRISPR protein (FIG. 2). First, a nucleic acid encoding a nuclease "dead" Cas9 fused to VPG4 was acquired ("dCas9-VP64 protein"), e.g., the PMLM3705 plasmid (Addgene plasmid #47754); see, e.g., Maeder et al (2013) "CRISPR RNA-guided activation of endogenous human genes" Nature Methods 10: 977). Next, the dCas9-VP64 protein was reverse engineered to generate a nuclease-active Cas9-VP64. In particular, the nucleic acid sequence encoding the dCas9-VP64 was modified to replace the nuclease-inactivating amino acid substitutions of D10A and H840A with alanines at positions 10 and 840. Finally, the nucleic acid encoding the VP64 domain was replaced with a 108-bp nucleic acid encoding the BE27 sequence of 36 amino acids:

```
                                        SEQ ID NO: 1
        ALDFLSRLPLPPPVSPICTFVSPAAQKAFQPPRSCG
```

Embodiments of the technology thus provide a Cas9-BE27 fusion protein. In some embodiments, the Cas9-BE27 fusion protein comprises a nuclear localization signal (NLS; see. e.g., FIG. 2). In some embodiments, the technology comprises. e.g., a nucleic acid encoding a Cas9-BE27 fusion protein, a vector comprising a nucleic acid encoding a Cas9-BE27 fusion protein, a cell comprising and/or expressing a nucleic acid encoding a Cas9-BE27 fusion protein, and/or a cell comprising and/or expressing a Cas9-BE27 fusion protein. In some embodiments, the technology comprises, e.g., a nucleic acid encoding a Cas9-BE27 fusion protein comprising an NLS, a vector comprising a nucleic acid encoding a Cas9-BE27 fusion protein comprising an NLS, a cell comprising and/or expressing a nucleic acid encoding a Cas9-BE27 fusion protein comprising an NLS, and/or a cell comprising and/or expressing a Cas9-BE27 fusion protein comprising an NIS. As used herein, the term "Cas9-BE27 fusion protein" refers both to a Cas9-BE27 fusion protein and a Cas9-BE27 fusion protein comprising an NLS. Further, as used herein, the term "mi-Cas9" is used to refer to embodiments of the Cas9-BE27 fusion protein and a Cas9-BE27 fusion protein comprising an NLS described herein and the term "mi-CRISPR" is used to refer to CRISPR technologies using the Cas9-BE27 fusion protein and a Cas9-BE27 fusion protein comprising an NLS described herein.

Example 2—Mi-CRISPR Improves Knockin Efficiency

Figure 3:
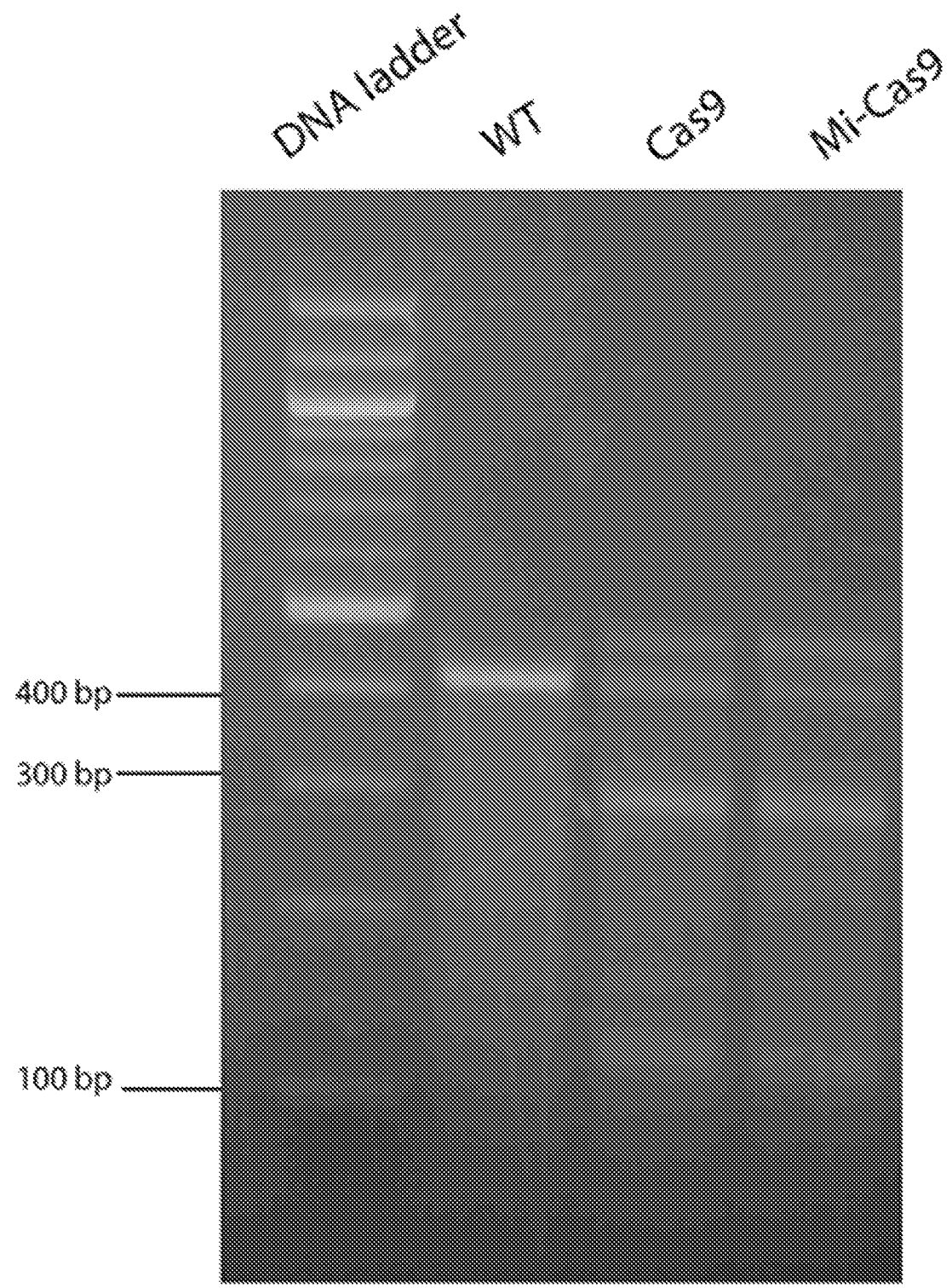
FIG. 3 is an image of an agarose gel showing the results of an experiment conducted during the development of embodiments of the technology to assess the targeting efficiency of an embodiment of a gene editing nuclease-BE27 fusion protein as described herein.

Experiments were conducted during the development of the technology provided herein to test the targeting efficiency of CRISPR using the Cas9-BE27 fusion protein. An AAVS1-specific gRNA and either the Cas9-BE27 fusion protein ("mi-Cas9") or conventional Cas9 ("c-Cas9") were co-transfected into human cells (e.g., HEK 293 cells). A T7 endonuclease I assay (T7E1 assay; see, e.g., Guschin et al. (2010) "A rapid and general assay for monitoring endogenous gene modification" Methods Mol Biol 649: 247-256, incorporated herein by reference) was used to detect the targeting efficiency of mi-CRISPR and conventional CRISPR at the AAVS1 locus. Briefly, genomic DNA was isolated from the cells, PCR products were produced from the genomic DNA, and the PCR products were annealed and digested with T7 endonuclease 1. The fragments were analyzed by gel electrophoresis to determine the efficiency of genome targeting (FIG. 3). The amplicon containing the targeted site is approximately 400 bp (FIG. 3, WT lane). Successful CRISPR targeting produces DSB and is detected on the gel as two small bands (FIG. 3, Cas9 lane and mi-Cas9 lane). Data collected during these experiments using indicated that mi-CRISPR targeting the AAVS1 locus in human cells generated indel rates comparable to the rate of indel production by conventional Cas9. Deepseq analysis indicated that the mi-CRISPR indel rate was 52.9% and the indel rate by conventional Cas9 CRISPR was 65.3%. Without being bound by theory, it was contemplated that the lower overall indel rate for mi-CRISPR reflects the increased rate of faithful HDR repair is mi-CRISPR relative to conventional CRISPR using a conventional Cas9.

During experiments conducted during the development of embodiments of the technology described herein, the efficiencies of producing mi-CRISPR and conventional CRISPR knockins were compared. Data were collected during experiments in which mi-CRISPR and conventional CRISPR were used to insert a nucleic acid comprising a coding sequence for green fluorescent protein (GFP) at the AAVS1 locus using the conventional Cas9 protein or Cas9-BE27 fusion protein and a gRNA targeting the AAVS1 locus in human cells (e.g., fibroblasts, airway stem cells, and human induced pluripotent stem cells). See, e.g., FIGS. 4A, 4B, 4C, and 4D. As depicted schematically in FIG. 4A, the gRNA was designed to comprise the sequence:

(SEQ ID NO: 2)
GGGGCCACTAGGGACAGGATTGG.

Figure 4A:
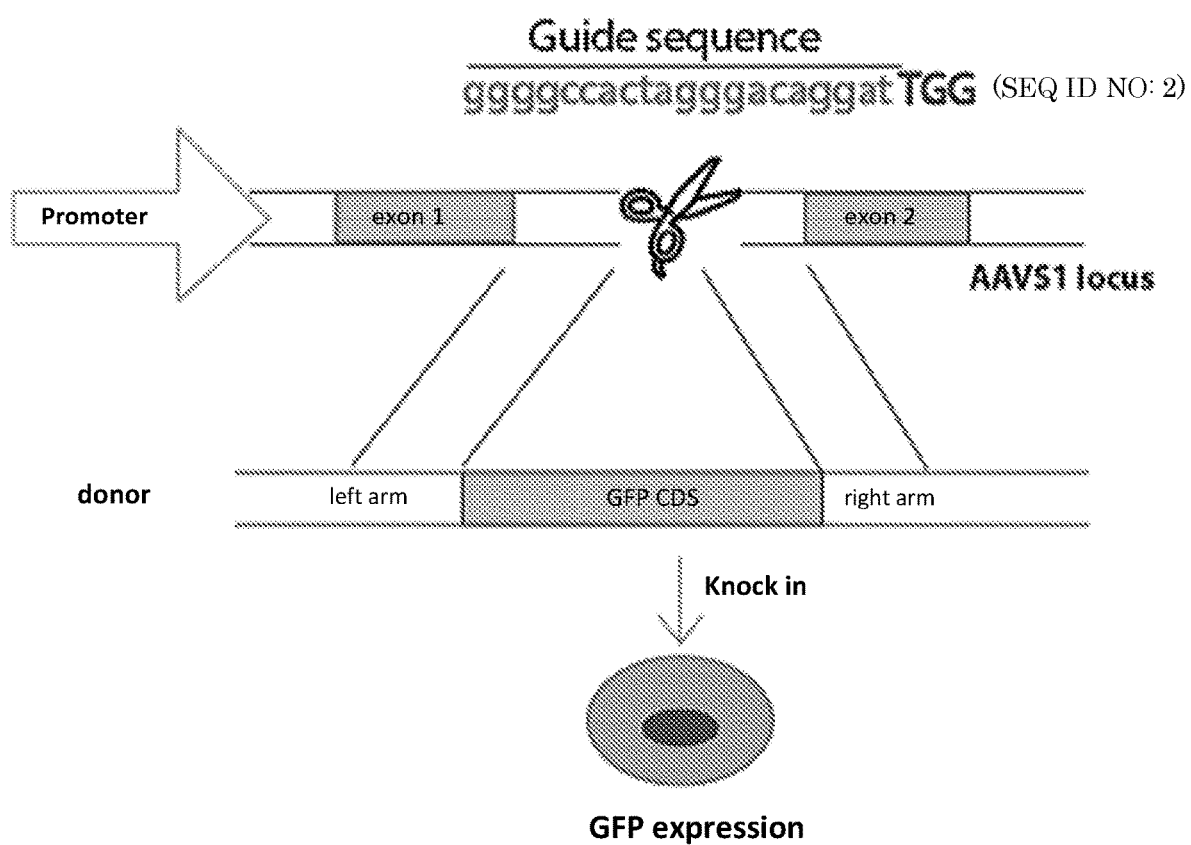
FIG. 4A is a schematic drawing showing the experimental design used to test knockin of GFP at the AAVS1 locus using an embodiment of the gene editing nuclease-BE27 fusion protein technology as described herein.
Figure 4B:
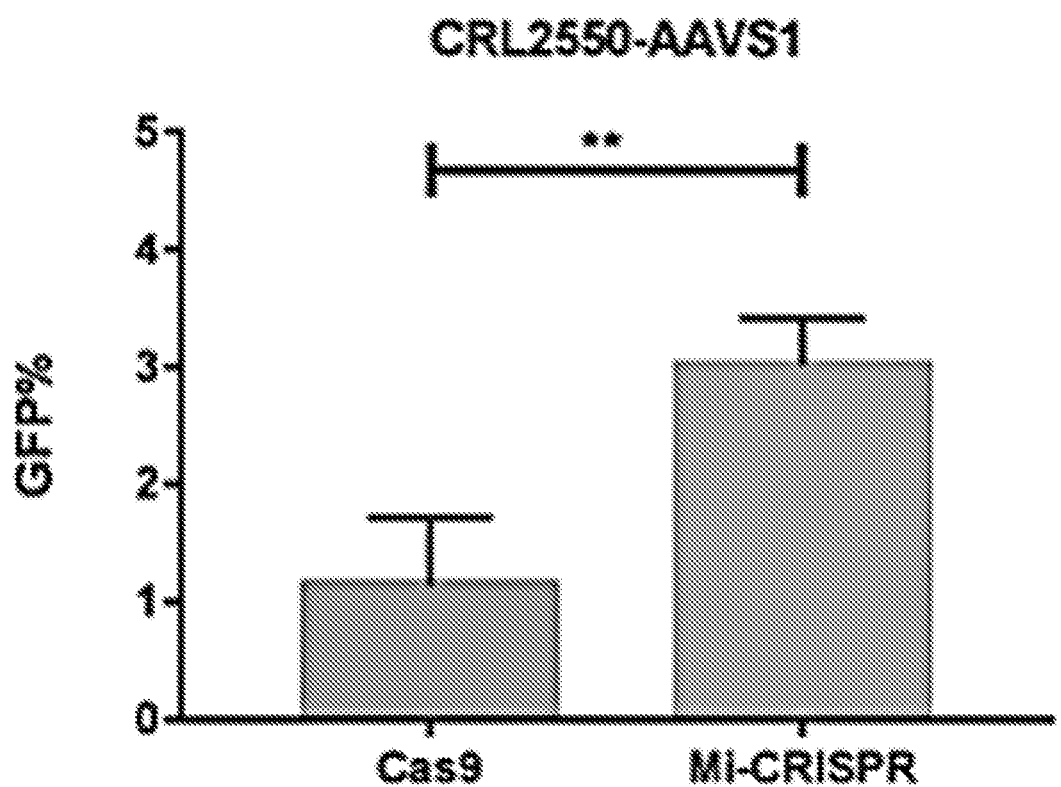
FIG. 4B is a bar plot showing the quantification of data collected during an experiment performed as depicted in FIG. 4A to knockin GFP at the AAVS1 locus in fibroblast cells.
Figure 4C:
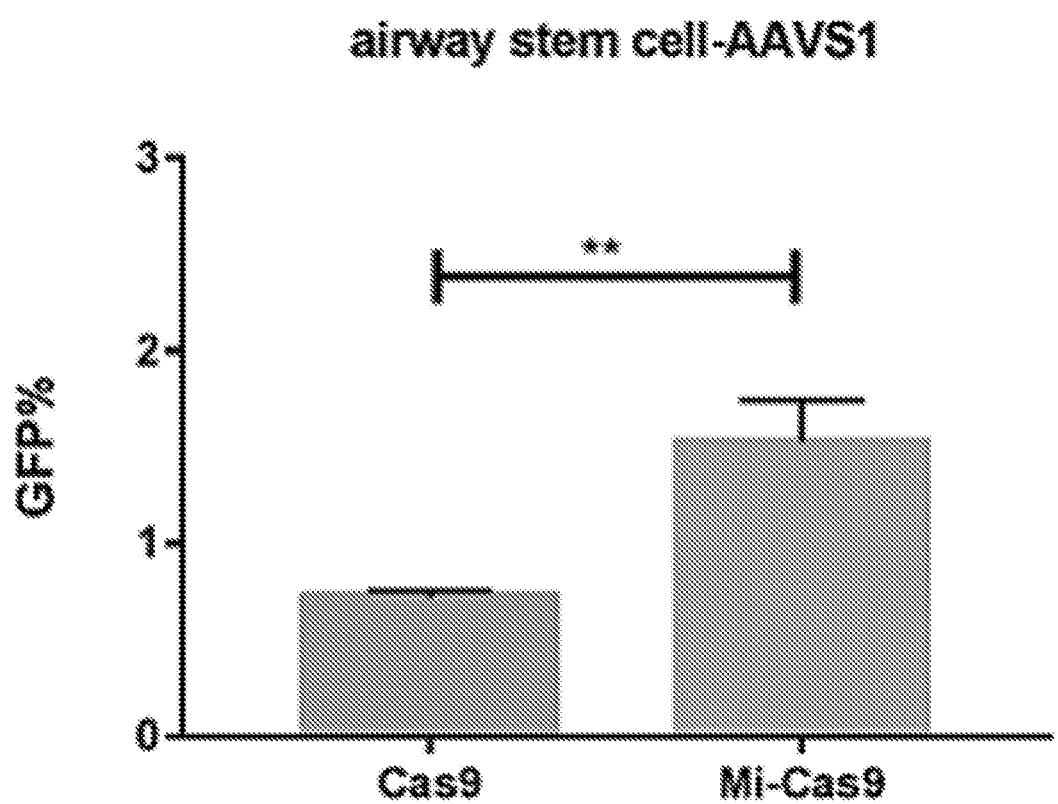
FIG. 4C is a bar plot showing the quantification of data collected during an experiment performed as depicted in FIG. 4A to knockin GFP at the AAVS1 locus in airway stem cells.
Figure 4D:
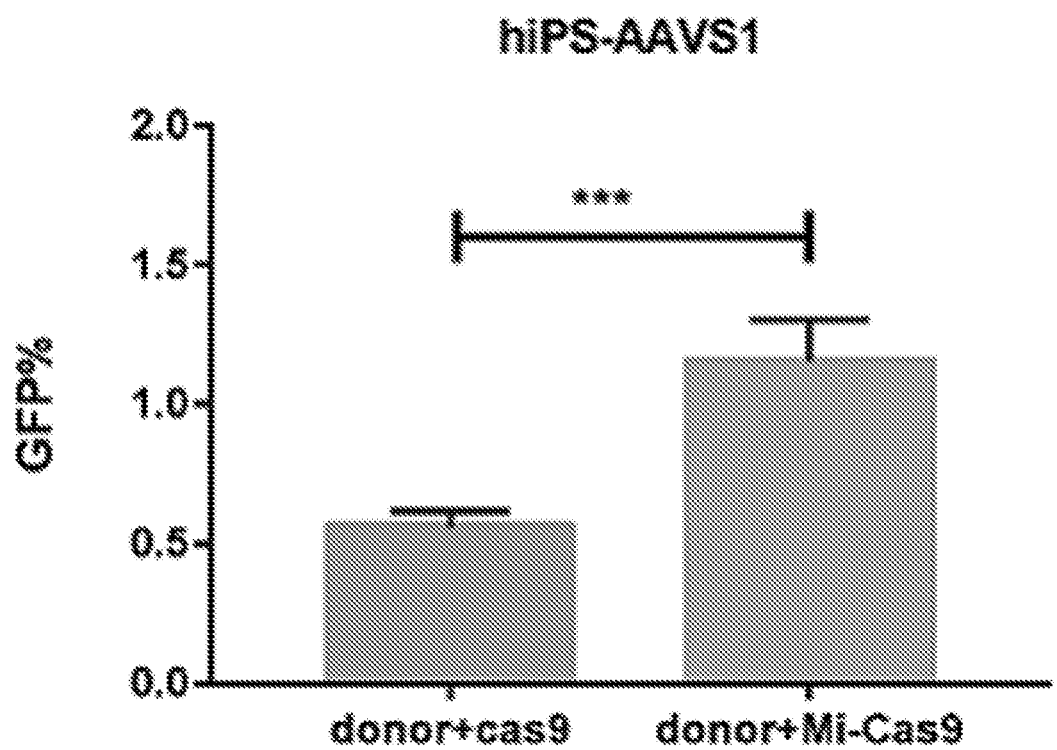
FIG. 4D is a bar plot showing the quantification of data collected during an experiment performed as depicted in FIG. 4A to knockin GFP at the AAVS1 locus in induced pluripotent stem cells.

The AAVS1-specific sequence GGGGC-CACTAGGGACAGGAT (SEQ ID NO: 3) is shown in lower case in FIG. 4A and the PAM sequence (TGG) is shown in upper case in FIG. 4A. An AAVS1 targeting vector was designed to comprise a splice acceptor (S A-GFP coding sequence flanked by homology arms of approximately 500 bp. Cells were co-transfected with linearized ROSA26 targeting vector, sgRNA, and a conventional Cas9 or a Cas9-BE27 fusion protein ("mi-Cas9") expression plasmid for conventional CRISPR or mi-CRISPR knockin. The experiment was designed to detect DSBs produced at the target region by CRISPR or mi-CRISPR, the latter of which was expected to be repaired more efficiently by HDR rather than by NHEJ. In the experiments. HDR is detected by GFP expression resulting from integration of the GFP coding sequence at the target site and expression of GFP driven by the AAVS1 promoter. HDR-mediated GFP integration efficiencies were determined by flow cytometry to identify GFP+ cells three to five days after transfection. The percentage of GFP+ cells indicated the HDR-mediated GFP knockin efficiency in the human cells. FIG. 4B shows the results for fibroblasts; FIG. 4C shows the results for airway stem cells; and FIG. 4D shows the results for human induced pluripotent stem cells. In FIGS. 4B-4D, n=3 to 5; error bars indicate standard deviation; and *P<0.05, P<0.01, *P<0.001. As indicated by FIGS. 4A-4D, the mi-CRISPR method described herein using the Cas9-BE27 fusion protein improved the knockin rate in all cells tested by approximately 2 to 3 fold. In particular, the efficiencies of mi-CRISPR and conventional CRISPR were 3.02% and 1.14%, respectively, in fibroblast cells; the efficiencies of mi-CRISPR and conventional CRISPR were 0.71% and 1.53%, respectively, in airway stem cells; and the efficiencies of mi-CRISPR and conventional CRISPR were 0.56% and 1.16%, respectively, in induced pluripotent stem cells.

Next, during the development of embodiments of the technology described herein, experiments were conducted to test the improved efficiency of mi-CRISPR knockin at another locus of the human genome to confirm that the improved efficiency observed was not locus specific. In particular, the efficiencies of producing mi-CRISPR and conventional CRISPR knockins at the ROSA26 "safe harbor" locus were compared using an experimental system similar to that described above for producing knockins at the AAVS1 locus. Data were collected during experiments in which mi-CRISPR and conventional CRISPR were used to insert a nucleic acid comprising a coding sequence for green fluorescent protein (GFP) at the ROSA26 locus using the conventional Cas9 protein or Cas9-BE27 fusion protein and a gRNA targeting the ROSA26 locus in human cells (e.g., fibroblasts, airway stem cells, and human induced pluripotent stem cells). See, e.g., FIGS. 5A, 5B, 5C, and 5D. As depicted schematically in FIG. 5A, the gRNA was designed to comprise the sequence:

(SEQ ID NO: 4)
AATTGAGCCTGCCGTGTTTCTGAGG.

Figure 5A:
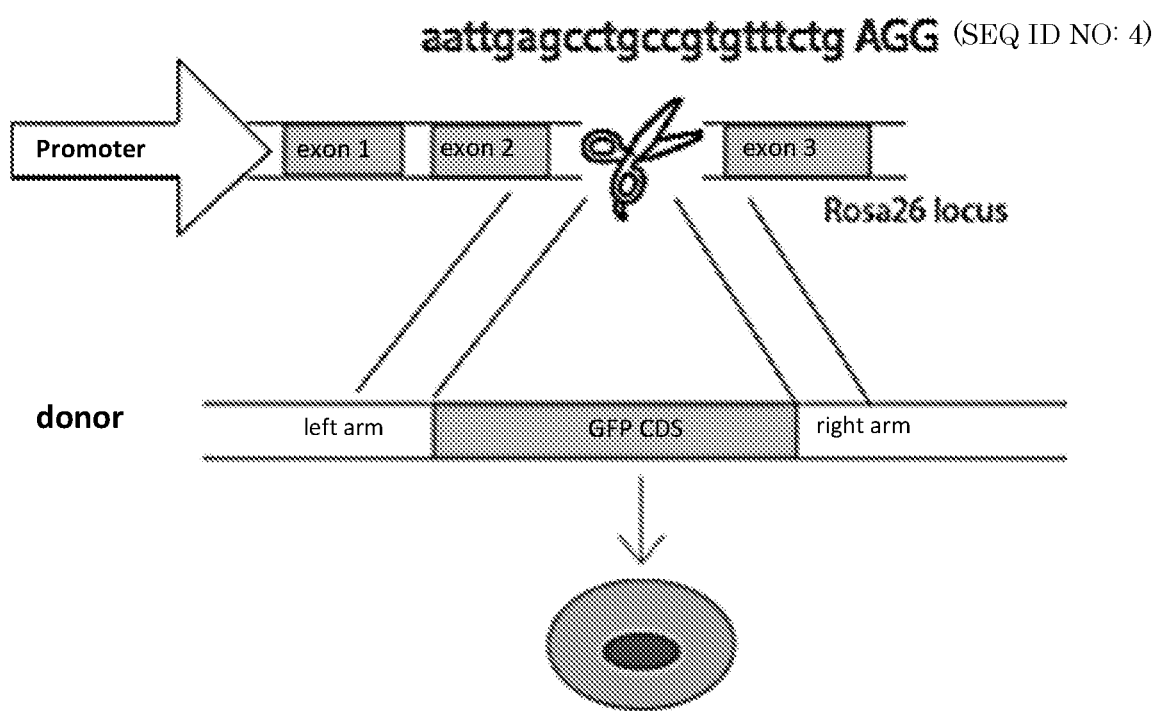
FIG. 5A is a schematic drawing showing the experimental design used to test knockin of GFP at the Rosa26 locus using an embodiment of the gene editing nuclease-BE27 fusion protein technology as described herein.
Figure 5B:
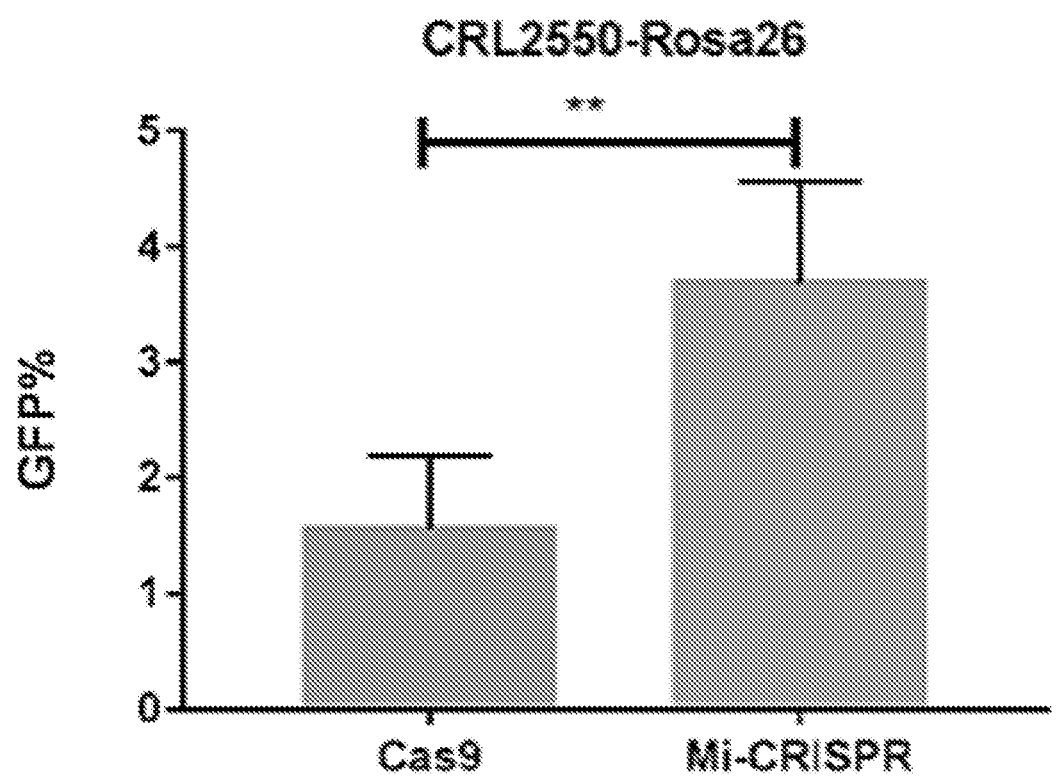
FIG. 5B is a bar plot showing the quantification of data collected during an experiment performed as depicted in FIG. 5A to knockin GFP at the Rosa26 locus in fibroblast cells.
Figure 5C:
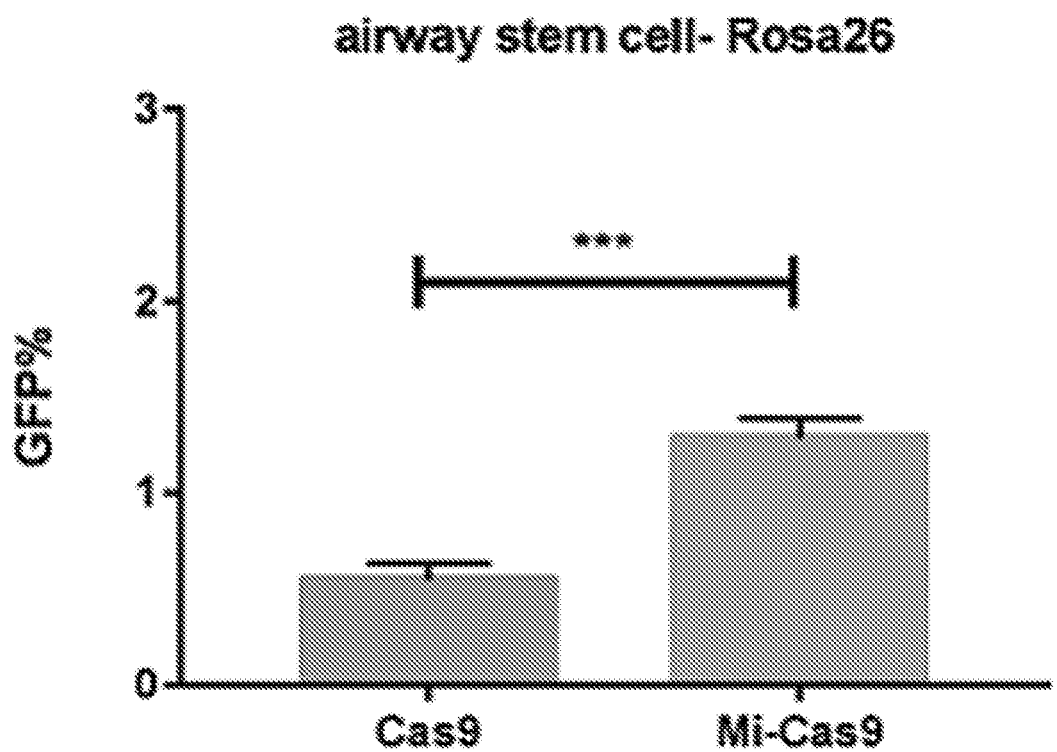
FIG. 5C is a bar plot showing the quantification of data collected during an experiment performed as depicted in FIG. 5A to knockin GFP at the Rosa26 locus in airway stem cells.
Figure 5D:
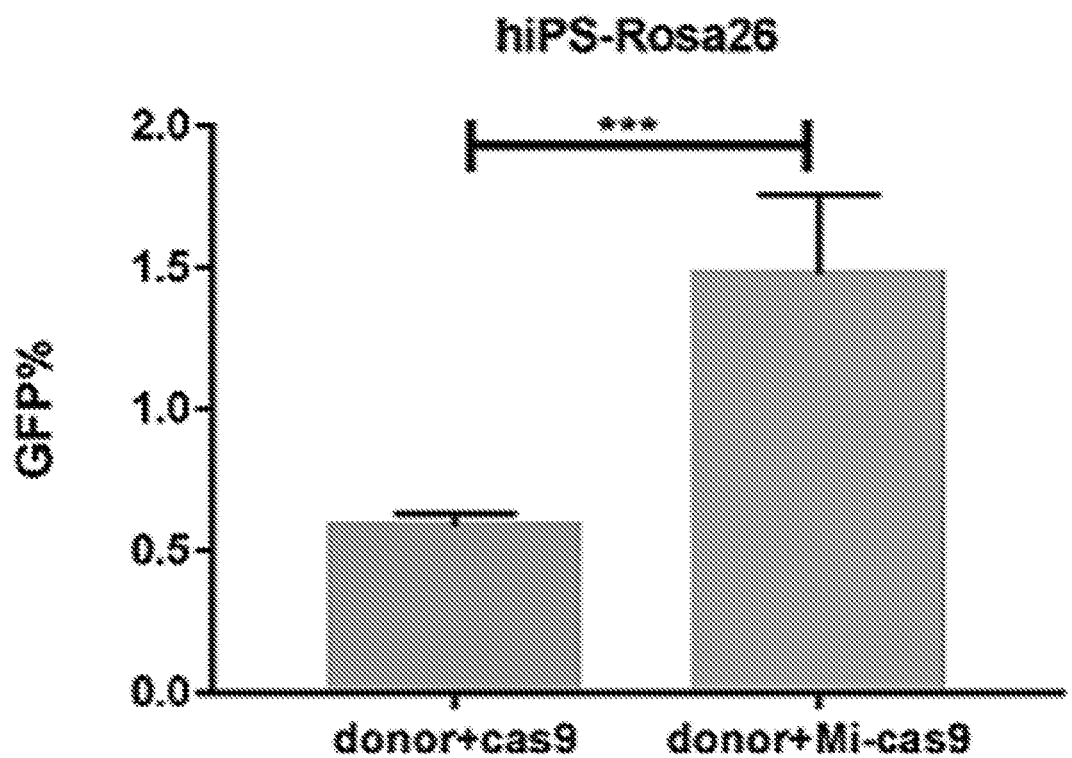
FIG. 5D is a bar plot showing the quantification of data collected during an experiment performed as depicted in FIG. 5A to knockin GFP at the Rosa26 locus in induced pluripotent stem cells.

The ROSA26-specific sequence AATT-GAGCCTGCCGTGTTTCTG (SEQ ID NO: 5) is shown in lower case in FIG. 5A and the PAM sequence (AGG) is shown in upper case in FIG. 5A. A ROSA26 targeting vector was designed to comprise a splice acceptor (SA)-GFP coding sequence flanked by homology arms of approximately 500 bp. Cells were co-transfected with linearized ROSA26 targeting vector, sgRNA, and a conventional Cas9 or a Cas9-BE27 fusion protein ("mi-Cas9") expression plasmid for conventional CRISPR or mi-CRISPR knockin. The experiment was designed to detect DSBs produced at the target region by CRISPR or mi-CRISPR, the latter of which was expected to be repaired more efficiently by HDR rather than by NHEJ. In the experiments, HDR is detected by GFP expression resulting from integration of the GFP coding sequence at the target site and expression of GFP driven by the ROSA26 promoter. HDR-mediated GFP integration efficiencies were determined by flow cytometry to identify GFP+ cells three to five days after transfection. The percentage of GFP+ cells indicated the HDR-mediated GFP knockin efficiency in the human cells. FIG. 5B shows the results for fibroblasts; FIG. 5C shows the results for airway stem cells; and FIG. 5D shows the results for human induced pluripotent stem cells. In FIGS. 5B-5D, n=3 to 5; error bars indicate standard deviation; and *P<0.05, P<0.01, *P<0.001. As indicated by FIGS. 5A-5D, the mi-CRISPR method described herein using the Cas9-BE27 fusion protein improved the knockin rate at the ROSA26 locus in all cells tested by approximately 2 to 3 fold, similarly to the increased knockin efficiency measured for knockin at the AAVS1 locus. In particular, the efficiencies of mi-CRISPR and conventional CRISPR knockin at the ROSA26 locus were 1.55% and 3.68%, respectively, in fibroblast cells; the efficiencies of mi-CRISPR and conventional CRISPR were 0.54% and 1.28%, respectively, in airway stem cells; and the efficiencies of mi-CRISPR and conventional CRISPR were 0.59% and 1.48%, respectively, in induced pluripotent stem cells. Knockin efficiencies for mi-CRISPR relative to conventional CRISPR are summarized in Table 1.

TABLE 1 improved mi-CRISPR knockin efficiency

|  | CRISPR knockin efficiency (%) | mi-CRISPR knockin efficiency (%) | mi-CRISPR knockin improvement (fold change) |
| --- | --- | --- | --- |
| AAVS1 locus | | | |
| fibroblasts | 1.14 | 8.02 | 2.65 |
| airway stem cells | 0.71 | 1.53 | 2.15 |
| pluripotent stem cells | 0.56 | 1.16 | 2.07 |
| ROSA26 locus | | | |
| fibroblasts | 1.55 | 3.68 | 2.37 |
| airway stem cells | 0.54 | 1.28 | 2.37 |
| pluripotent stem cells | 0.59 | 1.48 | 2.51 |

Example 3—mi-CRISPR Reduces Off-Target Effects

During the development of embodiments of the technology described herein, it was contemplated that the mi-CRISPR technology described herein comprising use of the Cas9-BE27 fusion protein would reduce off-target events. In particular, it was contemplated that off-target events would be reduced, minimized, undetectable, and/or eliminated by mi-CRISPR, e.g., because HDR-mediated repair of DSBs uses homologous sequence on the sister chromosome. Data collected during experiments conducted during the development of embodiments of the technology described herein indicated that the off-target effects produced by conventional Cas9 were higher than the off-target effects produced by mi-CRISPR (FIG. 6, lane marked with "***").

Figure 7A:
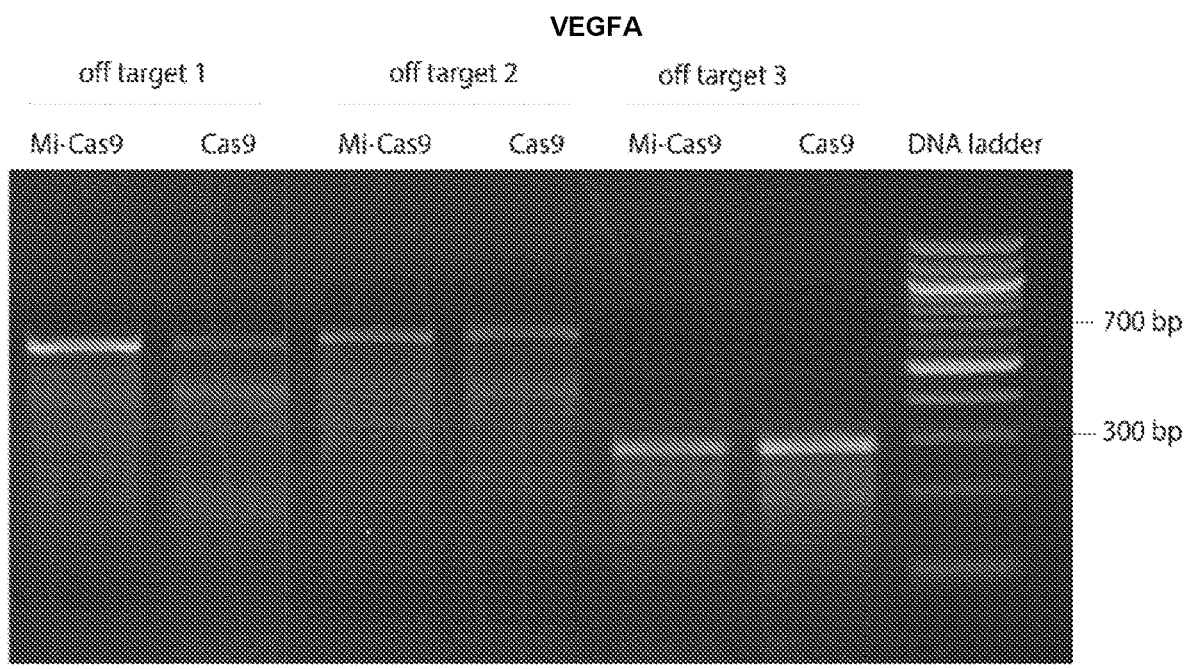
FIG. 7A is an image of an agarose gel showing the results of experiments to identify off-target effects associated with knockin of GFP at the VEGFA locus.
Figure 7B:
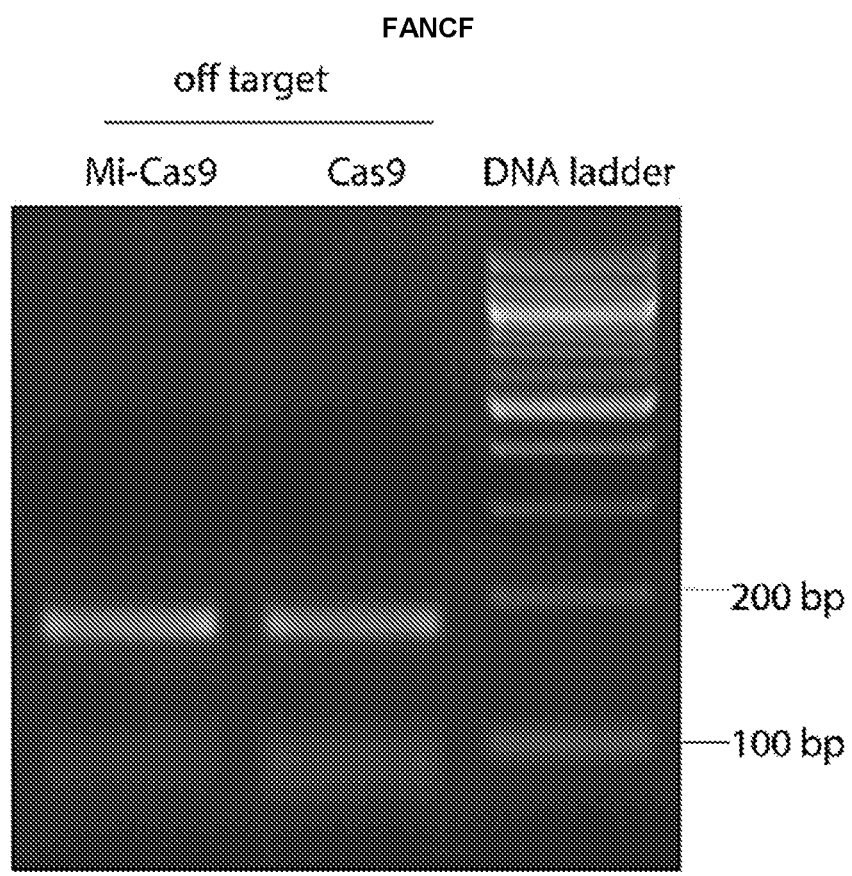
FIG. 7B is an image of an agarose gel showing the results of experiments to identify off-target effects associated with knockin of GFP at the FANCF locus.
Figure 7C:
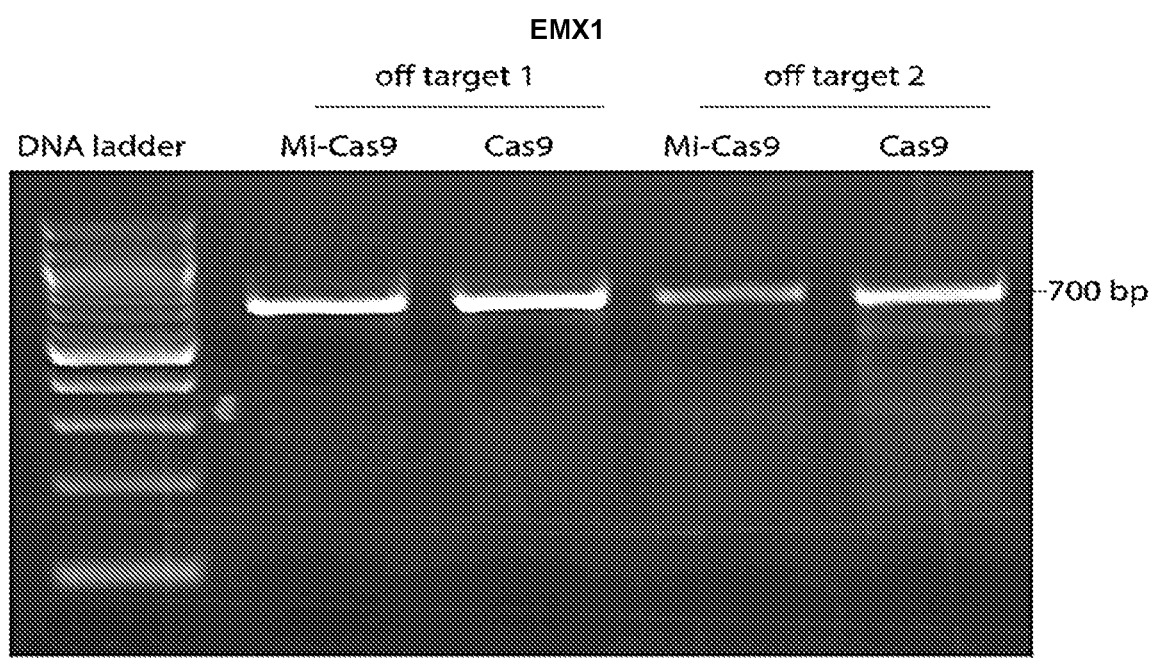
FIG. 7C is an image of an agarose gel showing the results of experiments to identify off-target effects associated with knockin of GFP at the EMX1 locus.
Figure 7D:
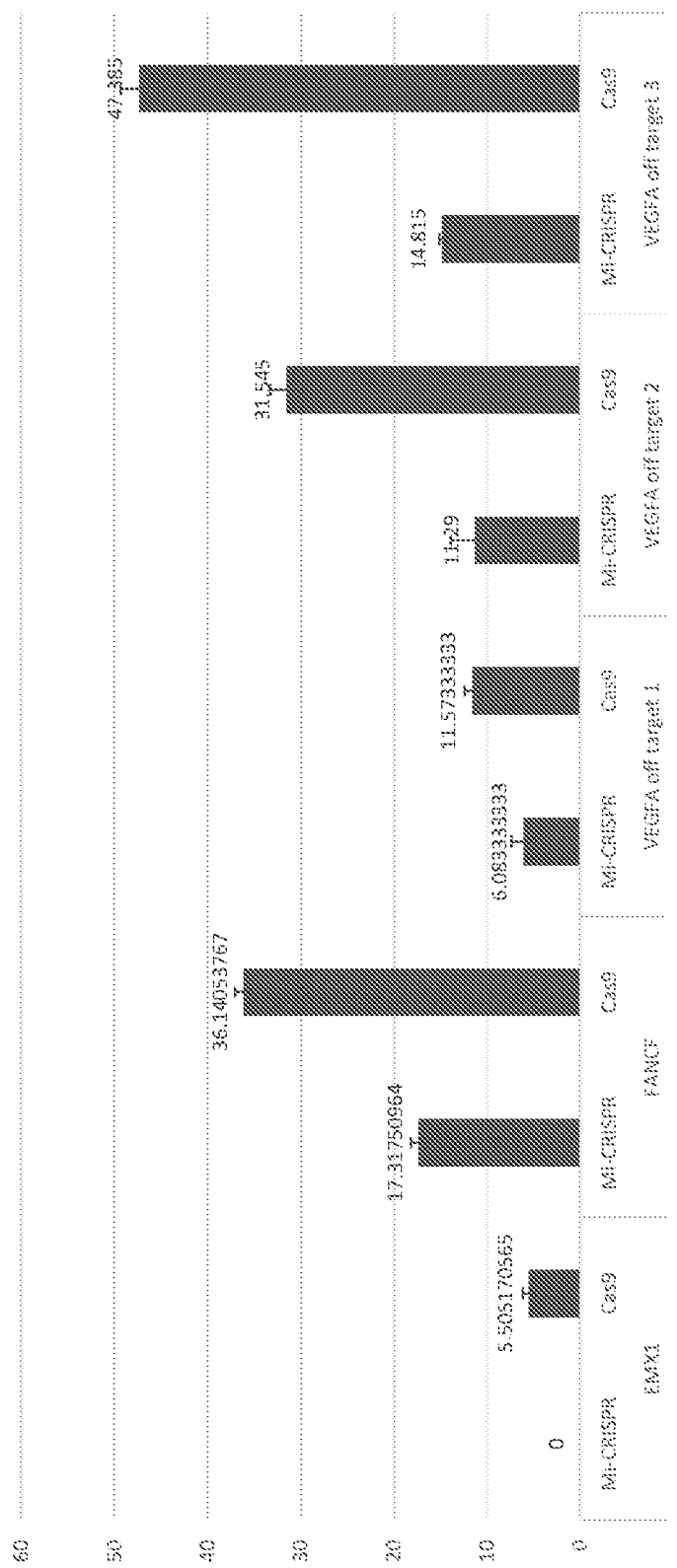
FIG. 7D is a bar plot showing the quantified data collected from the experiments shown in FIGS. 7A, 7B, and 7C.

The inherent off-target effects for CRISPR knockin at the AAVS1 and ROSA26 loci are both low. Accordingly, experiments were conducted during the development of the technology described herein to test off-target effects accompanying CRISPR and mi-CRISPR knockin at other loci known to be associated with problematic rates (e.g., greater than 10%) of off-target effects; VEGFA. FANCF, and EMX1 (FIGS. 7A-7D). Conventional CRISPR and mi-CRISPR were performed by co-transfecting human cells (e.g., HEK293 cells) with VEGFA, EMX1, or FANCF-specific sgRNA and conventional Cas9 or Cas9-BE27 fusion protein. T7E1 assays were used to measure off-target effects at sites known to be prone to off-target effects when the VEGFA, FANCF, and EMX1 loci are targeted by CRISPR (FIGS. 7A-7C). These results were confirmed by deepseq analysis (FIG. 7D).

For VEGFA, conventional CRISPR using conventional Cas9 produced off-target indel rates of 44.3%, 2.95% and 4.53%, respectively, at three off-target sites. In contrast, mi-CRISPR using the Cas9-BE27 fusion protein reduced the off-target rates to 0.55% and 0.28% at two of the off-target sites and produced no detectable off-target effect at the third site (FIGS. 7A and 7D). For FANCF1, conventional CRISPR using conventional Cas9 produced an off-target indel rate of 30.23% at a known off-target site. In contrast, mi-CRISPR using the Cas9-BE27 fusion protein reduced the off-target rate to 6.75% at this site (FIGS. 7B and 7D). For EMX1, conventional CRISPR using conventional Cas9 produced an off-target indel rate of 16.33% at a known off-target site. In contrast, mi-CRISPR using the Cas9-BE27 fusion protein reduced the same off-target rate to 0.62% (FIGS. 7C and 7D). The on-target indel rates for CRISPR and mi-CRISPR at these sites (assayed by deepseq) were approximately 8 to 9% and 20-27%, respectively. These results clearly indicate that mi-CRISPR reduces off-target indel events, e.g., relative to conventional CRISPR.

During the development of embodiments of the technology provided herein, further experiments were conducted to compare the off-target effects produced by conventional Cas9 to off-target effects produced by mi-CRISPR at several well-known loci that are reportedly associated with substantial off target rates (see, e.g., Fu (2013) "High-frequency off-target mutagenesis induced by CRISPR-Cas nucleases in human cells" Nature biotechnology 31(9): 822-826, incorporated herein by reference). In these experiments, the gRNAs sg1-VEGFA, sg2-VEGFA, and sg3-VEGFA were used to target VEGFA; the gRNA sg-FANCF was used to target FANCF; the gRNA sg-EMX1 was used to target EMX1; and the gRNA sg-RUNX1 was used to target RUNX1 (see, e.g., Fu, supra). See FIGS. 8A-8F.

In these experiments, the Cas9-BE27 fusion protein and conventional Cas9 were provided as nucleic acids to be translated by the host cell (e.g., by providing Cas9-BE27 fusion protein and conventional Cas9 in their plasmid DNA ("pDNA") forms) because pDNA-mediated gene editing has a higher off-target risk than Cas9 RNP-mediated gene editing (see, e.g., Kim (2014) "Highly efficient RNA-guided genome editing in human cells via delivery of purified Cas9 ribonucleoproteins" Genome research 24(6): 1012-1019, incorporated herein by reference). Deep sequencing (deepseq) analysis indicated a universal reduction of off-target indel edits in Ad293 cells when Cas9-BE27 fusion protein was used relative to conventional Cas9 (FIGS. 8A-F). Remarkably, the off-target indel rates in the Cas9-BE27 fusion protein group (0.72%, 0.48%, 5.38%, 3.56%, 1.05%, and 0%) were 77.3% to 100% lower than those in the conventional Cas9 group (6.46%, 38.0%, 23.8%, 26.7%, 12.8%, and 6.74%) for sg1-VEGFA, sg2-VEGFA2, sg3-VEGFA, sg-FANCF, sg-EMX1, and sg-RUNX1, respectively. Of note, for sg-RUNX1 the indel rates at the top off-target site by Cas9-BE27 fusion protein were reduced to below the detection threshold. These results indicate that the Cas9-BE27 fusion protein reduces off-target indel events relative to conventional Cas9.

Example 4—mi-CRISPR Reduces Off-Target Effects of Cas9 Variants

Figure 8A:
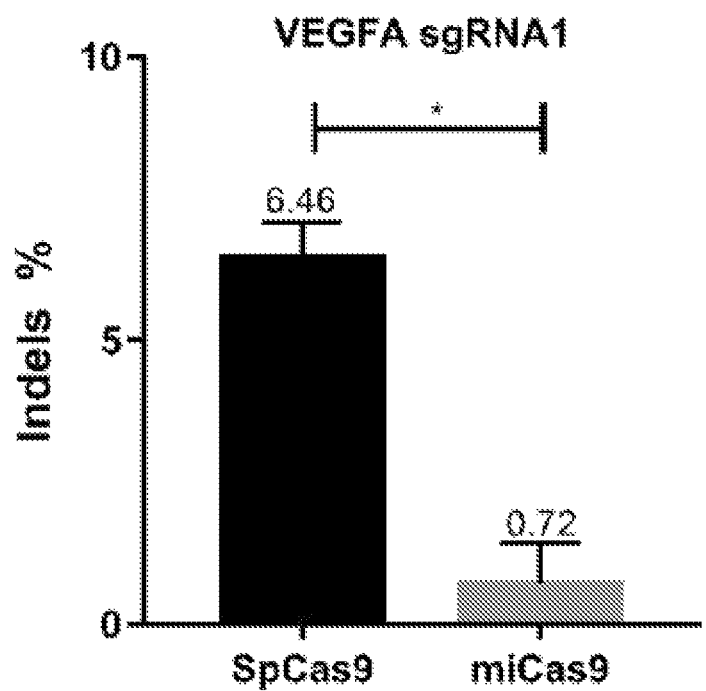
FIG. 8A is a bar plot indicating that the Cas9-BE27 fusion protein reduces off-target indel rates by sg1-VEGFA.
Figure 8B:
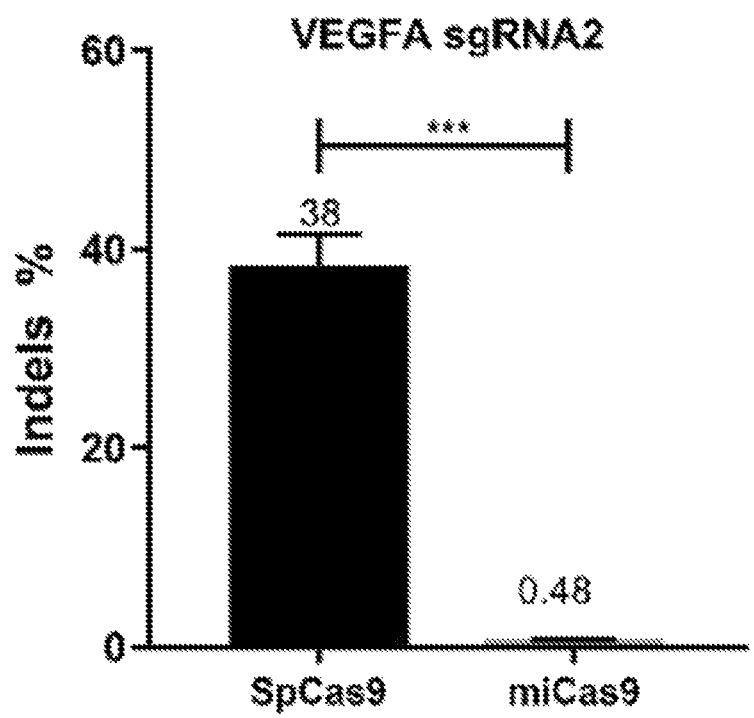
FIG. 8B is a bar plot indicating that the Cas9-BE27 fusion protein reduces off-target indel rates by sg2-VEGFA.
Figure 8C:
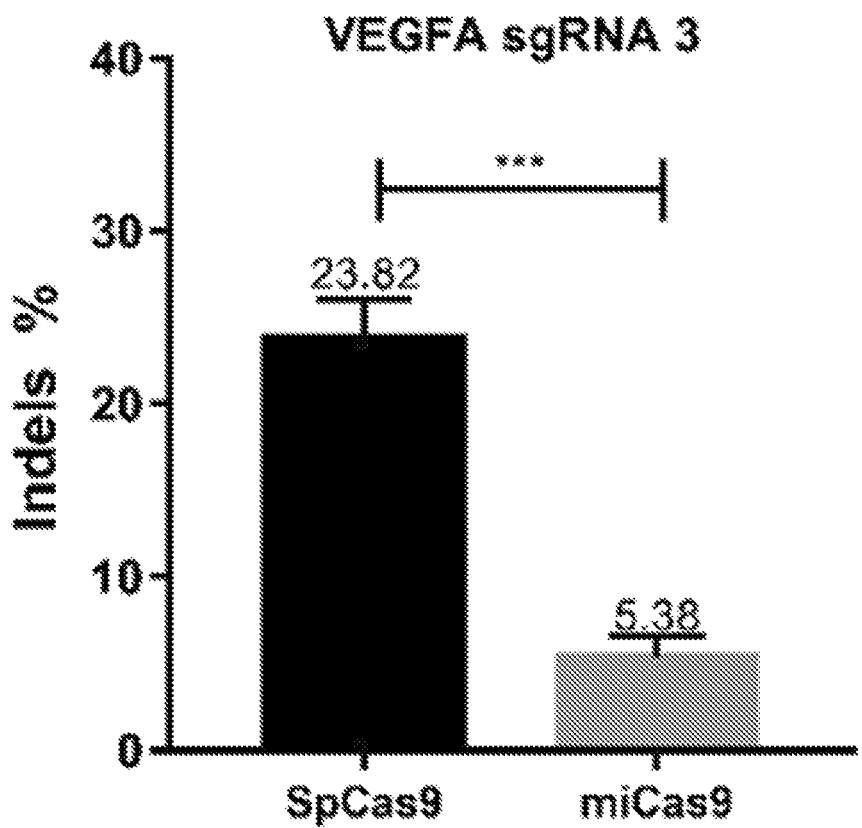
FIG. 8C is a bar plot indicating that the Cas9-BE27 fusion protein reduces off-target indel rates by sg3-VEGFA.
Figure 8D:
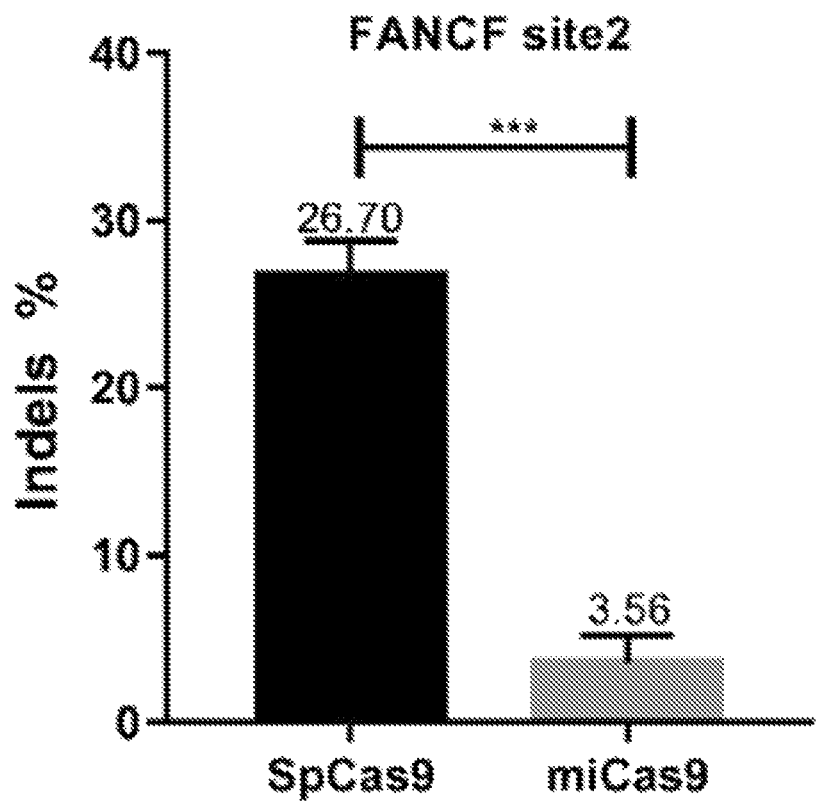
FIG. 8D is a bar plot indicating that the Cas9-BE27 fusion protein reduces off-target indel rates by sg-FANCF.
Figure 8E:
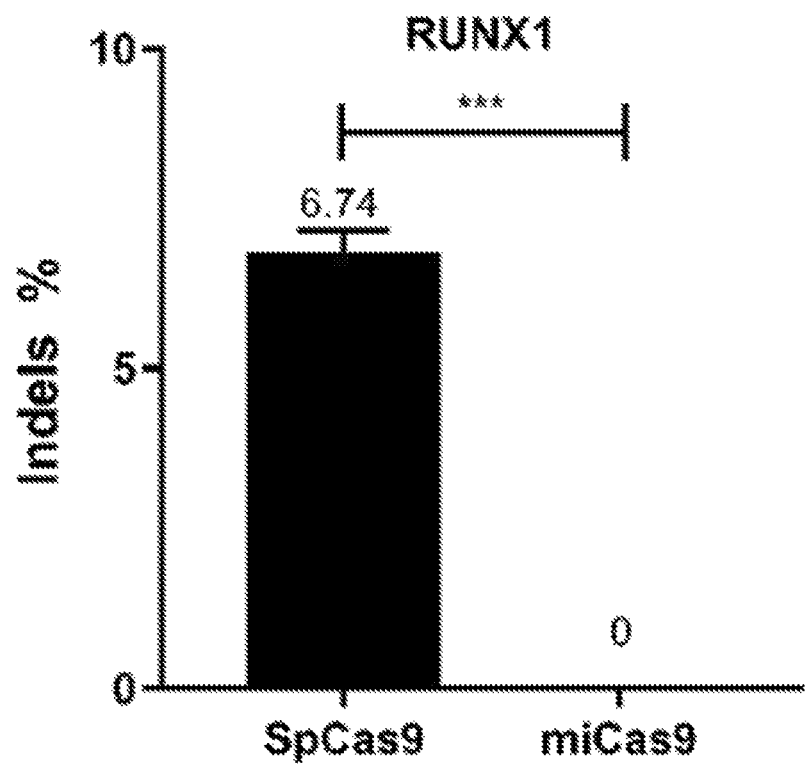
FIG. 8E is a bar plot indicating that the Cas9-BE27 fusion protein reduces off-target indel rates by sg-RUNX1.
Figure 8F:
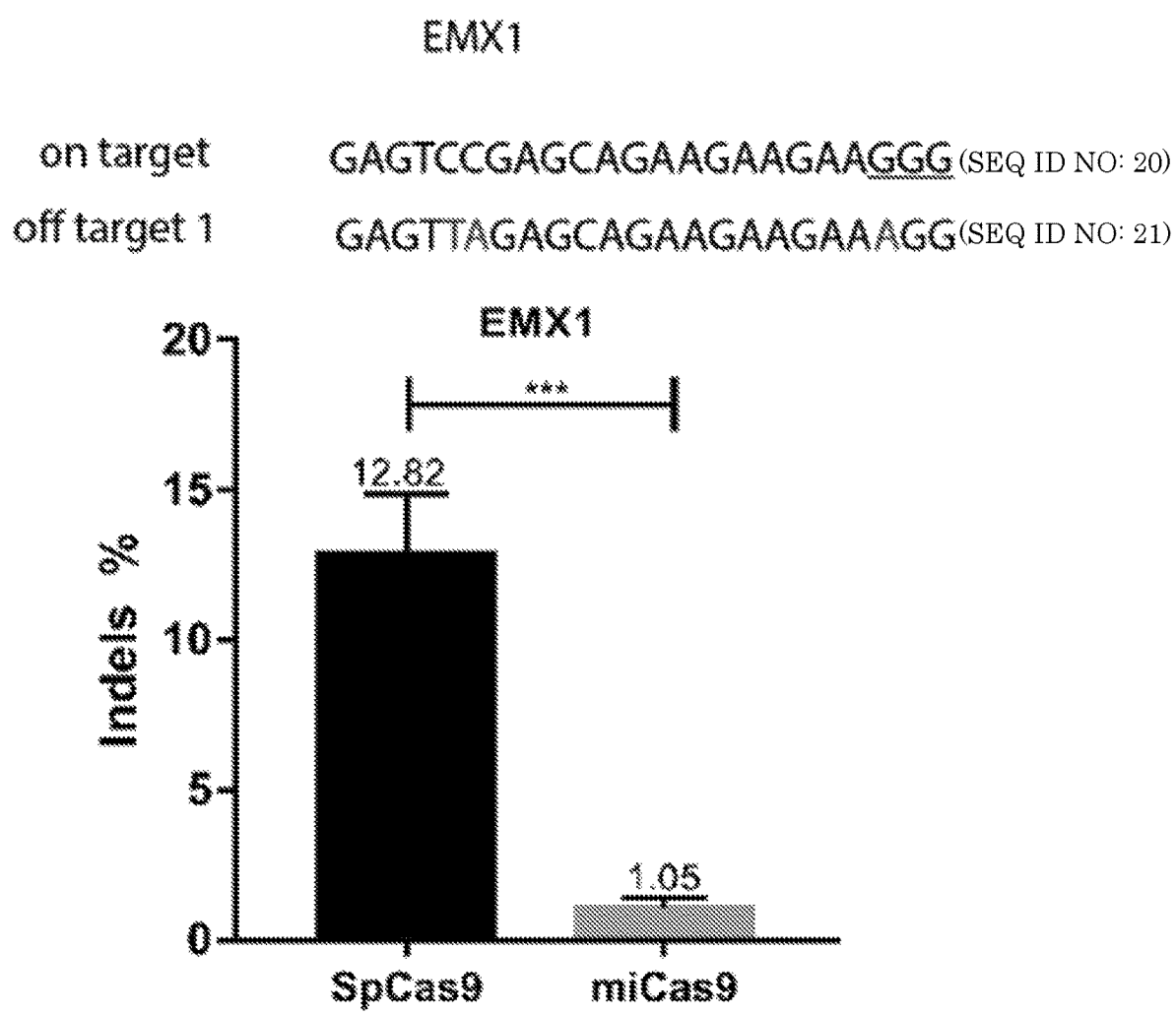
FIG. 8F is a bar plot indicating that the Cas9-BE27 fusion protein reduces off-target indel rates by sg-EMX1.
Figure 8G:
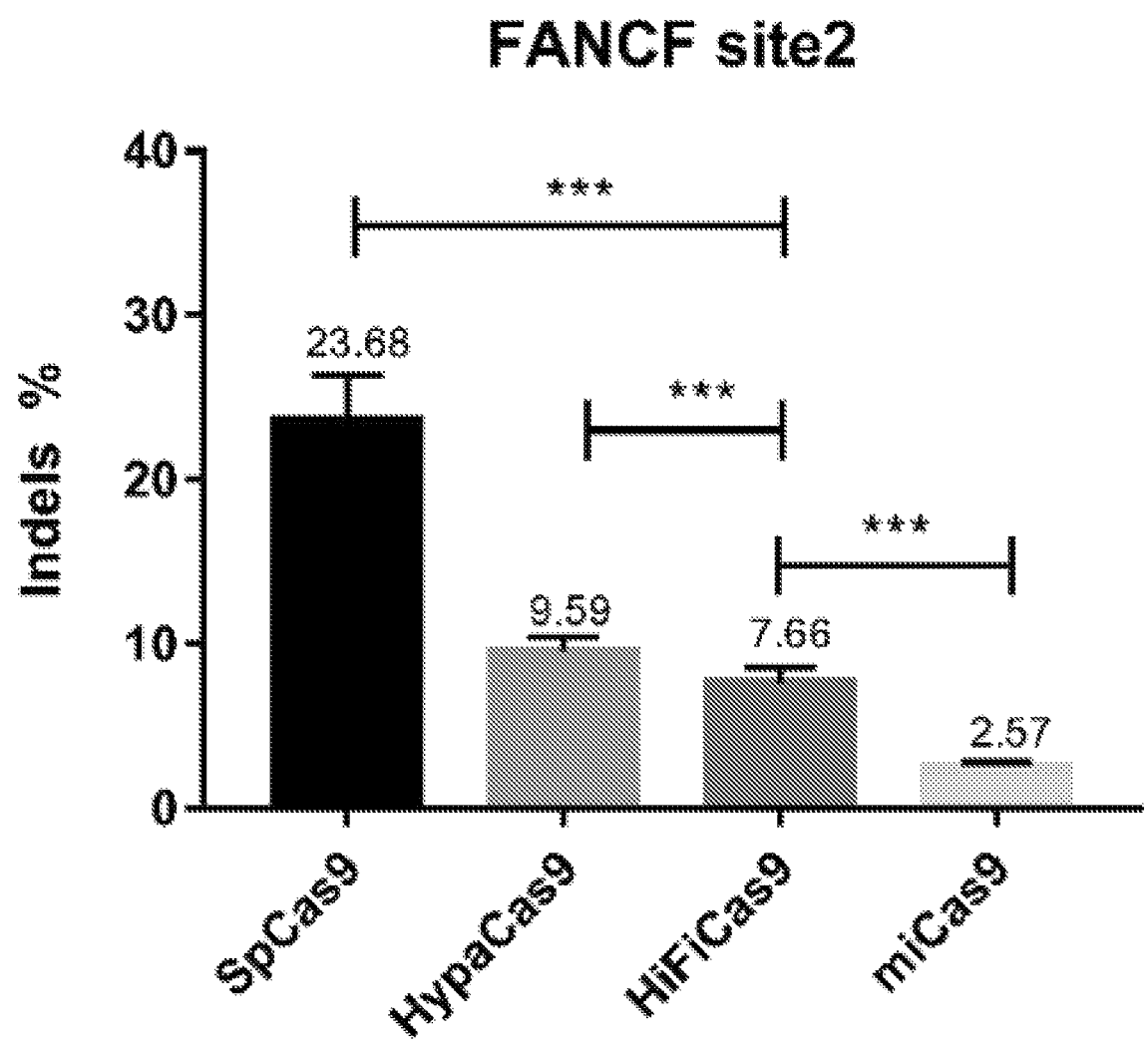
FIG. 8G is a bar plot comparing the off-target indel rates for sg-FANCF and the conventional Cas9, hypaCas9. HiFi-Cas9, and Cas9-BE27 fusion protein when provided as plasmid DNAs.
Figure 8H:
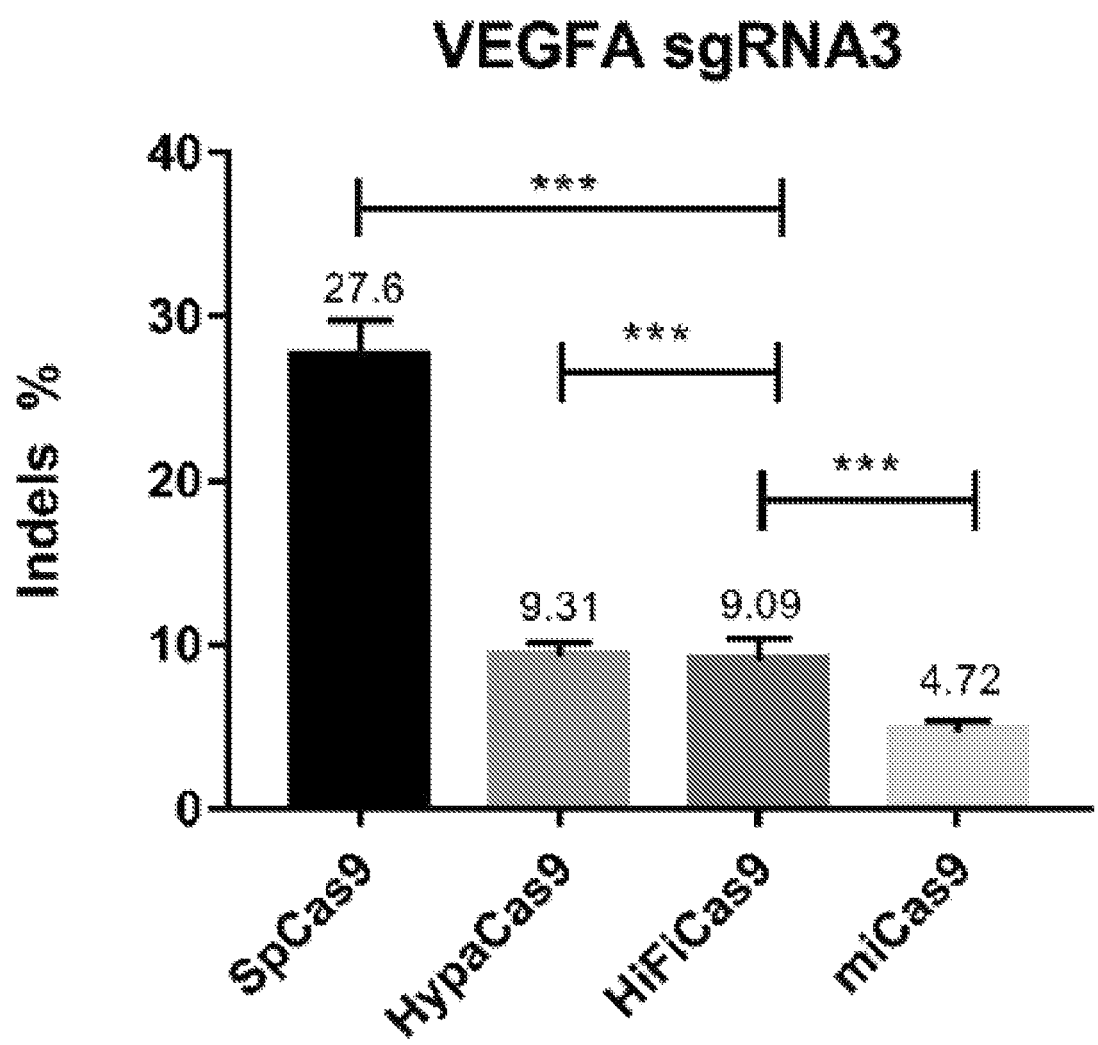
FIG. 8H is a bar plot comparing the off-target indel rates for sg3-VEGFA and the conventional Cas9, hypaCas9. HiFi-Cas9, and Cas9-BE27 fusion protein when provided as plasmid DNAs.
Figure 8I:
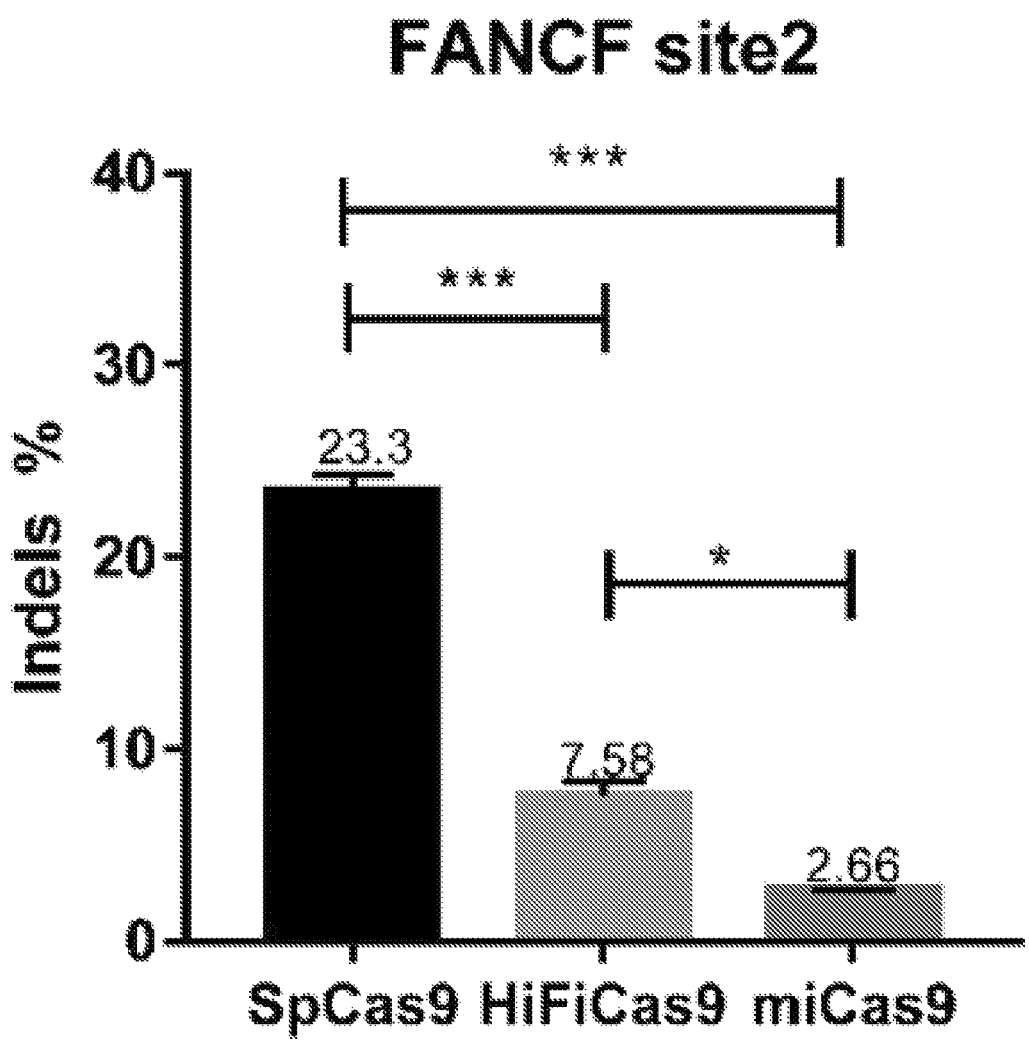
FIG. 8I is a bar plot comparing the off-target indel rates for sg3-FANCF and the conventional Cas9, hypaCas9, HiFi-Cas9, and Cas9-BE27 fusion protein when provided as RNPs.
Figure 8J:
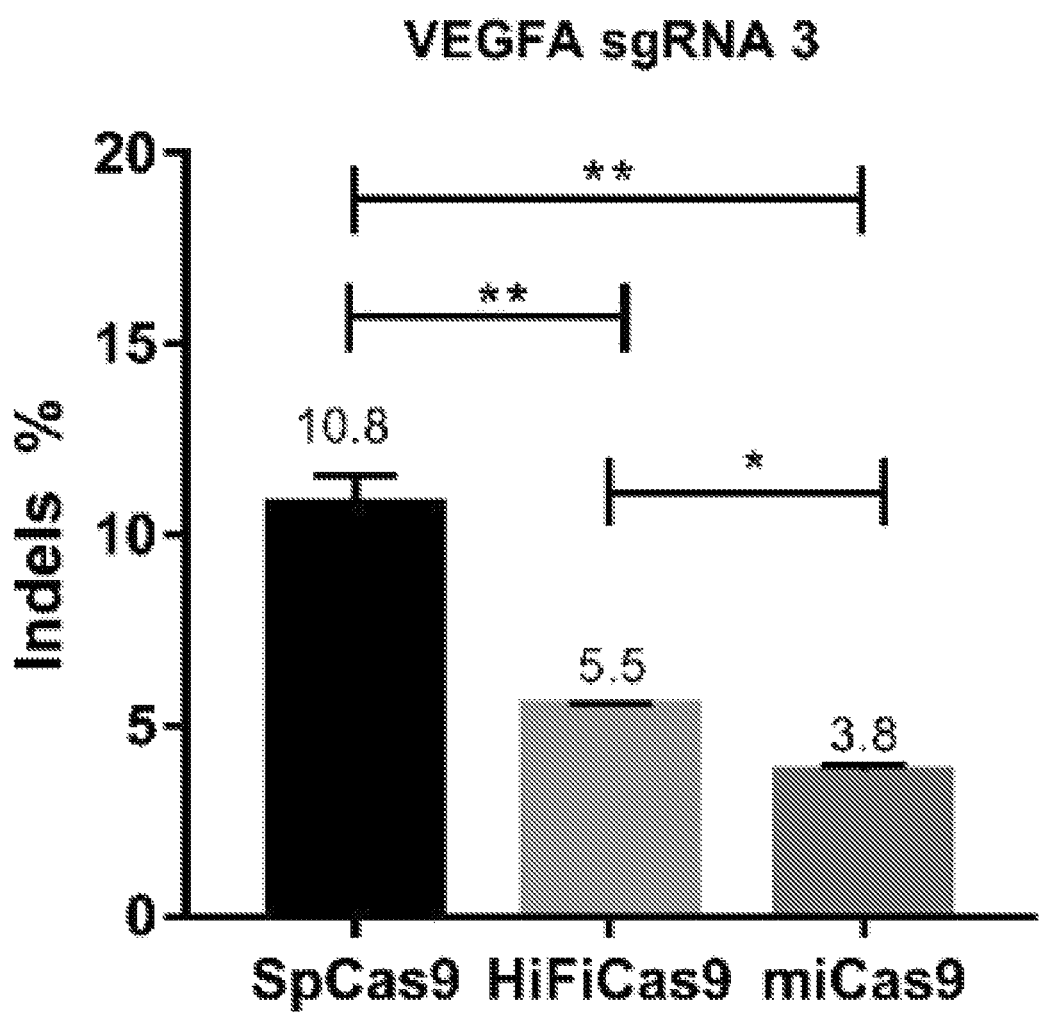
FIG. 8J is a bar plot comparing the off-target indel rates for sg3-VEGFA and the conventional Cas9, hypaCas9, HiFi-Cas9, and Cas9-BE27 fusion protein when provided as RNPs.
Figure 10A:
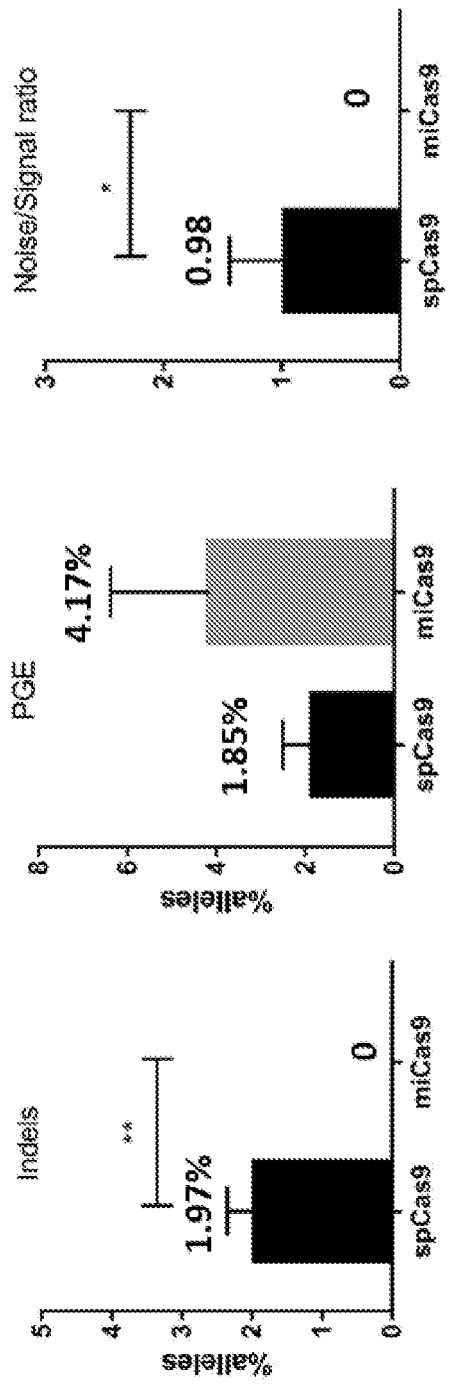
FIG. 10A is a series of bar plots showing the on-target indel rate, precise gene editing (PGE) rate, and Noise/Signal ratio for conventional Cas9 (spCas9) and the Cas9-BE27 fusion protein (miCas9) targeting the clinically significant locus B2M.
Figure 10B:
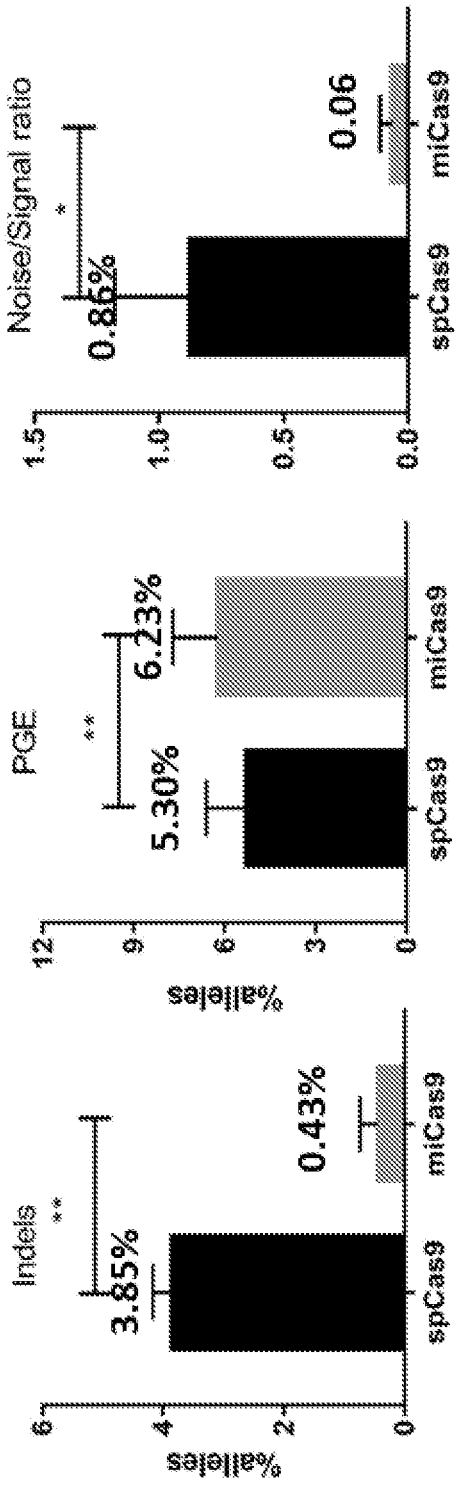
FIG. 10B is a series of bar plots showing the on-target indel rate, precise gene editing (PGE) rate, and Noise/Signal ratio for conventional Cas9 (spCas9) and the Cas9-BE27 fusion protein (miCas9) targeting the clinically significant locus NKX2.1.
Figure 10C:
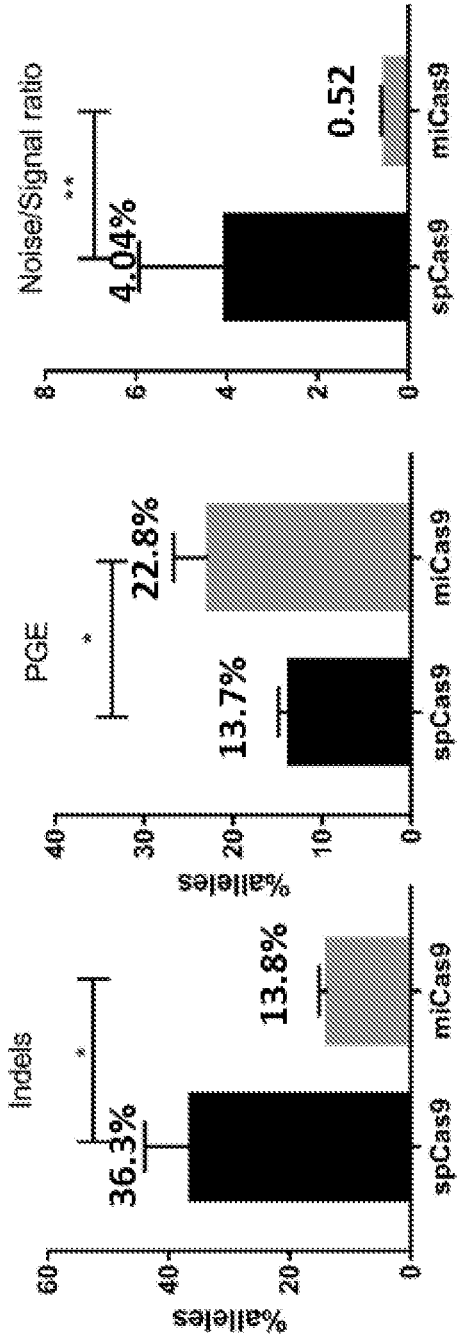
FIG. 10C is a series of bar plots showing the on-target indel rate, precise gene editing (PGE) rate, and Noise/Signal ratio for conventional Cas9 (spCas9) and the Cas9-BE27 fusion protein (miCas9) targeting the clinically significant locus HBB.
Figure 10D:
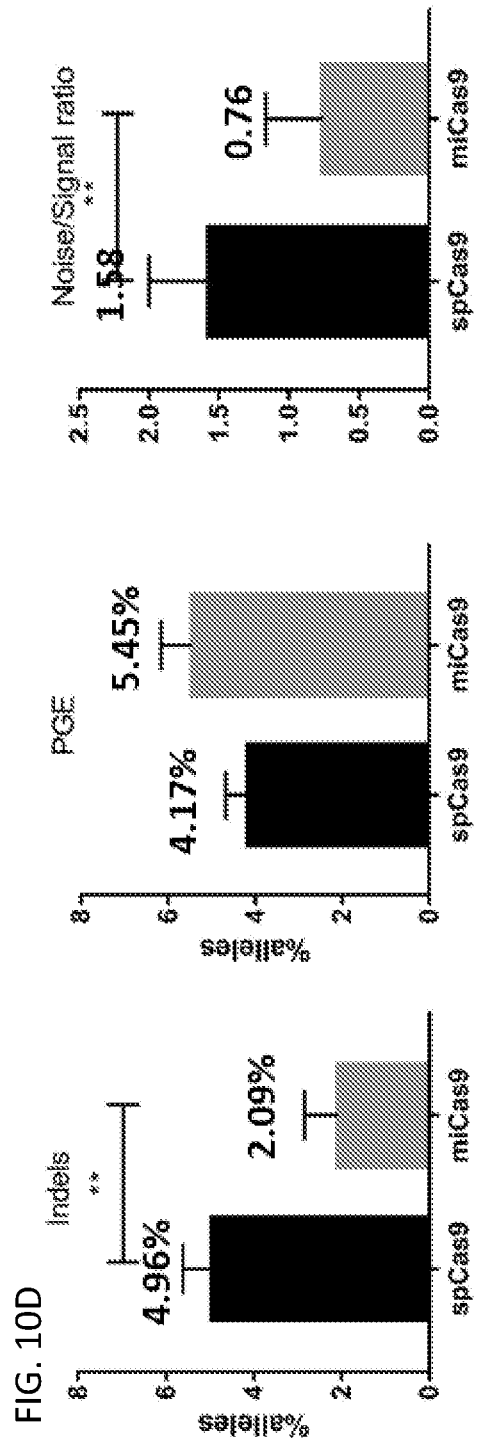
FIG. 10D is a series of bar plots showing the on-target indel rate, precise gene editing (PGE) rate, and Noise/Signal ratio for conventional Cas9 (spCas9) and the Cas9-BE27 fusion protein (miCas9) targeting the clinically significant locus EGFR.
Figure 10E:
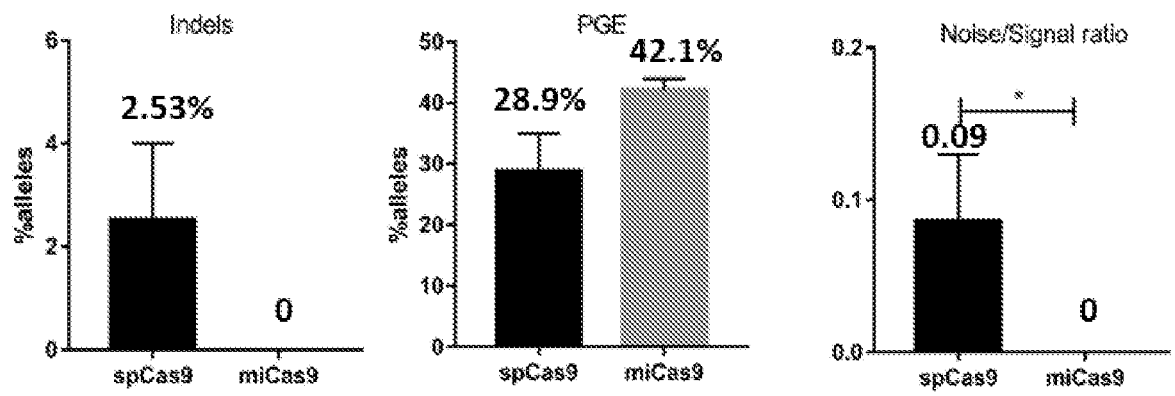
FIG. 10E is a series of bar plots showing the on-target indel rate, precise gene editing (PGE) rate, and Noise/Signal ratio for conventional Cas9 (spCas9) and the Cas9-BE27 fusion protein (miCas9) targeting the clinically significant locus Mybpc3.

During the development of embodiments of the technology provided herein, experiments were conducted to the Cas9-BE27 fusion protein with the Cas9 variants HiFiCas9 (see, e.g., Vakulskas (2018) "A high-fidelity Cas9 mutant delivered as a ribonucleoprotein complex enables efficient gene editing in human hematopoietic stem and progenitor cells. Nature medicine" 24(8): 1216-1224, incorporated herein by reference) and HypaCas9 (see. e.g., Chen (2017) "Enhanced proofreading governs CRISPR-Cas9 targeting accuracy" Nature 550(7676): 407-410, incorporated herein by reference), which have been reported to significantly reduce off-target editing events, sg-FANCF or sg3-VEGFA was delivered as plasmid DNAs to Ad293 and the off-target indel rates were measured by deepseq. The data collected indicated that the off-target indel rates were highest for conventional Cas9 (23.68% and 27.6%), followed by HypaCas9 (9.59% and 9.31%) and HiFiCas9 (7.66% and 9.09%), and were lowest for the Cas9-BE27 fusion protein (2.57% and 4.72%), respectively (FIGS. 8G and 8H). Because the conventional Ca9 and HiFiCas9 proteins are commercially available, experiments were conducted to compare their off-target indel rates using the proteins in their RNP forms relative to Cas9-BE27 fusion protein RNPs that were produced in-house. The data indicated that the off-target indel rates for the Cas9-BE27 fusion protein were lower (2.66% and 3.8%) than the off-target indel rates for HiFiCas9 (7.58 and 5.5%), both of which were significantly lower than the off-target indel rates (23.3% and 10.8%) for sg-FANCF and sg-VEGFA, respectively (FIGS. 8I and 8J). These results are consistent with the plasmid DNA results and show that the Cas9-BE27 fusion protein provides an effective Cas9 variant for reducing undesirable off-target indel rates.

Example 5—miCRISPR Reduces On-Target Indel (Noise) Rates

During the development of embodiments of the technology provided herein, experiments were conducted to test the use of the Cas9-BE27 fusion protein and conventional Cas9 for ssODN-mediated precise point mutations. Without being confined to theory, it was contemplated that the Cas9-BE27 fusion protein significantly reduces undesirable on-target indel (noise) rates, e.g., to a similar extent that has been observed in reducing "hot" off-target indel rates. It was further contemplated that the Cas9-BE27 fusion protein improves precise genome editing (PGE) rates. Improvement of PGE rates was contemplated to be smaller than the reduction of on-target noise because RAD51 participates in SDSA mediated DSB repair and SDSA has been shown to contribute to ssODN mediated PGE while SSA mediated DSB repair, another major mechanism suggested for ssODN mediated PGE, does not utilize RAD51 (see, e.g., Kim (2014) Highly efficient. RNA-guided genome editing in human cells via delivery of purified Cas9 ribonucleoproteins. Genome research 24(6): 1012-1019; DeWitt. (2016) Selection-free genome editing of the sickle mutation in human adult hematopoietic stem/progenitor cells. Sci Transl Med 8(360): 360 ra134; Kan (2017) Mechanisms of precise genome editing using oligonucleotide donors. Genome research 27(7): 1099-1111; and Harmsen (2018) DNA mismatch repair and oligonucleotide end-protection promote base-pair substitution distal from a CRISPR/Cas9-induced DNA break. Nucleic Acids Res 46(6): 2945-2955, each of which is incorporated herein by reference).

During these experiments, the Cas9-BE27 fusion protein and conventional Cas9 RNPs and their corresponding gRNAs and ssODNs (see, e.g., FIG. 9) were used to produce point mutations at several clinically significant loci including B2M, NKX2.1, HBB. EGFR, and MYBPC3. Deepseq was used to analyze PGE rates and on-target indel rates. On-target indel rates were reduced at all loci by the Cas9-BE27 fusion protein relative to the on-target indel rates produced by conventional Cas9 (FIG. 10A to 10E). In particular, the reduction in the on-target indel rates ranged from a reduction of 57.9% to 100%, which is consistent with the observations that the Cas9-BE27 fusion provides a significant reduction of indel rates at "hot" off-target loci shown in FIG. 8A-8J. The PGE rates achieved by the Cas9-BE27 fusion protein were similar (e.g., for B2M. EGFR. MYBPC3) or higher (e.g. for NKX2.1 and HBB) than the PGE rates provided by conventional Cas9 (FIG. 10A to 10E). Together, the Cas9-BE27 fusion protein provides significantly reduced Noise (e.g., on-target indel) over Signal (e.g., PGE) ratios (FIG. 10A-10E) that were reduced by 51.8% to 100% relative to conventional Cas9. The on-target indel edits by the Cas9-BE27 fusion protein were undetectable at some loci (e.g., 132M and MYBPC3). These data indicate that the Cas9-BE27 fusion protein reduces on-target indel events relative to conventional Cas9, while providing the same or improved PGE rates relative to conventional Cas9, which together provide a significantly enhanced S/N (i.e., reduced N/S) ratio relative to conventional Cas9.

Example 6—mi-CRISPR has Robust DSB Activity

During the development of embodiments of the technology provided herein, experiments were conducted to confirm that the Cas9-BE27 fusion protein does not have reduced activity of producing DSB. In particular, experiments were conducted to exclude the possibility that the reduced off-target and on-target indel rates provided by the Cas9-BE27 fusion protein are due to a compromised DSB generation capacity. In particular, experiments were conducted to verify that the observed reduction in on-target and off-target indel rates result from the Cas9-BE27 fusion protein having enhanced HDR capacity, thus providing a robust and precise repair after DSB generation. DNA repair is cell cycle dependent—in particular, NHEJ takes place at the G0 and G1 stages and HR takes place primarily at the S stage (Heyer (2010) Regulation of homologous recombination in eukaryotes. Annu Rev Genet 44: 113-139, incorporated herein by reference) and rarely if ever at G0. Accordingly, serum starvation was used to synchronize the cells to the G0 stage prior to Cas9 editing.

Figure 11:
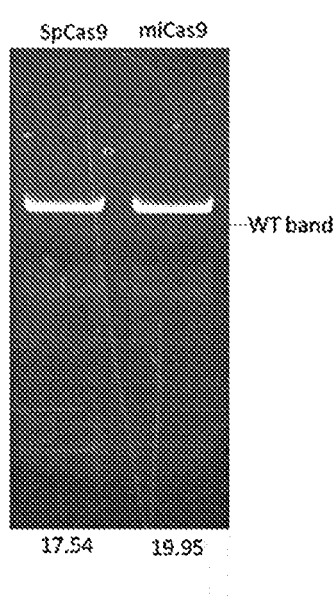
FIG. 11 shows photographs of agarose gels indicating that the indel rates are similar at off-target loci for conventional Cas9 (spCas9) and the Cas9-BE27 fusion protein (miCas9) when used with sg-FNACF, sg2-VEGFA, or sg3-VEGFA guide RNAs.
Figure 11:
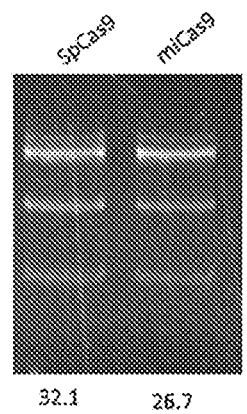
Figure 11:
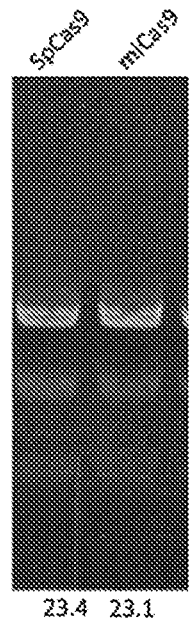
Figure 12A:
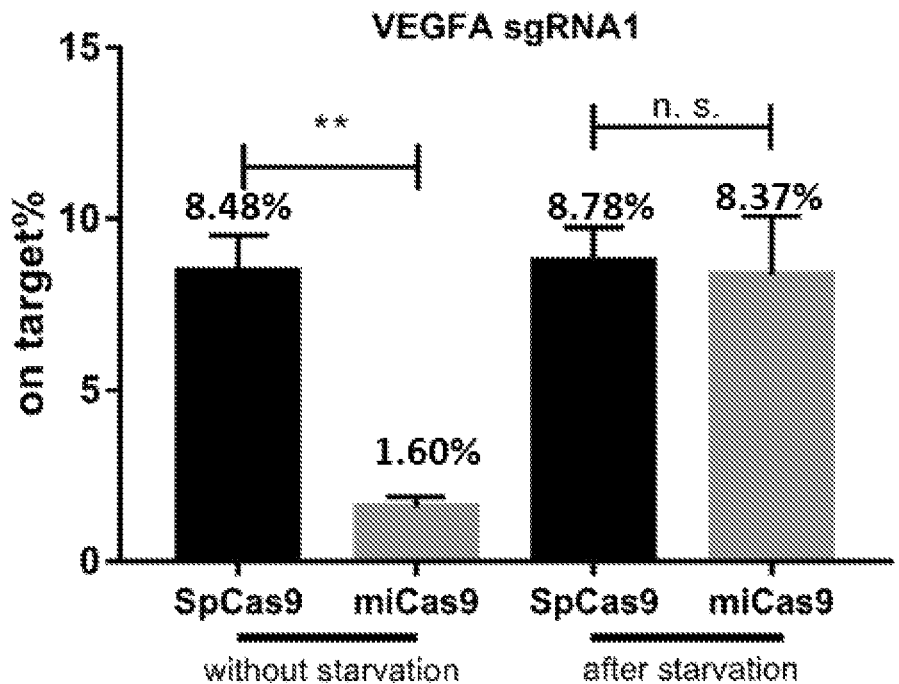
FIG. 12A is a bar plot of data from experiments testing the effects of serum starvation on indel rates for the conventional Cas9 (spCas9) and the Cas9-BE27 fusion (miCas9) when used with sg1-VEGFA.
Figure 12B:
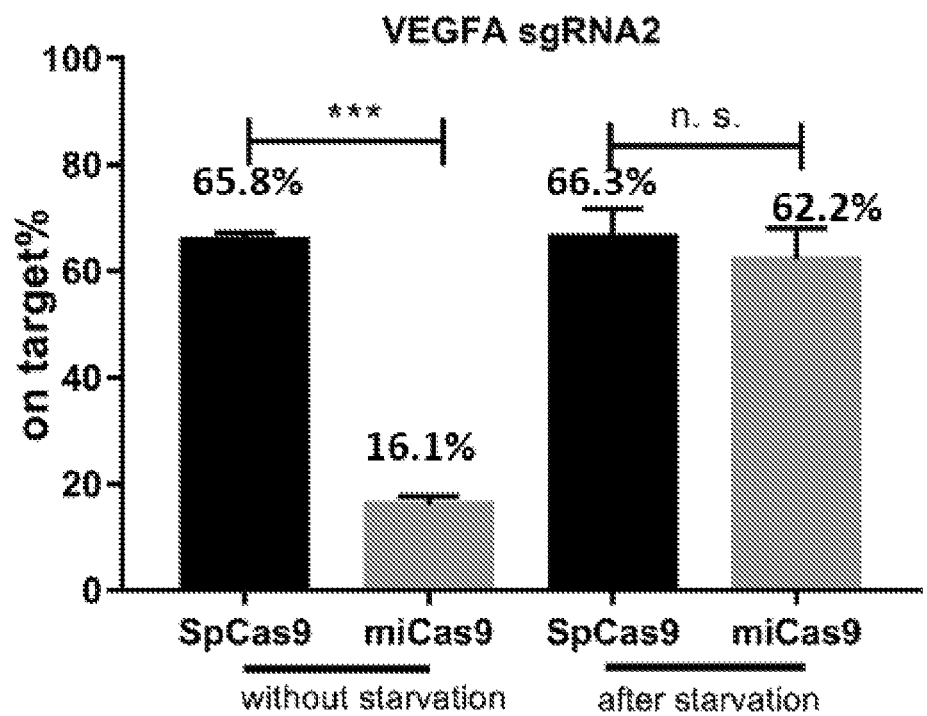
FIG. 12B is a bar plot of data from experiments testing the effects of serum starvation on indel rates for the conventional Cas9 (spCas9) and the Cas9-BE27 fusion (miCas9) when used with sg2-VEGFA.
Figure 12C:
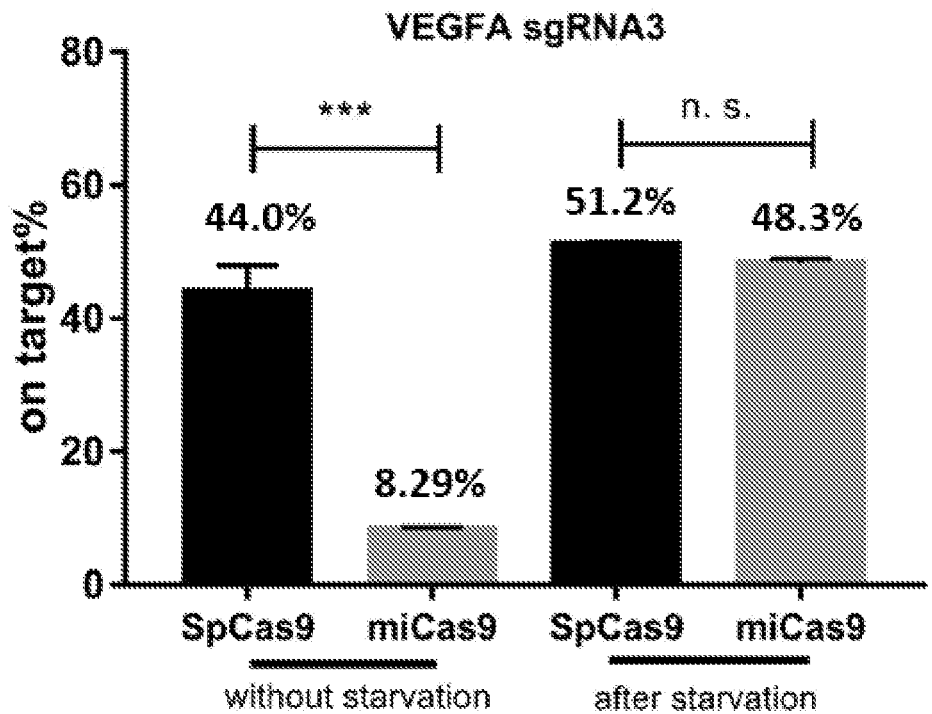
FIG. 12C is a bar plot of data from experiments testing the effects of serum starvation on indel rates for the conventional Cas9 (spCas9) and the Cas9-BE27 fusion (miCas9) when used with sg3-VEGFA.
Figure 12D:
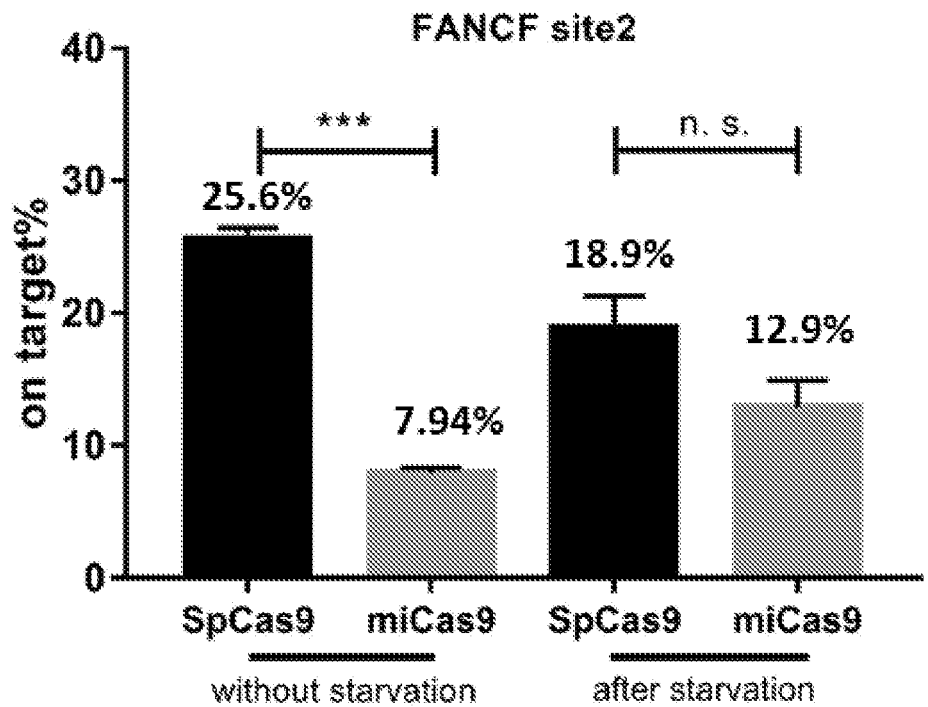
FIG. 12D is a bar plot of data from experiments testing the effects of serum starvation on indel rates for the conventional Cas9 (spCas9) and the Cas9-BE27 fusion (miCas9) when used with sg-FANCF.
Figure 12E:
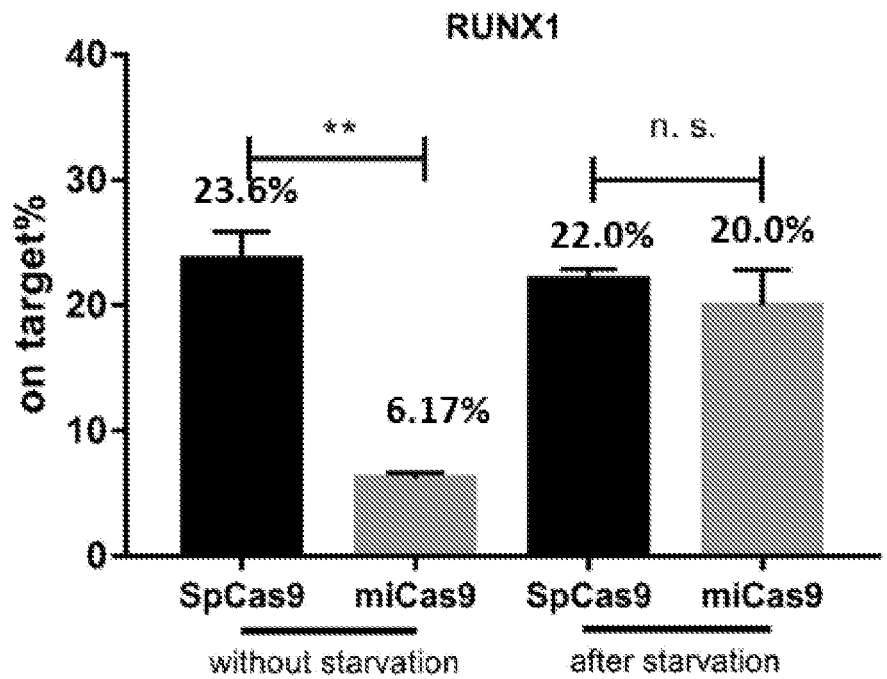
FIG. 12E is a bar plot of data from experiments testing the effects of serum starvation on indel rates for the conventional Cas9 (spCas9) and the Cas9-BE27 fusion (miCas9) when used with sg-RUNX1.
Figure 12F:
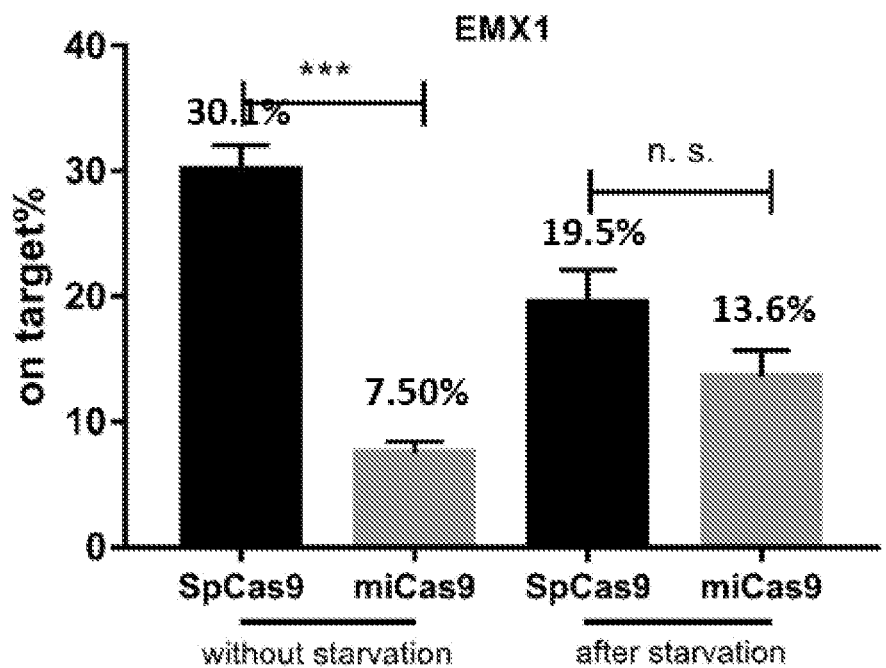
FIG. 12F is a bar plot of data from experiments testing the effects of serum starvation on indel rates for the conventional Cas9 (spCas9) and the Cas9-BE27 fusion (miCas9) when used with sg-EMX1.

The data collected indicated that the off-target indel rates using sg-FANCF, sg2-VEGFA, and sg3-VEGFA were comparable for the Cas9-BE27 fusion protein and conventional Cas9 (see, e.g., FIG. 11). In addition, the indel rates were significantly lower for the Cas9-BE27 fusion protein than for conventional Cas9. In contrast, after serum starvation the indel rates became similar for Cas9-BE27 and conventional Cas9 for all gRNAs tested, including sg1-VEGFA, sg2-VEGFA, sg3-VEGFA, sg-FANCF, sg-RUNX1, and sg-EMX1 (FIG. 12A to 12F). These data indicate that the reduction in on-target and off-target indel rates by the Cas9-BE27 fusion protein relative to conventional Cas9 was caused by higher faithful repair after DSB generation rather than a reduced DSB generation efficiency.

Example 7—BE27 Generally Increases the Specificity of Cas9-Like Proteins

Figure 13A:
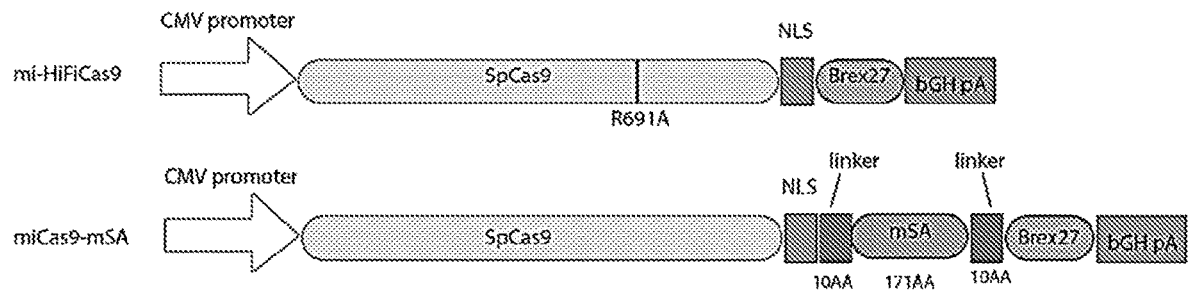
FIG. 13A is a schematic drawing showing the miHiFi-Cas9 and miCas9mSA constructs. "Brex27" indicates the BE27 domain and "SpCas9" indicates the Cas9 domain.
Figure 13B:
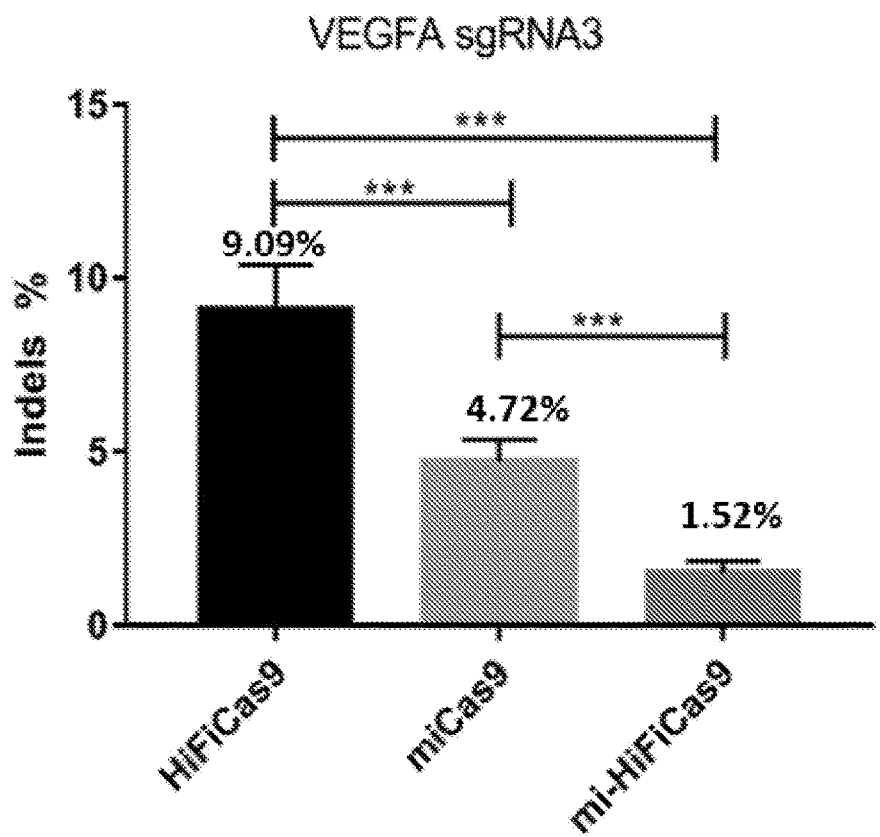
FIG. 13B is a bar plot showing the off-target indel rates for HiFiCas9, the Cas9-BE27 fusion protein (miCas9), and miHiFiCas9 when used with sg3-VEGFA
Figure 13C:
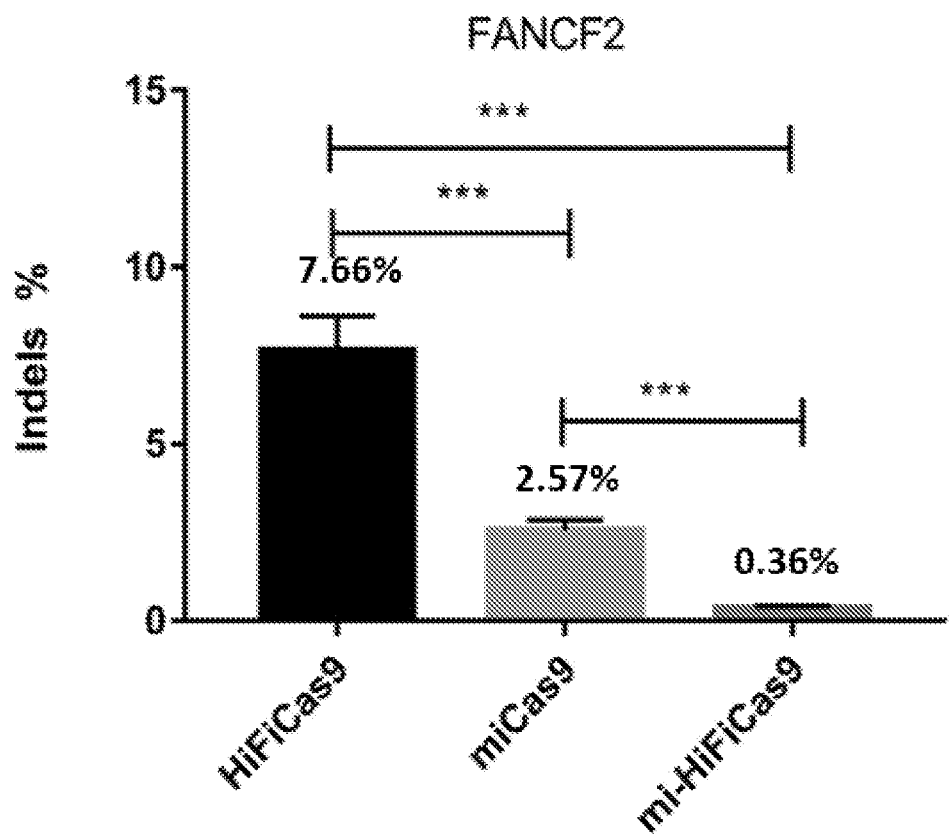
FIG. 13C is a bar plot showing the off-target indel rates for HiFiCas9, the Cas9-BE27 fusion protein (miCas9), and miHiFiCas9 when used with sg-FANCF.
Figure 13D:
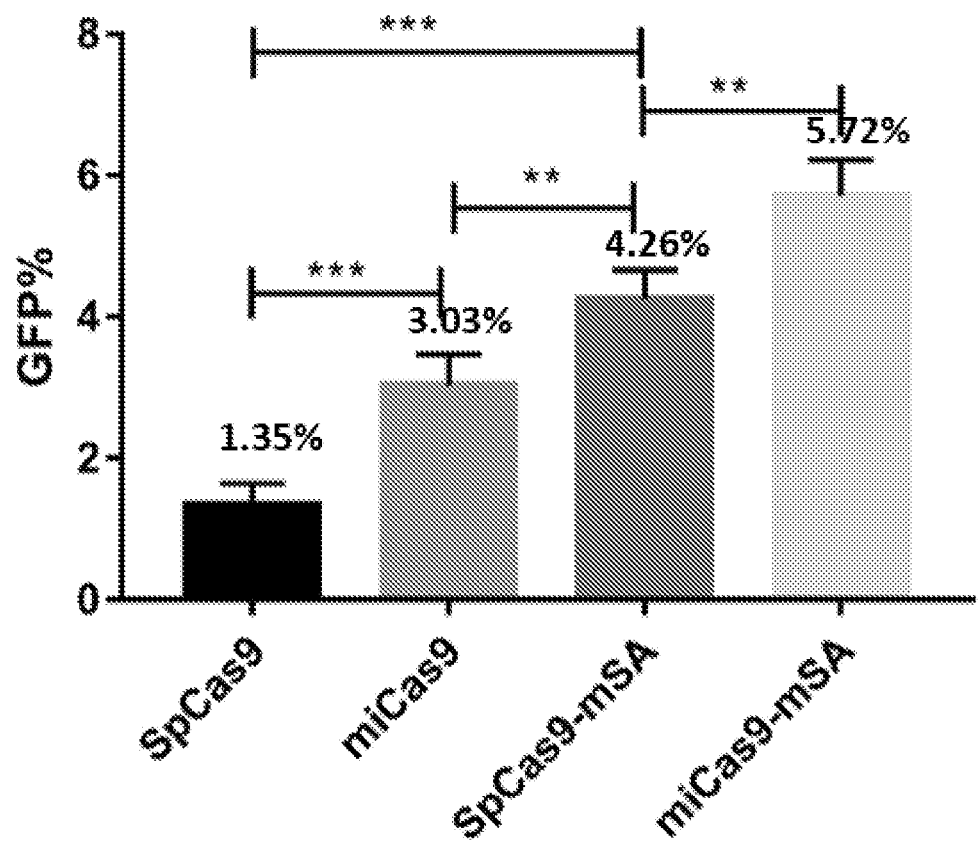
FIG. 13D is a bar plot showing the rates for KI of GFP using a large size donor by conventional Cas9 (spCas9), the Cas9-BE27 fusion (miCas9), spCas9mSA, and miCas9mSA.

The BE27 domain of 36 amino acids provides a "plug and play" domain for fusing to other gene editing nucleases without significantly increasing the protein size. During the development of embodiments of the technology provided herein, two constructs were produced and tested (see. e.g., FIG. 13A). First, miHiFiCas9 was constructed by fusing the BE27 domain to HiFiCas9 to test if the off-target indel rate for the miHiFiCas9 would be reduced relative to HiFiCas9. Off-target indel rates were measured for miHiFiCas9, HiFi-Cas9, and mi-Cas9 introduced on plasmids. The data collected indicated that miHiFiCas9 reduced the off-target indel rates of sg3-VEGFA or sg-FANCF to a new low level (1.52% and 0.36%) relative to HiFiCas9 (9.09% and 7.66%) and mi-Cas9 (4.72% and 2.51%) (FIG. 13B and FIG. 13C). Second, miCas9mSA was produced by fusing the BE27 domain to spCas9mSA, which increases large-size gene KI rates by enriching donor templates at DSB sites (see. e.g., Gu (2018) Efficient generation of targeted large insertions by microinjection into two-cell-stage mouse embryos. Nature biotechnology 36(7): 632-637, incorporated herein by reference), to test if the miCas9mSA further increased KI rates. Data were collected to compare the success rates of knocking-in the GFP construct to the ROSA26 locus in Ad293 using conventional Cas9, the Cas9-BE27 fusion protein, spCas9mSA, and miCas9mSA in their plasmid DNA forms. Flow cytometry results indicated that the highest GFP rate, an indicator of KI, was provided by miCas9mSA (5.72%), followed by spCas9mSA (4.26%) and the Cas9-BE27 fusion protein (3.03%). The lowest rate was provided by conventional Cas9 (1.35%) (FIG. 13D). These data indicate that the BE27 domain is compatible and synergistic with a number of Cas9 proteins and variants, and thus provides a general approach to improving CRISPR technologies.

In sum, provided herein is an improved CRISPR technology ("mi-CRISPR") comprising use of a mi-Cas9 protein, e.g., a Cas9-BE27 fusion protein as described herein. The technology finds use in genome editing (e.g., precise genome editing). Comparing to c-Cas9, Embodiments of the technology provide an improve gene editing technology for producing large fragment knock-ins. Relative to conventional CRISPR technologies, the knock-in rates provided by embodiments of the technology are 2-3 fold improved. Further, the technology provided herein also reduces, minimizes, and/or eliminates off-target editing events. Accordingly, the technology finds use in nuclease mediated therapeutics.

All publications and patents mentioned in the above specification are herein incorporated by reference in their entirety for all purposes. Various modifications and variations of the described compositions, methods, and uses of the technology will be apparent to those skilled in the art without departing from the scope and spirit of the technology as described. Although the technology has been described in connection with specific exemplary embodiments, it should be understood that the invention as claimed should not be unduly limited to such specific embodiments. Indeed, various modifications of the described modes for carrying out the invention that are obvious to those skilled in the art are intended to be within the scope of the following claims.

We claim:

1. A gene editing fusion protein comprising a gene editing nuclease domain fused to a plurality of at least two BE27 domains, wherein the gene editing nuclease domain comprises a CRISPR-associated system (Cas) protein domain and each BE27 domain of said plurality of BE27 domains comprises a polypeptide having the amino acid sequence of SEQ ID NO: 1.

2. The gene editing fusion protein of claim 1 wherein said Cas protein domain is from a Cas protein selected from the group consisting of Cas1, Cas1B, Cas2, Cas3, Cas4, Cas5, Cas6, Cas7, Cas8, Cas9, Cas10, Cas13, Csy1, Csy2, Csy3, Cse1, Cse2, Csc1, Csc2, Csa5, Csn2, Csm2, Csm3, Csm4, Csm5, Csm6, Cmr1, Cmr3, Cmr4, Cmr5, Cmr6, Csb1, Csb2, Csb3, Csx17, Csx14, Csx10, Csx16, CsaX, Csx3, Csx1, Csx15, Csf1, Csf2, Csf3, Csf4, Cpf1, C2c1, C2c2, HiFiCas9, spCas9mSA, HypaCas9, and xCas9.

3. The gene editing fusion protein of claim 1, wherein said plurality of BE27 domain comprises a tandem array of BE27 domains.

4. The gene editing fusion protein of claim 1, wherein said plurality of BE27 domains comprises one or more linker sequences separating the BE27 domain.

5. The gene editing fusion protein of claim 1, wherein said plurality of BE27 domains comprises 2-10 BE27 domains.

6. A composition comprising the gene editing fusion protein of claim 1.

7. The composition of claim 6, further comprising a gRNA.

8. The composition of claim 6, further comprising a donor nucleic acid.

9. The composition of claim 6, further comprising a target nucleic acid.

10. The composition of claim 8, wherein said donor nucleic acid comprises 100 to 1000 bp.

11. The composition of claim 8, wherein said donor nucleic acid comprises 1000 to 10,000 bp.

12. The composition of claim 6, further comprising a RAD51 protein or a nucleic acid encoding a RAD51 protein.

13. The composition of claim 6, further comprising a plurality of RAD51 proteins.

14. The composition of claim 6, further comprising a nucleic acid comprising a knockin.

15. The composition of claim 14, wherein said nucleic acid comprising a knockin comprises a sequence of a donor nucleic acid.

* * * * *

UNITED STATES PATENT AND TRADEMARK OFFICE
CERTIFICATE OF CORRECTION

| | | |
|---|---|---|
| PATENT NO. | : 12,018,297 B2 | Page 1 of 1 |
| APPLICATION NO. | : 17/258776 | |
| DATED | : June 25, 2024 | |
| INVENTOR(S) | : Jie Xu et al. | |

It is certified that error appears in the above-identified patent and that said Letters Patent is hereby corrected as shown below:

In the Claims

Claim 3, Column 87, Line 36 reads:
"plurality of BE27 domain comprises a tandem array of BE27",
Whereas it should read:
"plurality of BE27 domains comprises a tandem array of BE27".

Claim 4, Column 87, Line 40 reads:
"sequences separating the BE27 domain.",
Whereas it should read:
"sequences separating the BE27 domains.".

Signed and Sealed this
Fifth Day of November, 2024

Katherine Kelly Vidal
*Director of the United States Patent and Trademark Office*